(12) United States Patent
Joung et al.

(10) Patent No.: US 9,885,033 B2
(45) Date of Patent: Feb. 6, 2018

(54) INCREASING SPECIFICITY FOR RNA-GUIDED GENOME EDITING

(71) Applicant: The General Hospital Corporation, Boston, MA (US)

(72) Inventors: J. Keith Joung, Winchester, MA (US); James Angstman, Cambridge, MA (US); Jeffry D. Sander, Ames, IA (US); Morgan Maeder, Brookline, MA (US); Shengdar Tsai, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 13 days.

(21) Appl. No.: 14/776,620

(22) PCT Filed: Mar. 14, 2014

(86) PCT No.: PCT/US2014/029304
§ 371 (c)(1),
(2) Date: Sep. 14, 2015

(87) PCT Pub. No.: WO2014/144761
PCT Pub. Date: Sep. 18, 2014

(65) Prior Publication Data
US 2016/0024524 A1 Jan. 28, 2016

Related U.S. Application Data

(60) Provisional application No. 61/799,647, filed on Mar. 15, 2013, provisional application No. 61/838,178, filed on Jun. 21, 2013, provisional application No. 61/838,148, filed on Jun. 21, 2013, provisional application No. 61/921,007, filed on Dec. 26, 2013.

(51) Int. Cl.
| | | |
|---|---|---|
| C07H 21/02 | (2006.01) |
| C12N 15/00 | (2006.01) |
| A61K 48/00 | (2006.01) |
| C12N 15/10 | (2006.01) |
| C12N 9/22 | (2006.01) |
| C12N 15/63 | (2006.01) |
| C12N 15/85 | (2006.01) |
| C07K 14/005 | (2006.01) |
| C07K 14/195 | (2006.01) |
| C12N 9/02 | (2006.01) |
| C12N 9/10 | (2006.01) |
| C12N 9/16 | (2006.01) |
| C12N 9/96 | (2006.01) |
| C12N 15/01 | (2006.01) |

(52) U.S. Cl.
CPC .......... *C12N 15/102* (2013.01); *C07K 14/005* (2013.01); *C07K 14/195* (2013.01); *C12N 9/0071* (2013.01); *C12N 9/1007* (2013.01); *C12N 9/16* (2013.01); *C12N 9/22* (2013.01); *C12N 9/96* (2013.01); *C12N 15/01* (2013.01); *C12N 15/63* (2013.01); *C12N 15/85* (2013.01); *C12Y 301/21004* (2013.01); *C07K 2319/00* (2013.01); *C07K 2319/01* (2013.01); *C12N 2710/00033* (2013.01); *C12N 2770/00033* (2013.01); *C12N 2800/80* (2013.01); *C12Y 114/11* (2013.01); *C12Y 201/01* (2013.01); *C12Y 301/00* (2013.01)

(58) Field of Classification Search
CPC .. C12N 15/113; C12N 2310/11; C12N 15/85; A61K 2300/00
See application file for complete search history.

(56) References Cited

U.S. PATENT DOCUMENTS

| | | | |
|---|---|---|---|
| 4,603,044 | A | 7/1986 | Geho et al. |
| 4,957,773 | A | 9/1990 | Spencer et al. |
| 5,436,150 | A | 7/1995 | Srinivasan |
| 6,007,988 | A | 12/1999 | Choo et al. |
| 6,013,453 | A | 1/2000 | Choo et al. |
| 6,503,717 | B2 | 1/2003 | Case et al. |
| 6,511,808 | B2 | 1/2003 | Wolffe et al. |
| 7,021,555 | B2 | 4/2006 | Bagnall |
| 7,220,719 | B2 | 5/2007 | Case |
| 7,914,796 | B2 | 3/2011 | Miller |
| 7,919,277 | B2 | 4/2011 | Russell et al. |
| 8,034,598 | B2 | 10/2011 | Miller |
| 8,071,370 | B2 | 12/2011 | Wolffe |
| 8,252,535 | B2 | 8/2012 | Biekle et al. |
| 8,282,920 | B2 | 10/2012 | Heo et al. |
| 8,361,725 | B2 | 1/2013 | Russell et al. |
| 8,697,359 | B1 | 4/2014 | Zhang |
| 8,771,986 | B2 | 7/2014 | Miller |
| 8,865,406 | B2 | 10/2014 | Zhang et al. |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

Addgene.org [Online]. CRISPR/Cas9 Guide on the web, Jan. 2016, [retrieved on Sep. 13, 2016]. Retrieved from the internet: URL<http://www.addgene.org/CRISPR/guide>/. 146 pages.
Extended European Search Report in European Application No. 14764159.1, dated Aug. 10, 2016, 7 pages.
Gaj et al., "ZFN, TALEN, and CRISPR/Cas-based methods for genome engineering, Trends in Biotechnology," Jul. 2013, 31(7): 397-405.
International Search Report and Written Opinion in International Application No. PCT/US2013/074736, dated Sep. 17, 2014, 4 pages.
International Search Report and Written Opinion in International Application No. PCT/US16/49147, dated Dec. 23, 2016, 12 pages.
International Search Report in International Application No. PCT/US2014/054291, dated Mar. 27, 2015, 6 pages.

(Continued)

*Primary Examiner* — Amy Bowman
(74) *Attorney, Agent, or Firm* — Fish & Richardson P.C.

(57) ABSTRACT

Methods for increasing specificity of RNA-guided genome editing, e.g., editing using CRISPR/Cas9 systems.

3 Claims, 17 Drawing Sheets

(56) References Cited

U.S. PATENT DOCUMENTS

| | | |
|---|---|---|
| 8,962,281 B2 | 2/2015 | Doyon |
| 8,993,233 B2 | 3/2015 | Zhang et al. |
| 9,023,649 B2 | 5/2015 | Mali et al. |
| 9,074,199 B1 | 7/2015 | Chavez et al. |
| 9,322,037 B2 | 4/2016 | Liu et al. |
| 2002/0160940 A1 | 10/2002 | Case et al. |
| 2002/0164575 A1 | 11/2002 | Case et al. |
| 2006/0199190 A1 | 9/2006 | Russell et al. |
| 2007/0020627 A1 | 1/2007 | Barbas, III |
| 2008/0124725 A1 | 5/2008 | Barrangou et al. |
| 2008/0193470 A1 | 8/2008 | Masignani et al. |
| 2010/0034924 A1 | 2/2010 | Fremaux et al. |
| 2010/0055793 A1 | 3/2010 | Chandrasegaran |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1 | 12/2013 | Duchateau |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1 | 1/2016 | Joung et al. |
| 2016/0010147 A1* | 1/2016 | Heron .................. C12N 9/14 435/6.1 |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024529 A1 | 1/2016 | Carstens et al. |
| 2016/0312198 A1 | 10/2016 | Joung et al. |
| 2016/0362688 A1 | 12/2016 | May et al. |

FOREIGN PATENT DOCUMENTS

| | | |
|---|---|---|
| CN | 103343120 | 10/2013 |
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |

(56) References Cited

FOREIGN PATENT DOCUMENTS

| WO | WO 2012/093833 | 7/2012 |
|---|---|---|
| WO | WO 2012/164565 | 12/2012 |
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/059255 | 4/2014 |
| WO | WO 2014/089290 | 6/2014 |
| WO | WO 2014/093655 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |

OTHER PUBLICATIONS

Invitation to Pay Additional Fees and, Where Applicable, Protest Fee in International application No. PCT/US2016/49147, dated Oct. 31, 2016, 2 pages.
Jinek et al., "Supplementary Materials for a Programmable Dual-RNA-Guided DNA Endonuclease in Adaptive Bacterial Immunity," Science Express, pp. 1-37 (2012).
Kleinstiver et al., "High-fidelity CR1SPR-Cas9 nucleases with no detectable genome-wide offtarget effects," Nature, Jan. 2016, 529: 490-495.
Office Action in Australian Application No. 2014227653, dated Nov. 18, 2016, 3 pages.
Slaymaker et al., "Rationally engineered Cas9 nucleases with improved specificity," Science, 2016, 351(6268): 84-88.
Al-Attar et al., "Clustered regularly interspaced short palindromic repeats (CRISPRs): the hallmark of an ingenious antiviral defence mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, 2008, 9:2.
Anders et al., "Structural basis of PAM-dependent target DNA recognition by the Cas9 endonuclease," Nature, 2014, 513:569-573.
Anonymous, "2013 Runners-Up. Genetic microsurgery for the masses," Science. Dec. 20, 2013;342(6165):1434-5.
Appela., "Non-natural nucleic acids for synthetic biology", Current Opinion in Chemical Biology, Dec. 2009,13(5-6): 687-696.
Arimondo et al., "Exploring the Cellular Activity of Camptothecin—Triple—Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
Auer et al., "Highly efficient CRISPR/Case9-mediated known-in in zebrafish by homology-independent DNA repair," Genome Res., 2014, 24:142-153.
Bae et al., "Cas-OFFinder: a fast and versatile algorithm that searches for potential off-target sites of Cas9 RNA-guided endonucleases," Bioinformatics, 2014, 30:1473-1475.

Bae et al., "Human zinc fingers as building blocks in the construction of artificial transcription factors," Nat Biotechnol., 21(3):275-280, Epub Feb. 18, 2003.
Barker et al., "Increased DNA microarray hybridization specificity using sscDNA targets," BMC Genomics, Apr. 2005, 6:57, 8 pages.
Baron-Benhamou et al., "Using the λN Peptide to Tether Proteins to RNAs," Methods Mole Biol., Jan. 2004, 257:135-153.
Barrangou & May, "Unraveling the potential of CRISPR-Cas9 for gene therapy," Expert Opin. Biol. Ther., 2015, 15:311-314.
Barrangou et al., "CRISPR Provides Acquired Resistance Against Viruses in Prokaryotes," Sci., 2007, 315:1709-1712.
Barrangou, "RNA-mediated programmable DNA cleavage," Nature Biotechnol., 2012, 30(9):836-838.
Bassett et al., "Highly efficient targeted mutagenesis of *Drosophila* with the CRISPR/Cas9 system," Cell Reports, 2013, 4:220-228.
Beerli and Barbas, "Engineering polydactyl zinc-finger transcription factors," Nat Biotechnol., 20(2):135-141, Feb. 2002.
Beerli et al., "Toward controlling gene expression at will: specific regulation of the erbB-2/HER-2 promoter by using polydactyl zinc finger proteins constructed from modular building blocks," PNAS USA, 1998, 95:14628-14633.
Belhaj et al., "Plant genome editing made easy: targeted mutagenesis in model and crop plants using the CRISPR/Cas system," Plant Methods, 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bikard et al., "Programmable repression and activation of bacterial gene expression using an engineered CRISPR-Cas system," Nucleic Acid Res., Jun. 2013 41(15):7429-7437.
Bitinaite et al., "FokI dimerization is required for DNA cleavage," Proc. Natl. Acad. Sci. USA, 1998, 95:10570-10575.
Blackburn et al., "The CRISPR System-Keeping Zebrafish Gene Targeting Fresh," Zebrafish, 2013, 10(1):116-118.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type III effectors," Science, Dec. 11, 2009;326(5959):1509-12.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Burgess, "A CRISPR genome-editing tool," Nature Reviews Genetics 14, 80-81 (Feb. 2013).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., 2002, 16:2583-2592.
Canadian Office Action in Canadian Application No. 2907198, dated Jul. 8, 2016, 4 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 1(3):1329-1341, 2006.
Carroll, "A CRISPR Approach to Gene Targeting," Molecular Therapy, 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., 2013, 31(9):807-809.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol. Ther., 2008, 16:1200-1207.

(56) References Cited

OTHER PUBLICATIONS

Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PLoS One, 7(9):E44852 pp. 1-11 (2012).
Chang et al., "Genome editing with RNA-guided Cas9 nuclease in zebrafish embryos," Cell Res., 2013, 23:465-472.
Chen & Zhao, "A highly sensitive selection method for directed evolution of homing endonucleases," Nucleic Acids Res., 2005, 33(18):e154.
Chen et al., "Cut Site Selection by the Two Nuclease Domains of the Cas9 RNA-guided Endonuclease," J Biol Chem. May 9, 2014; 289(19):13284-94.
Chen et al., "Dynamic imaging of genomic loci in living human cells by an optimized CRISPR/Cas system," Cell, 2013, 155(7):1479-1491.
Chen et al., "Efficient genome editing in Caenorhabditis elegans by CRISPR-targeted homologous recombination," Nucleic Acids Res., 2013, 41(20):e193, 6 pages.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Cheng et al., "Multiplexed activation of endogenous genes by CRISPR-on, an RNA-guided transcriptional activator system," Cell Res., Oct. 2013, 23(10):1163-71.
Chim et al., "Methylation profiling in multiple myeloma," Leuk. Res., Apr. 2004, 28:379-85.
Chiu et al., "Transgene-free genome editing in Caenorhabditis elegans using CRISPR-Cas," Genetics, Nov. 2013, 195(3):1167-71.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "Classification and evolution of type II CRISPR-Cas systems," Nucleic Acids Res. 2014;42(10):6091-105.
Chylinski et al., "The tracrRNA and Cas9 families of type II CRISPR-Cas immunity systems," RNA Biol., 2013, 10(5):726-737.
Clark-Curtiss and Curtiss, "[23] Analysis of recombinant DNA using *Escherichia coli* minicells," Methods in Enzymology, 1983, 101:347-362.
Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.
Cong et al., "Multiplex genome engineering using CRISPR/Cas systems," Science, 2013, 339:819-823 (Author Manuscript).
Conklin, "Sculpting genomes with a hammer and chisel," Nature Methods, 2013, 10(9):839-840.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Cradick et al., "CRISPR/Cas9 systems targeting beta-globin and CCR5 genes have substantial off-target activity," Nucleic Acids Res., 2013, 41(20):9584-92.
d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.

de Souza, "RNA-guided gene editing," Nat Methods, Mar. 2013, 10(3):189.
De Zhu, "The altered DNA methylation pattern and its implications in liver cancer," Cell. Res., 2005, 15:272-80.
Deltcheva et al., "CRISPR RNA maturation by trans-encoded small RNA and host factor RNAse III," Nature, 2011, 471(7340):602-607 (Author Manuscript).
Deveau et al., "Phage response to CRISPR-encoded resistance in *Streptococcus thermophilus*," J Bacteriol., Feb. 2008, 190(4):1390-400.
Dicarlo et al., "Genome engineering in *Saccharomyces cerevisiae* using CRISPR-Cas systems," Nucleic Acids Res., 2013, 41(7):4336-43.
Dickinson et al., "Engineering the Caenorhabditis elegans genome using Cas9-triggered homologous recombination," Nat Methods., Oct. 2013, 10(10):1028-34.
Ding et al., "Enhanced efficiency of human pluripotent stem cell genome editing through replacing TALENs with CRISPRs," Cell Stem Cell., Apr. 4, 2013, 12(4):393-4 (Author Manuscript).
Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-Scel," J. Am. Chem. Soc., 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Term Engraftment After Autologous Transplantation," Blood, Jun. 1995, 85:3048-3057.
Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, 6(4):451-464, Apr. 15, 1998.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Esvelt et al., "Orthogonal Cas9 proteins for RNA-guided gene regulation and editing," Nat Methods, Nov. 2013, 10(11):1116-21.
European Partial Supplementary Search Report in European Application No. 14764117.9, dated Aug. 11, 2016, 7 pages.
European Search Report in European Application No. 14763916.5, dated Jul. 27, 2016, 10 pages.
Fisher et al., "A scalable, fully automated process for construction of sequence-ready human exome targeted capture libraries," Genome Biol., 2011, 12-R1.
Fonfara et al., "Phylogeny of Cas9 determines functional exchangeability of dual-RNA and Cas9 among orthologous type II CRISPR-Cas systems." Nucleic Acids Res., Feb. 2014, 42(4):2577-90.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Friedland et al., "Heritable genome editing in C. elegans via a CRISPR-Cas9 system," Nature Methods 10(8): 741-743, 2013 (Author Manuscript).

(56) References Cited

OTHER PUBLICATIONS

Fu et al, Targeted genome editing in human cells using CRISPR/Cas nucleases and truncated guide RNAs, Methods in Enzymology, 546: 21-45.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat. Biotechnol., 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 4, 2010, 468(7320):67-71.
Gasiunas and Siksnys,"RNA-dependent DNA endonuclease Cas9 of the CRISPR system: Holy Grail of genome editing?" Trends Microbiol., 2013, 21(11):562-567.
Gasiunas,"Cas9-crRNA ribonucleoprotein complex mediates specific DNA cleavage for adaptive immunity in bacteria," Proc Natl Acad Sci U S A, Sep. 25. 2012, 109(39):E2579-86.
Geibler et al., "Transcriptional Activators of Human Genes with Programmable DNA-Specificity," PLoS One, 6:e19509 (2011).
Gilbert et al., "CRISPR-mediated modular RNA-guided regulation of transcription in eukaryotes," Cell, 2013, 154(2):442-51.
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guilinger et al., "Fusion of catalytically inactive Cas9 to FokI nuclease improves the specificity of genome modification," Nat Biotechnol., Apr. 2014, 32(6):577-583.
Guo el al., "Hydroxylation of 5-Methylcytosine by TET1 Promotes Active DNA Demethylation in the Adult Brain ," Cell, 145:423-434 (2011).
Haft et al., "A Guild of 45 CRISPR-Associated (Cas) Protein Families and multiple CRISPER/cas Subtypes Exist in Prokaryotic Genomes," PLOS, 2005, 1(6):0474-0483.
Hale et al., "Essential features and rational design of CRISPR RNAs that function with the Case RAMP modlule complex to cleave RNAs," Mol Cell., 2012, 45(3):292-302 (Author Manuscript).
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structures pecific mechanisms to recognize and process crRNAs," Thesis. May 8, 2012 (Aug. 5, 2012), University of California, Berkeley, pp. 1-120. Retrieved from the Internet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, 333:1303-1307 (2011).
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Horvath et al., "Diversity, activity, and evolution of CRISPR loci in *Streptococcus thermophilus,* " J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Huang et al., "Heritable gene targeting in zebrafish using customized TALENs," Nat. Biotechnol., 29:699-700 (2011).
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.
International Preliminary Report on Patentability in International Application No. PCT/US2013/043075, dated Dec. 2, 2014, 7 pages.
International Preliminary Report on Patentability in International Application No. PCT/US2014/027335, dated Sep. 15, 2015, 10 pages.
International Preliminary Report on Patentability in International Application No. PCT/US2014/028630, dated Sep. 15, 2015, 8 pages.
International Preliminary Report on Patentability in International Application No. PCT/US2014/029068, dated Sep. 15, 2015, 10 pages.
International Preliminary Report on Patentability in International Application No. PCT/US2014/029304, dated Sep. 22, 2015, 12 pages.
International Preliminary Report on Patentability in International Application No. PCT/US2014/056416, dated Jun. 28, 2016, 7 pages.
International Search Report and Written Opinion in International Application No. PCT/US2013/043075, dated Sep. 26, 2013, 10 pages.
International Search Report and Written Opinion in International Application No. PCT/US2014/027335, dated Jul. 16, 2014, 13 pages.
International Search Report and Written Opinion in International Application No. PCT/US2014/028630, dated Jul. 24, 2014, 9 pages.
International Search Report and Written Opinion in International Application No. PCT/US2014/029068, dated Nov. 5, 2014, 15 pages.
International Search Report and Written Opinion in International Application No. PCT/US2014/029304, dated Nov. 14, 2014, 17 pages.

(56) References Cited

OTHER PUBLICATIONS

International Search Report and Written Opinion in International Application No. PCT/US2014/035162, dated Oct. 14, 2014, 10 pages.
International Search Report and Written Opinion in International Application No. PCT/US2014/056416, dated Apr. 3, 2015, 11 pages.
Invitation to Pay Additional Fees and, Where Applicable, Protest Fee in International Application No. PCT/US2014/029068, dated Aug. 20, 2014, 3 pages.
Invitation to Pay Additional Fees and, Where Applicable, Protest Fee in International Application No. PCT/US2014/029304, dated Jul. 30, 2014, 3 pages.
Isalan et al., "A rapid, generally applicable method to engineer zinc fingers illustrated by targeting the HIV-1 promoter," Nat. Biotechnol., 19(7):656-660, Jul. 2001.
Ishino et al., "Nucleotide sequence of the iap gene, responsible for alkaline phosphatase isozyme conversion in *Escherichia coli,* and identification of the gene product," J Bacteriol., Dec. 1987, 169(12):5429-33.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 1, 2009, 8(11):1698-710.
Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL<ftp://ftp.ncbi.nih.gov/pub/aravind/DONS/supplementary_material_DONS.html>.
Jamieson et al., "In vitro selection of zinc fingers with altered DNA-binding specificity," Biochemistry, 33(19):5689-5695, May 17, 1994.
Jansen et al., "Identification of genes that are associated with DNA repeats in prokaryotes," Mol Microbiol., Mar. 2002, 43(6):1565-75.
Jiang et al., "CRISPR-assisted editing of bacterial genomes," Nat Biotechnol., 2013, 31:233-239 (Author Manuscript).
Jiang et al., "Structural Biology. A Cas9-guide RNA complex preorganized for target DNA recognition," Science, Jun. 2015, 348:1477-1481.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 Endonucleases Reveal RNA-Mediated Conformational Activation," Science. Mar. 14, 2014; 343(6176):1247997.
Josephs et al., "Structure and specificity of the RNA-guided endonuclease Cas9 during DNA interrogation, target binding and cleavage," Nucleic Acids Res., Sep. 2015, 43:8924-8941.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases","Nat. Methods, Jan. 2010, 7:91-92.
Karkare and Bhatnagar, "Promising nucleic acid analogs and mimics: characteristic features and applications of PNA, LNA, and morpholino", Applied Microbiology and Biotechnology, May 2006, 71(5): 575-586.
Karmirantzou and Harnodrakas, "A Web-based classification system of DNA-binding protein families," Protein Eng. 14(7):465-472, Jul. 2001.
Karvelis et al., "crRNA and tracrRNA guide Cas9-mediated DNA interference in *Streptococcus thennophilus,* " RNA Biol., 2013, 10(5):841-851.

Katic and Großhans, "Targeted heritable mutation and gene conversion by Cas9-CRISPR in Caenorhabditis elegans," Genetics, Nov. 2013, 195(3):1173-6.
Kearns et al., "Recombinant adeno-associated virus (AAV-CFTR) vectors do not integrate in a site-specific fashion in an immortalized epithelial cell line," Gene Ther., Sep. 1996, 9:748-55.
Keryer-Bibens et al., "Tethering of proteins to RNAs by bacteriophage proteins," Biol Cell, 2008, 100:125-138.
Kiani et al., "Cas9 gRNA engineering for genome editing, activation and repression," Nat. Methods, 2015, 12:1051-1054.
Kim and Kim, "A guide to genome engineering with programmable nucleases," Nature Rev Genetics 15, 321-334 (2014).
Kim et al., "Highly efficient RNA-guided genome editing in human cells via delivery of purified Cas9 ribonucleoproteins," Genome Res. Jun. 2014; 24(6):1012-9.
Kim et al., "Targeted genome editing in human cells with zinc finger nucleases constructed via modular assembly," Genome Res., 19(7):1279-1288, Epub May 21, 2009.
Kim et al., "Genome editing with modularly assembled zinc-finger nucleases," Nat. Methods, 7(2):91-92, Feb. 2010.
Kleinstiver et al., "A unified genetic, computational and experimental framework identifies functionally relevant residues of the homing endonuclease I-BmoI," Nucleic Acids Res., 2010, 38:2411-2427.
Kleinstiver et al., "Engineered CRISPR-Cas9 nucleases with altered PAM specificities," Nature, Jul. 2015, 523(7561):481-5.
Klimpel et al., "Anthrax toxin protective antigen is activated by a cell surface protease with the sequence specificity and catalytic properties of furin," PNAS, Nov. 1992, 89:10277-81.
Lo et al., "Precise and Heritable Genome Editing in Evolutionarily Diverse Nematodes Using TALENs and CRISPR/Cas9 to Engineer Insertions and Delections," Genetics, 2013, 195:331-348.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila,* " Genetics, Nov. 2013, 195(3):715-21.
Konermann et al., "Optical control of mammalian endogenous transcription and epigenetic states," Nature. Aug. 22 2013; 500(7463):472-6. (Author Manuscript).
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lea et al., "Aberrant p16 methylation is a biomarker for tobacco exposure in cervical squamous cell carcinogenesis," Am. J. Obstet. Gynecol., 2004, 190:674-9.
Lee et al., "Three-dimensional solution structure of a single zinc finger DNA-binding domain," Science., 245(4918):635-637, Aug. 11, 1989.
Li et al., "DNA methylation in prostate cancer," Biochim. Biophys. Acta., Sep. 2004, 1704:87-102.
Li et al., "Heritable gene targeting in the mouse and rat using a CRISPR-Cas system," Nat Biotechnol, Aug. 2013, 31(8):681-3.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.
Li et al., "Simultaneous generation and germline transmission of multiple gene mutations in rat using CRISPR-Cas systems," Nat Biotechnol., Aug. 2013, 31(8):684-6.

(56) References Cited

OTHER PUBLICATIONS

Li et al., "TAL nucleases (TALNs): hybrid proteins composed of TAL effectors and FokI DNA-cleavage domain," Nucleic Acids Res., 2011, 39(1): 359-372.
Lin et al., "CRISPR/Cas9 systems have off-target activity with insertions or deletions between target DNA and guide RNA sequences," Nucleic Acids Res., 2014, 42:7473-7485.
Lin et al., "iDNA-Prot: identification of DNA binding proteins using random forest with grey model," PLoS One., 6(9):e24756, Epub Sep. 15, 2011.
Liu et al., "Regulation of an Endogenous Locus Using a Panel of Designed Zinc Finger Proteins Targeted to Accessible Chromatin Regions," J. Biol. Chem., Apr. 2001, 276(14):11323-34.
Liu et al., "Validated zinc finger protein designs for all 16 GNN DNA triplet targets," J. Biol. Chem., 277(6):3850-3856, Epub Nov. 28, 2001.
Lund et al., "DNA Methylation Polymorphisms Precede Any Histological Sign of Atherosclerosis in Mice Lacking Apolipoprotein E," J. Biol. Chem., Jul. 2004, 279:29147-54.
Mabaera et al., "Developmental- and differentiation-specific patterns of human γ- and β-globin promoter DNA methylation," Blood, 110(4):1343-52 (2007).
Maeder et al., "CRISPR RNA-guided activation of endogenous human genes," Nat Methods, 2013, 10:977-979 (Author Manuscript).
Maeder et al., "Rapid 'open-source' engineering of customized zinc-finger nucleases for highly efficient gene modification," Mol Cell, 2008, 31(2):294-301.
Maeder et al., "Robust, synergistic regulation of human gene expression using TALE activators," Nat. Methods, 2013, 10:243-245.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock in and Sequence Modulation Mediated by a Psoralen-linked Triplex-forming Oligonucleotide," J Biol Chem., 283(17):11244-52 (2008).
Makarova et al., "A putative RNA-interference-based immune system in prokaryotes: computational analysis of the predicted enzymatic machinery, functional analogies with eukaryotic RNAi, and hypothetical mechanisms of action," Biol. Direct, 2006, 1:7, 26 pages.
Makarova et al., "Evolution and classification of the CRISPR-Cas systems," Nat. Rev. Microbiol., 2011, 9(6):467-77 (Author Manuscript).
Makarova et al., "Unification of Cas protein families and a simple scenario for the origin and evolution of CRISPR-Cas systems," Biol. Direct, 2011, 6:38, 27 pages.
Malech et al., "Prolonged production of NADPH oxidase-corrected granulocytes after gene therapy of chronic granulomatous disease," PNAS, Oct. 1997, 94:12133-38.
Mali et al., "Cas9 as a versatile tool for engineering biology," Nature Methods, 2013, 10(10):957-963.
Mali et al., "CAS9 transcriptional activators for target specificity screening and paired nickases for cooperative genome engineering," Nat Biotechnol., 2013, 31:833-838.
Mali et al., "RNA-guided human genome engineering via Cas9," Science, Feb. 2013, 339:823-826 (Author Manuscript).
Mancini et al. "CpG methylation within the 5' regulatory region of the BRCA1 gene is tumor specific and includes a putative CREB binding site," Oncogene, 1998, 16:1161-9.
Mandell and Barbas et al., "Zinc Finger Tools: custom DNA-binding domains for transcription factors and nucleases," Nucleic Acids Res., 34(Web Sewer issue):W516-W523, Jul. 1, 2006.
Marraffini and Sontheimer, "CRISPR Interference Limits Horizontal Gene Transfer in Staphylococci by Targeting DNA," Sci., 2008, 322(5909):1843-1845.
Marraffini and Sontheimer, "Self vs. non-self discrimination during CRISPR RNA-directed immunity," Nature, 2010, 463(7280):568-571 (Author Manuscript).
Mashiko et al., "Generation of mutant mice by pronuclear injection of circular plasmid expressing Cas9 and single guided RNA," Sci Reports, 2013, 3(3355):1-6.
McGarty, "CRISPRs and Cancer," White Paper No. 111, Apr. 2014, 22 pages.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nature Biotechnology, Feb. 2011, 29:143-148.
Miller et al., "An improved zinc-finger nuclease architecture for highly specific genome editing," Nat Biotechnol., 2007, 25:778-785.
Miller et al., "Repetitive zinc-binding domains in the protein transcription factor IIIA from Xenopus oocytes," EMBO J., 4(6):1609-1614, Jun. 1985.
Miyazaki et al., "Expression vector system based on the chicken beta-actin promoter directs efficient production of interleukin-5," Gene, Jul. 1989, 79(2):269-77.
Mojica et al., "Biological significance of a family of regularly spaced repeats in the genomes of Archaea, Bacteria and mitochondria," Mol Microbiol., Apr. 2000, 36(1):244-6.
Mojica et al., "Short motif sequences determine the targets of the prokaryotic CRISPR defense system," Microbiology, 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Nati Acad Sci U S A., 107(50):21617-21622, Epub Nov. 24, 2010.
Morbitzer et al., "Assembly of custom TALE-type DNA binding domains by modular cloning," Nucl Acids Res., 39:5790-5799 (2011).
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, 326(5959):1501, Dec. 11, 2009.
Mussolino and Cathomen, "RNA guides genome engineering," Nat Biotechnol., 2013, 31(3):208-209.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nishimasu et al., "Crystal structure of Cas9 in complex with guide RNA and target DNA," Cell, 2014, 156:935-949.
Nissim et al., "Multiplexed and Programmable Regulation of Gene Networks with an Integrated RNA and CRISPR/Cas Toolkit in Human Cells," Molecular Cell, May 2014, 54:698-710.
Niu et al., "Generation of gene-modified cynomolgus monkey via Cas9/RNA-mediated gene targeting in one-cell embryos," Cell, 2014, 156:836-843.
Niwa et al., "Efficient selection for high-expression transfectants with a novel eukaryotic vector," Gene, 199L 108(2):193-9.

(56) References Cited

OTHER PUBLICATIONS

Novak et al., "Functional Characterization of Protease-treated Bacillus anthracis Protective Antigen," J. Biol. Chem., Aug. 1992, 267:17186-93.
Oligino et al., "Drug inducible transgene expression in brain using a herpes simplex virus vector," Gene Ther., 1998, 5:491-496.
Palva et al., "Secretion of interferon by Bacillus subtilis," Gene, 1983, 22:229-235.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, 2011, 8:765-770 (Author Manuscript).
Pavletich and Pabo, "Zinc finger-DNA recognition: crystal structure of a Zif268-DNA complex at 2.1 A," Science, 252(5007):809-817, May 10, 1991.
Perelle et al., "Characterization of Clostridium perfringens Iota-Toxin Genes and Expression in *Escherichia coli,*" Infect. Immun., Dec. 1993, 61:5147-56.
Perez et al., "Establishment of HIV-1 resistance in CD4+ T cells by genome editing using zinc-finger nucleases," Nat Biotechnol., 2008, 26:808-816 (Author Manuscript).
Perez-Pinera et al., "RNA-guided gene activation by CRISPR-Case9-based transcription factors," Nat Methods, 2013, 10(10):973-976 (Author Manuscript).
Pingoud and Silva, "Precision genome surgery," Nat Biotechnol., 25(7):743-744, Jul. 2007.
Puchta and Fauser et al., "Synthetic nucleases for genome engineering in plants: prospects for a bright future," Plant J. Jun. 2014; 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.
Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14:107, 4 pages.
Ramirez et al., "Unexpected failure rates for modular assembly of engineered zinc fingers," Nat Methods., 5(5):374-375, May 2008.
Ran et al., "Double nicking by RNA-guided CRISPR Cas9 for enhanced genome editing specificity," Cell, 2013, 154:1380-1389.
Ran et al., "Genome engineering using the CRISPR-Cas9 system," Nature Protocols, 2013, 8(11):2281-2308.
Ran et al., "In vivo genome editing using *Staphylococcus aureus* Cas9," Nature, 2015, 520:186-191.
Rebar and Pabo, "Zinc finger phage: affinity selection of fingers with new DNA-binding specificities," Science, 263(5147):671-673, Feb. 4, 1994.
Ren et al., "Optimized gene editing technology for *Drosophila melanogaster* using germ line-specific Cas9," Proc Natl Acad Sci U S A, Nov. 19, 2013, 110(47):19012-7.
Rendahl et al., "Regulation of gene expression in vivo following transduction by two separate rAAV vectors," Nat. Biotechnol., Aug. 1998, 16:757-761.
Reyon et al., "FLASH assembly of TALENs for high-throughput genome editing," Nat Biotech, 2012, 30:460-465 (Author Manuscript).
Ro et al., "Adenovirus-based short hairpin RNA vectors containing an EGFP marker and mouse U6, human H1, or human U6 promoter," BioTechniques, 2005, 38(4):625-627.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Rothman, "Mechanisms of intracellular protein transport," Nature, 372(6501):55-63, Nov. 3, 1994.
Rusk, "CRISPRs and epigenome editing," Nature Methods, 2014, 11(1):28.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res., 2013, 41:e181.
Sander et al., "ZiFiT (Zinc Finger Targeter): an updated zinc finger engineering tool," Nucleic Acids Res., 2010, 38:W462-468.
Sander et al., "Zinc Finger Targeter (ZiFiT): an engineered zinc finger/target site design tool," Nucleic Acids Res., 2007, 35:W599-605.
Sander et al., "Targeted gene disruption in somatic zebrafish cells using engineered TALENs," Nat. Biotechnol., 29:697-698 (2011).
Sanjana et al., A transcription activator-like effector toolbox for genome engineering, Nature Protocols, 2012, 7:171-192.
Sapranauskas et al., "The *Streptococcus thennophilus* CRISPR/Cas system provides immunity in *Escherichia coli*," Nucleic Acids Res., 2011, 39(21):9275-9282.
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).
Schwank et al., "Functional repair of CFTR by CRISPR/Cas9 in intestinal stem cell organoids of cystic fibrosis patients," Cell Stem Cell, Dec. 5, 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Shah et al., "Protospacer recognition motifs," RNA Biol., 2013, 10:891-899.
Sharma, "Schizophrenia, epigenetics and ligand-activated nuclear receptors: a framework for chromatin therapeutics," Schizophr. Res., Jan. 2005, 72:79-90.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Shmakov et al., "Discovery and Functional Characterization of Diverse Class 2 CRISPR-Cas Systems," Molecular Cell, 2015 60:385-397.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):353 I-8 (2008).
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR—Cas9" Nature, 2015, 527:110-113.
Sternberg et al., "DNA interrogation by the CRISPR RNA-guided endonuclease Cas9," Nature, 2014, 507:62-67.
Sternberg et al., "Mechanism of substrate selection by a highly specific CRISPR endoribonuclease," RNA, 2012, 18:661-672.

(56) References Cited

OTHER PUBLICATIONS

Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Swarts el al., "CRISPR Interference Directed Strand Specific Spacer Acquisition," PLOS, 2012, 7(4):1-7.
Szczepek et al., "Structure-based redesign of the dimerization interface reduces the toxicity of zinc-finger nucleases," Nat Biotechnol., 2007, 25:786-793.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, 324:930-935 (2009).
Tan et al., "Efficient nonmeiotic allele introgression in livestock using custom endonucleases," Proc Natl Acad Sci U S A, Oct. 8, 2013, 110(41):16526-31.
Tan et al., "Zinc-finger protein-targeted gene regulation: genomewide single-gene specificity," Proc Natl Acad Sci U S A., 100(21):11997-2002, Epub Sep. 26, 2003.
Terns and Terns, "CRISPR-based adaptive immune systems," Curr Opin Microbiol., 2011, 14:321-327.
Tesson et al., "Knockout rats generated by embryo microinjection of TALENs," Nat. Biotechnol., 29:695-696 (2011).
Tjong and Zhou, "DISPLAR: an accurate method for predicting DNA-binding sites on protein surfaces," Nucleic Acids Res., 35(5):1465-1477, Epub Feb. 6, 2007.
Tsai et al., "Dimeric CRISPR RNA-guided FokI nucleases for highly specific genome editing," Nat Biotechnol., Apr. 2014, 32(6):569-576.
Tsai et al., "GUIDE-Seq enables genome-wide profiling of off-target cleavage by CRISPR-Cas nucleases," Nat Biotechnol, Feb. 2015, 33:187-497.
Tzur et al., "Heritable Custom Genomic Modifications in Caenorhabditis elegans via a CRISPR-Cas9 System," Genetics, 2013, 195:1181-1185.
Uhlmann et al., "Distinct methylation profiles of glioma subtypes," Int. J. Cancer, Aug. 2003, 106:52-9.
U.S. Final Office Action in U.S. Appl. No. 13/838,520, dated Jul. 15, 2015, 35 pages.
U.S. Final Office Action in U.S. Appl. No. 14/211,117, dated Jun. 30, 2016, 26 pages.
U.S. Non-Final Office Action in U.S. Appl. No. 14/211,117, dated Sep. 8, 2015, 20 pages.
U.S. Non-Final Office Action in U.S. Appl. No. 14/213,479, dated Dec. 9, 2015, 39 pages.
U.S. Non-Final Office Action in U.S. Appl. No. 14/213,723, dated Mar. 2, 2016, 39 pages.
U.S. Non-Final Office Action in U.S. Appl. No. 13/838,520, dated Oct. 6, 2014, 38 pages.
van der Oost et al., "Unravelling the Structural and Mechanistic Basis of CRISPR-Cas Systems," Nature Reviews Microbiology, 2014, 12:479-492.
Ventura et al., "Cre-lox-regulated conditional RNA interference from transgenes," PNAS, Jul. 2004, 101:10380-10385.
Waaigers et al., "CRISPR/Cas9-Targeted Mutagenesis in Caenorhabditis elegans," Genetics, 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS One, 6:e19722 (2011).
Widschwendter and Jones, "DNA methylation and breast carcinogenesis," Oncogene, Aug. 2002, 21:5462-82.
Wiedenheft, "RNA-guided genetic silencing systems in bacteria and archaea," Nature, 2012, 482:331-338.
Wolfe et al., "DNA recognition by Cys2His2 zinc finger proteins," Annu Rev Biophys Biomol Struct. 29:183-212 (2000).
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Correction of a genetic disease in mouse via use of CRISPR-Cas9," Cell Stem Cell., Dec. 5, 2013, 13(6):659-62.
Wu et al., "Custom-designed zinc finger nucleases: what is next?" Cell Mol Life Sci., 64(22):2933-2944, Nov. 2007.
Wu et al "Genome-wide binding of the CRISPR endonuclease Cas9 in mammalian cells," Nat Biotechnol. Jul. 2014; 32(7):670-6.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "One-step generation of mice carrying reporter and conditional alleles by CRISPR/Cas-mediated genome engineering," Cell, Sep. 12, 2013; 154(6):1370-9.
Yang et al., "Optimization of scarless human stem cell genome editing," Nucleic Acids Res., 2013, 41:9049-9061.
Yin et al., "Genome editing with Cas9 in adult mice corrects a disease mutation and phenotype," Nature Biotechnology 32, 551-553 (2014).
Zetsche et al., "Cpf1 Is a Single RNA-Guided Endonuclease of a Class 2 CRISPR-Cas System," Cell, 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhou et al., "High-throughput screening of a CRISPR/Cas9 library for functional genomics in human cells," Nature. May 22, 2014; 509(7501):487-91.
Zitzewitz et al., "Probing the folding mechanism of a leucine zipper peptide by stopped-flA4:A48ism spectroscopy," Biochemistry, 34(39):12812-12819, Oct. 3, 1995.
Office Action in U.S. Appl. No. 14/775,930, dated Feb. 27, 2017, 55 pages.
Office Action in European Application No. 14763916.5, dated Mar. 27, 2017, 6 pages.
Chinese Office Action in Application No. 201480026113.4, dated May 31, 2017, 21 pages. (with English translation).
Extended European Search Report in Application No. 14875819.6, dated Jun. 8, 2017, 11 pages.

\* cited by examiner

EMX1 truncated gRNA

| SEQ ID NO | Sequence | Indel |
|---|---|---|
| SEQ ID NO: 75 | GAAGCTGGAGGAGGAAGGGCCTGAGTCCGAGCAGAAGAAGAAgGGCTCCCATCACATCAACCGGTGG | wild-type x24 |
| SEQ ID NO: 76 | GAAGCTGGAGGAGGA | Δ365 |
| SEQ ID NO: 77 | TCAACCGGTGG | Δ181 |
| SEQ ID NO: 78 | GAAGCTGGAGGAGGAAGG | Δ138 |
| | | Δ126 |
| SEQ ID NO: 79 | GGGCTCCCATCACATCAACCGGTGG | Δ114 |
| SEQ ID NO: 80 | GAAGCTGGAGGAGGAAGGGCCTGA | Δ101 |
| SEQ ID NO: 81 | GAAGCTGGAGGA ... GG | Δ53 |
| SEQ ID NO: 82 | GAAGCTGGAGGAGGAAGGG ... CCCATCACATCAACCGGTGG | Δ28 |
| SEQ ID NO: 83 | GAAGCTGGAGGAGGAAGGGC ... TCGCACACATCAACCGGTGG | Δ27 |
| SEQ ID NO: 84 | GAAGCTGGAGGAGGAAGGGC ... CTTCCATCACATCAACCGGTGG | Δ25 |
| SEQ ID NO: 85 | GAAGCTGGAGGAGGAAGGGCCTGAG ... TCCCATCACATCAACCGGTGG | Δ21 x2 |
| SEQ ID NO: 86 | GAAGCTGGAGGAGGAAGGGCCTGAGTCCGAG ... TCCCATCACATCAACCGGTGG | Δ15 |
| SEQ ID NO: 87 | GAAGCTGGAGGAGGAAGGGCCTGAGTCCGAGCAGAAG ... TCCCATCACATCAACCGGTGG | Δ9 |
| SEQ ID NO: 88 | GAAGCTGGAGGAGGAAGGGCCTGAGTCCTGCCGTTTGTAG ... CCATCACATCAACCGGTGG | Δ8 |
| SEQ ID NO: 89 | GAAGCTGGAGGAGGAAGGGCCTGAGTCCGAGCAGAAGA ... GCTCCCATCACATCAACCGGTGG | Δ6 |
| SEQ ID NO: 90 | GAAGCTGGAGGAGGAAGGGCCTGAGTCCGAGCAGAAGAA ... CTCCCATCACATCAACCGGTGG | Δ6 |
| SEQ ID NO: 91 | GAAGCTGGAGGAGGAAGGGCCTGAGTCCGAGC ... AGAAGAAGGGCTCCCATCACATCAACCGGTGG | Δ3 x3 |
| SEQ ID NO: 92 | GAAGCTGGAGGAGGAAGGGCCTGAGTCCGAGCAGAAGA ... AAGGGCTCCCATCACATCAACCGGTGG | Δ2 |
| SEQ ID NO: 93 | GAAGCTGGAGGAGGAAGGGCCTGAGTCCGAGCAGAAGAACAGAAGGGCTCCCATCACATCAACCGGT | +2 |

EMX1 full-length gRNA

| SEQ ID NO | Sequence | Indel |
|---|---|---|
| SEQ ID NO: 94 | GAAGCTGGAGGAGGAAGGGCCTGAGTCCGAGCAGAAGAAGAAgGGCTCCCATCACATCAACCGGTGG | wild-type x35 |
| SEQ ID NO: 95 | GAAGCTGGAGGAGGAAGGGCCTGAGTCCGAG | Δ202 |
| | | Δ115 |
| | GAA | Δ94 |
| | | Δ76 |
| SEQ ID NO: 96 | GAAGCTGGAGG | Δ72 |
| SEQ ID NO: 97 | GAAGCTGGA ... GG | Δ56 |
| SEQ ID NO: 98 | GAAGCTGGAGGAGGAAGGGCCTGA ... GTGG | Δ39 |
| SEQ ID NO: 99 | GAAGCTGGAGGAG ... GAAGGGCTCCCATCACATCAACCGGTGG | Δ26 x2 |
| SEQ ID NO: 100 | GAAGCTGGAGGAGGAAGGGCCTGAGT ... CCATCACATCAACCGGTGG | Δ22 |
| SEQ ID NO: 101 | GAAGCTGGAGGAGGAAGGGCCTGAG ... TCCCATCACATCAACCGGTGG | Δ21 x3 |
| SEQ ID NO: 102 | GAAGCTGGAGGAGGAAGGGCCTGAGTCCGAG ... CATCACATCAACCGGTGG | Δ18 |
| SEQ ID NO: 103 | GAAGCTGGAGGAGGAAGGGCCTGAGTCCGA ... GCTCCCATCACATCAACCGGTGG | Δ14 |
| SEQ ID NO: 104 | GAAGCTGGAGGAGGAAGGGCCTGAGTCCGAGC ... AGAAGAAGGGCTCCCATCACATCAACCGGTGG | Δ6 x3 |
| SEQ ID NO: 105 | GAAGCTGGAGGAGGAAGGGCCTGAGTCCGAGC ... AGAAGAAGGGCTCCCATCACATCAACCGGTGG | Δ3 x3 |
| SEQ ID NO: 106 | GAAGCTGGAGGAGGAAGGGCCTGAGTCCGAGCAGA ... AAGAAGGGCTCCCATCACATCAACCGGTGG | Δ2 x2 |
| SEQ ID NO: 107 | GAAGCTGGAGGAGGAAGGGCCTGAGTCCGAGCAGAAGACAGAAGGGCTCCCATCACATCAACCGGT | +2 |

FIG. 3C

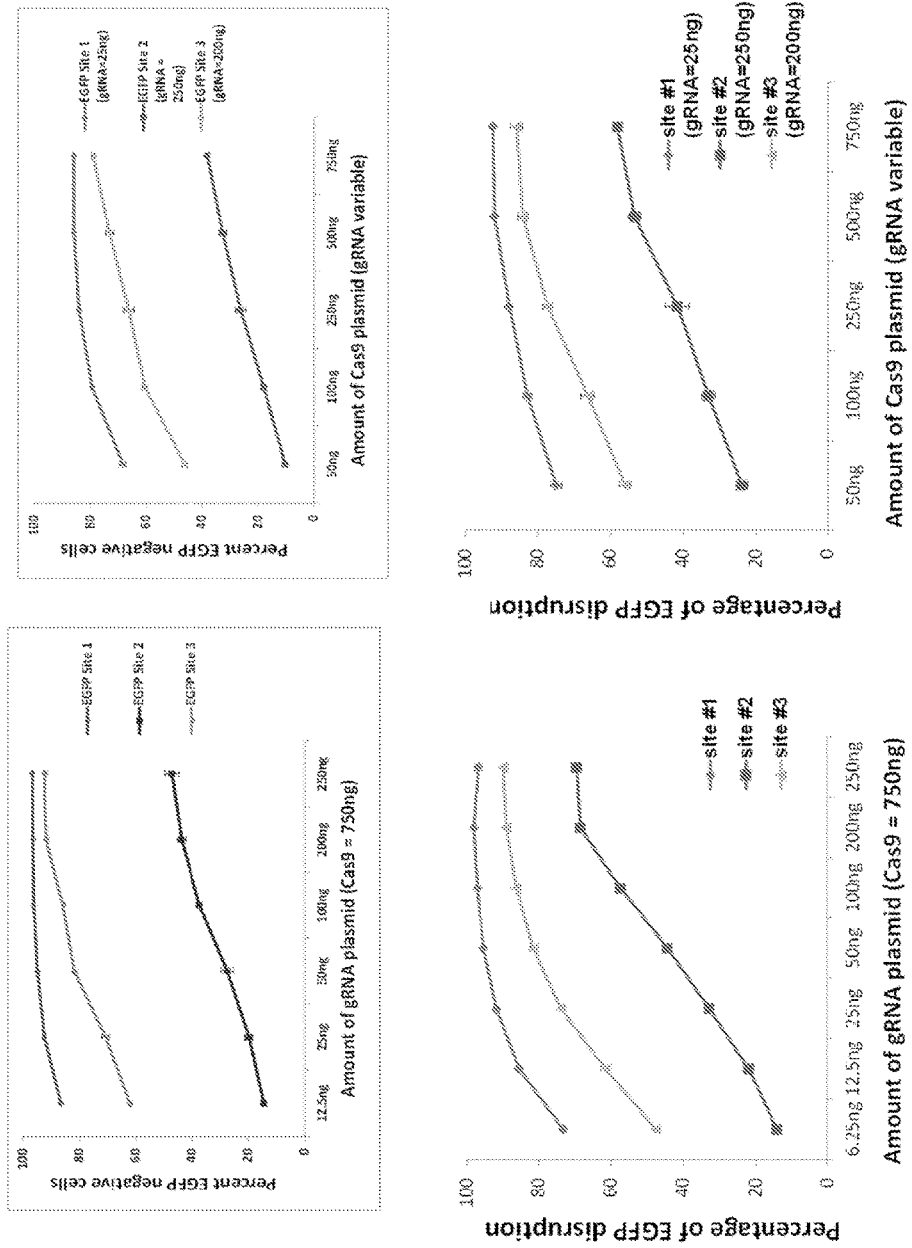

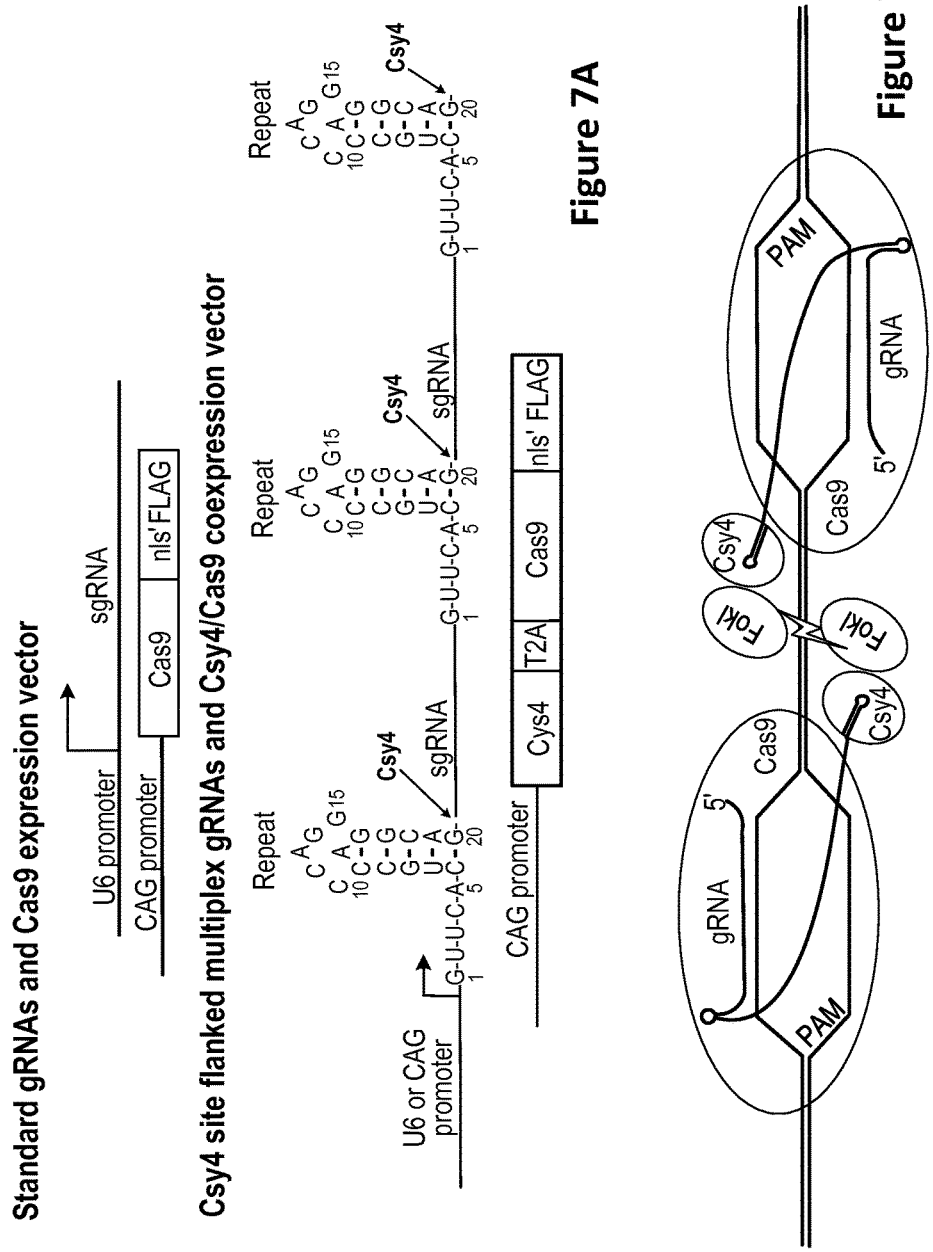

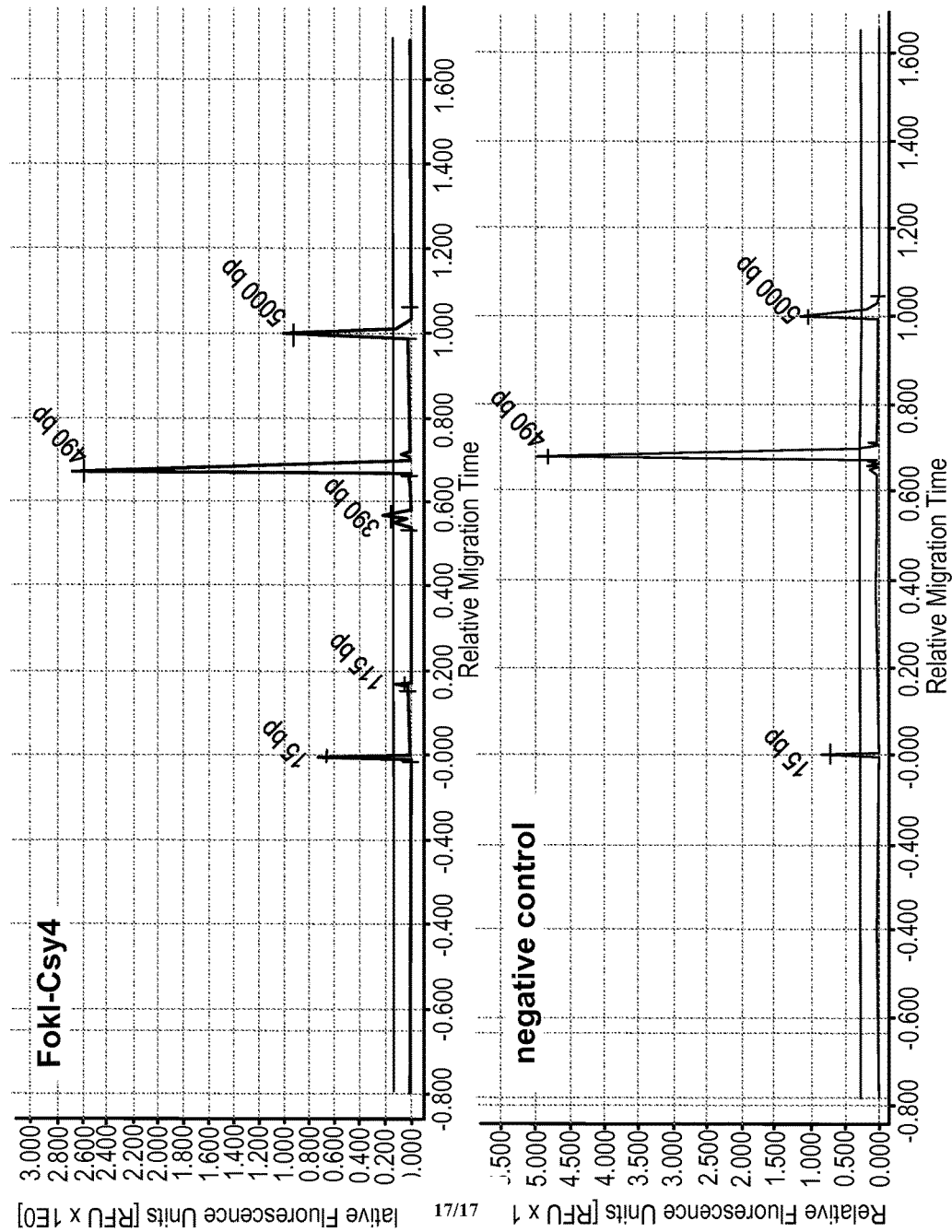

SEQUENCE LISTING

```
<160> NUMBER OF SEQ ID NOS: 115

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      binding site oligonucleotide

<400> SEQUENCE: 1
gggcacgggc agcttgccgg tgg                                           23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      binding site oligonucleotide

<400> SEQUENCE: 2
gatgccgttc ttctgcttgt cgg                                           23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      binding site oligonucleotide

<400> SEQUENCE: 3
ggtggtgcag atgaacttca ggg                                           23

<210> SEQ ID NO 4
<211> LENGTH: 242
<212> TYPE: RNA
<213> ORGANISM: Artificial Sequence
<220> FEATURE:
```

```
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (43)..(242)
<223> OTHER INFORMATION: a, c, u, g, unknown or other and this region
      may encompass 0-200 nucleotides
<220> FEATURE:
<221> NAME/KEY: misc_feature
<222> LOCATION: (43)..(242)
<223> OTHER INFORMATION: n is a, c, g, or u

<400> SEQUENCE: 4
nnnnnnnnnn nnnnnnnnnn guuuuagagc uaugcuguuu ugnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240 nn                                                                   242

<210> SEQ ID NO 5
<211> LENGTH: 32
<212> TYPE: RNA
<213> ORGANISM: Artificial Sequence
<220> FEATURE:
<223> OTHER INFORMATION: Description of Artificial Sequence: Synthetic
      guide RNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u

<400> SEQUENCE: 5
nnnnnnnnnn nnnnnnnnnn guuuuagagc ua                                    32

<210> SEQ ID NO 6
<211> LENGTH: 42
<212> TYPE: RNA
<213> ORGANISM: Artificial Sequence
<220> FEATURE:
<223> OTHER INFORMATION: Description of Artificial Sequence: Synthetic
      guide RNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u

<400> SEQUENCE: 6
nnnnnnnnnn nnnnnnnnnn guuuuagagc uaugcuguuu ug                         42

<210> SEQ ID NO 7
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      guide RNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u

<400> SEQUENCE: 7
nnnnnnnnnn nnnnnnnnnn guuuuagagc uaugcu                                    36

<210> SEQ ID NO 8
<211> LENGTH: 262
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (63)..(262)
<223> OTHER INFORMATION: a, c, u, g, unknown or other and this region
      may encompass 0-200 nucleotides
<220> FEATURE:
<221> NAME/KEY: misc_feature
<222> LOCATION: (63)..(262)
<223> OTHER INFORMATION: n is a, c, g, or u

<400> SEQUENCE: 8
nnnnnnnnnn nnnnnnnnnn guuuuagagc uagaaauagc aaguuaaaau aaggcuaguc           60
cgnnnnnnnn nnnnnnnnnn nnnnnnnnnn nnnnnnnnnn nnnnnnnnnn nnnnnnnnnn          120
nnnnnnnnnn nnnnnnnnnn nnnnnnnnnn nnnnnnnnnn nnnnnnnnnn nnnnnnnnnn          180
nnnnnnnnnn nnnnnnnnnn nnnnnnnnnn nnnnnnnnnn nnnnnnnnnn nnnnnnnnnn          240
nnnnnnnnnn nnnnnnnnnn nn                                                   262

<210> SEQ ID NO 9
<211> LENGTH: 275
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (76)..(275)
```

```
<223> OTHER INFORMATION: a, c, u, g, unknown or other and this region
      may encompass 0-200 nucleotides
<220> FEATURE:
<221> NAME/KEY: misc_feature
<222> LOCATION: (76)..(275)
<223> OTHER INFORMATION: n is a, c, g, or u

<400> SEQUENCE: 9
nnnnnnnnnn nnnnnnnnnn guuuuagagc uaugcugaaa agcauagcaa guuaaaauaa      60
ggcuaguccg uuaucnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnn                                275

<210> SEQ ID NO 10
<211> LENGTH: 287
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (88)..(287)
<223> OTHER INFORMATION: a, c, u, g, unknown or other and this region
      may encompass 0-200 nucleotides
<220> FEATURE:
<221> NAME/KEY: misc_feature
<222> LOCATION: (88)..(287)
<223> OTHER INFORMATION: n is a, c, g, or u

<400> SEQUENCE: 10
nnnnnnnnnn nnnnnnnnnn guuuuagagc uaugcuguuu uggaaacaaa acagcauagc      60
aaguuaaaau aaggcuaguc cguuaucnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnn                   287

<210> SEQ ID NO 11
<211> LENGTH: 296
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u
<220> FEATURE:
<221> NAME/KEY: modified_base
<222> LOCATION: (97)..(296)
<223> OTHER INFORMATION: a, c, u, g, unknown or other and this region
```

```
        may encompass 0-200 nucleotides
<220> FEATURE:
<221> NAME/KEY: misc_feature
<222> LOCATION: (97)..(296)
<223> OTHER INFORMATION: n is a, c, g, or u

<400> SEQUENCE: 11
nnnnnnnnnn nnnnnnnnnn guuuuagagc uagaaauagc aaguuaaaau aaggcuaguc      60
cguuaucaac uugaaaaagu ggcaccgagu cggugcnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnn         296

<210> SEQ ID NO 12
<211> LENGTH: 96
<212> TYPE: RNA
<213> ORGANISM: Artificial Sequence
<220> FEATURE:
<223> OTHER INFORMATION: Description of Artificial Sequence: Synthetic
      guide RNA oligonucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u

<400> SEQUENCE: 12
nnnnnnnnnn nnnnnnnnnn guuuaagagc uagaaauagc aaguuuaaau aaggcuaguc      60
cguuaucaac uugaaaaagu ggcaccgagu cggugc                                96

<210> SEQ ID NO 13
<211> LENGTH: 106
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
<220> FEATURE:
<221> NAME/KEY: misc_feature
<222> LOCATION: (1)..(20)
<223> OTHER INFORMATION: n is a, c, g, or u

<400> SEQUENCE: 13
nnnnnnnnnn nnnnnnnnnn guuuuagagc uaugcuggaa acagcauagc aaguuuaaau      60
aaggcuaguc cguuaucaac uugaaaaagu ggcaccgagu cggugc                    106

<210> SEQ ID NO 14
<211> LENGTH: 106
<212> TYPE: RNA
<213> ORGANISM: Artificial Sequence
<220> FEATURE:
<223> OTHER INFORMATION: Description of Artificial Sequence: Synthetic
      guide RNA polynucleotide
<220> FEATURE:
<221> NAME/KEY: modified_base
<222> LOCATION: (1)..(20)
<223> OTHER INFORMATION: a, c, u, g, unknown or other and this region
      may encompass 17-20 nucleotides
```

```
<220> FEATURE:
<221> NAME/KEY: misc_feature
<222> LOCATION: (1)..(20)
<223> OTHER INFORMATION: n is a, c, g, or u

<400> SEQUENCE: 14
nnnnnnnnnn nnnnnnnnnn guuuaagagc uaugcuggaa acagcauagc aaguuuaaau      60
aaggcuaguc cguuaucaac uugaaaaagu ggcaccgagu cggugc                   106

<210> SEQ ID NO 15
<211> LENGTH: 80
<212> TYPE: DNA
<213> ORGANISM: Artificial Sequence
<220> FEATURE:
<223> OTHER INFORMATION: Synthetic guide RNA oligonucleotide
<220> FEATURE:
<221> NAME/KEY: misc_feature
<223> OTHER INFORMATION: Description of Combined DNA/RNA Molecule:
      Synthetic guide RNA oligonucleotide

<400> SEQUENCE: 15
guuuuagagc uagaaauagc aaguuuaaau aaggcuaguc cguuaucaac uugaaaaagu      60
ggcaccgagt cggugcuuuu                                                 80

<210> SEQ ID NO 16
<211> LENGTH: 60
<212> TYPE: RNA
<213> ORGANISM: Artificial Sequence
<220> FEATURE:
<223> OTHER INFORMATION: Description of Artificial Sequence: Synthetic
      guide RNA oligonucleotide

<400> SEQUENCE: 16
uagcaaguua aaauaaggcu aguccguuau caacuugaaa aaguggcacc gagucggugc      60

<210> SEQ ID NO 17
<211> LENGTH: 64
<212> TYPE: RNA
<213> ORGANISM: Artificial Sequence
<220> FEATURE:
<223> OTHER INFORMATION: Description of Artificial Sequence: Synthetic
      guide RNA oligonucleotide

<400> SEQUENCE: 17
agcauagcaa guuaaaauaa ggcuaguccg uuaucaacuu gaaaagugg caccgagucg      60 gugc                                                                 64

<210> SEQ ID NO 18
<211> LENGTH: 1368
<212> TYPE: PRT
<213> ORGANISM: Streptococcus pyogenes

<400> SEQUENCE: 18

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
                740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
```

-continued

```
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
Phe Glu Leu Glu Asn Gly Arg Lys Arg Met Leu Ala Ser Ala Gly
        1205                1210                1215
Glu Leu Gln Lys Gly Asn Glu Leu Ala Leu Pro Ser Lys Tyr Val
        1220                1225                1230
Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys
        1250                1255                1260
His Tyr Leu Asp Glu Ile Ile Glu Gln Ile Ser Glu Phe Ser Lys
        1265                1270                1275
Arg Val Ile Leu Ala Asp Ala Asn Leu Asp Lys Val Leu Ser Ala
        1280                1285                1290
Tyr Asn Lys His Arg Asp Lys Pro Ile Arg Glu Gln Ala Glu Asn
        1295                1300                1305
Ile Ile His Leu Phe Thr Leu Thr Asn Leu Gly Ala Pro Ala Ala
        1310                1315                1320
```

```
Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      binding oligonucleotide

<400> SEQUENCE: 19
aaacaugagg auuacccaug ucg                                             23

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      binding oligonucleotide

<400> SEQUENCE: 20
aaacaugagg aucacccaug ucg                                             23

<210> SEQ ID NO 21
<211> LENGTH: 15
<212> TYPE: RNA
<213> ORGANISM: Artificial Sequence
<220> FEATURE:
<223> OTHER INFORMATION: Description of Artificial Sequence: Synthetic
      binding oligonucleotide

<400> SEQUENCE: 21
gcccugaaga agggc                                                      15

<210> SEQ ID NO 22
<211> LENGTH: 15
<212> TYPE: RNA
<213> ORGANISM: Artificial Sequence
<220> FEATURE:
<223> OTHER INFORMATION: Description of Artificial Sequence: Synthetic
      binding oligonucleotide

<400> SEQUENCE: 22
gcccugaaaa agggc                                                      15

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
      binding oligonucleotide

<400> SEQUENCE: 23
guucacugcc guauaggcag                                                 20

<210> SEQ ID NO 24
<211> LENGTH: 28
<212> TYPE: RNA
```

<213> ORGANISM: Artificial Sequence
<220> FEATURE:
<223> OTHER INFORMATION: Description of Artificial Sequence: Synthetic
       binding oligonucleotide

<400> SEQUENCE: 24
guucacugcc guauaggcag cuaagaaa                                                28

<210> SEQ ID NO 25
<211> LENGTH: 130
<212> TYPE: PRT
<213> ORGANISM: Enterobacteria phage MS2
<220> FEATURE:
<221> NAME/KEY: misc_feature
<223> OTHER INFORMATION: MS2 coat polypeptide

<400> SEQUENCE: 25

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 26
<211> LENGTH: 130
<212> TYPE: PRT
<213> ORGANISM: Enterobacteria phage MS2
<220> FEATURE:
<221> NAME/KEY: misc_feature
<223> OTHER INFORMATION: MS2 N55K polypeptide

<400> SEQUENCE: 26

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

```
Leu Lys Asp Gly Asn Pro Ile Pro Ser Ala Ile Ala Ala Asn Ser Gly
        115                 120                 125

Ile Tyr
    130

<210> SEQ ID NO 27
<211> LENGTH: 117
<212> TYPE: PRT
<213> ORGANISM: Enterobacteria phage MS2
<220> FEATURE:
<221> NAME/KEY: misc_feature
<223> OTHER INFORMATION: MS2deltaFG polypeptide

<400> SEQUENCE: 27

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr
        115

<210> SEQ ID NO 28
<211> LENGTH: 262
<212> TYPE: PRT
<213> ORGANISM: Artificial Sequence
<220> FEATURE:
<223> OTHER INFORMATION: Description of Artificial Sequence: Synthetic
      dimeric MS2 coat polypeptide

<400> SEQUENCE: 28

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Leu Tyr Gly Ala Met Ala Ser Asn Phe Thr Gln Phe Val Leu Val Asp
    130                 135                 140
```

```
Asn Gly Gly Thr Gly Asp Val Thr Val Ala Pro Ser Asn Phe Ala Asn
145                 150                 155                 160

Gly Val Ala Glu Trp Ile Ser Ser Asn Ser Arg Ser Gln Ala Tyr Lys
            165                 170                 175

Val Thr Cys Ser Val Arg Gln Ser Ser Ala Gln Asn Arg Lys Tyr Thr
            180                 185                 190

Ile Lys Val Glu Val Pro Lys Val Ala Thr Gln Thr Val Gly Gly Val
            195                 200                 205

Glu Leu Pro Val Ala Ala Trp Arg Ser Tyr Leu Asn Met Glu Leu Thr
210                 215                 220

Ile Pro Ile Phe Ala Thr Asn Ser Asp Cys Glu Leu Ile Val Lys Ala
225                 230                 235                 240

Met Gln Gly Leu Leu Lys Asp Gly Asn Pro Ile Pro Ser Ala Ile Ala
            245                 250                 255

Ala Asn Ser Leu Ile Asn
            260

<210> SEQ ID NO 29
<211> LENGTH: 262
<212> TYPE: PRT
<213> ORGANISM: Artificial Sequence
<220> FEATURE:
<223> OTHER INFORMATION: Description of Artificial Sequence: Synthetic
      dimeric MS2 N55K polypeptide

<400> SEQUENCE: 29

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
            35                  40                  45

Val Arg Gln Ser Ser Ala Gln Lys Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
            85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
            115                 120                 125

Leu Tyr Gly Ala Met Ala Ser Asn Phe Thr Gln Phe Val Leu Val Asp
130                 135                 140

Asn Gly Gly Thr Gly Asp Val Thr Val Ala Pro Ser Asn Phe Ala Asn
145                 150                 155                 160

Gly Val Ala Glu Trp Ile Ser Ser Asn Ser Arg Ser Gln Ala Tyr Lys
            165                 170                 175

Val Thr Cys Ser Val Arg Gln Ser Ser Ala Gln Lys Arg Lys Tyr Thr
            180                 185                 190

Ile Lys Val Glu Val Pro Lys Val Ala Thr Gln Thr Val Gly Gly Val
            195                 200                 205

Glu Leu Pro Val Ala Ala Trp Arg Ser Tyr Leu Asn Met Glu Leu Thr
210                 215                 220

Ile Pro Ile Phe Ala Thr Asn Ser Asp Cys Glu Leu Ile Val Lys Ala
225                 230                 235                 240
```

```
Met Gln Gly Leu Leu Lys Asp Gly Asn Pro Ile Pro Ser Ala Ile Ala
                245                 250                 255

Ala Asn Ser Leu Ile Asn
            260

<210> SEQ ID NO 30
<211> LENGTH: 236
<212> TYPE: PRT
<213> ORGANISM: Artificial Sequence
<220> FEATURE:
<223> OTHER INFORMATION: Description of Artificial Sequence: Synthetic
      dimeric MS2deltaFG polypeptide

<400> SEQUENCE: 30

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Lys Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Leu Tyr Gly Ala Met Ala Ser Asn Phe Thr Gln Phe Val
        115                 120                 125

Leu Val Asp Asn Gly Gly Thr Gly Asp Val Thr Val Ala Pro Ser Asn
    130                 135                 140

Phe Ala Asn Gly Val Ala Glu Trp Ile Ser Ser Asn Ser Arg Ser Gln
145                 150                 155                 160

Ala Tyr Lys Val Thr Cys Ser Val Arg Gln Ser Ser Ala Gln Lys Arg
                165                 170                 175

Lys Tyr Thr Ile Lys Val Glu Val Pro Lys Gly Ala Trp Arg Ser Tyr
            180                 185                 190

Leu Asn Met Glu Leu Thr Ile Pro Ile Phe Ala Thr Asn Ser Asp Cys
        195                 200                 205

Glu Leu Ile Val Lys Ala Met Gln Gly Leu Leu Lys Asp Gly Asn Pro
    210                 215                 220

Ile Pro Ser Ala Ile Ala Ala Asn Ser Leu Ile Asn
225                 230                 235

<210> SEQ ID NO 31
<211> LENGTH: 22
<212> TYPE: PRT
<213> ORGANISM: Enterobacteria phage lambda N

<400> SEQUENCE: 31

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 32
```

```
<211> LENGTH: 107
<212> TYPE: PRT
<213> ORGANISM: Enterobacteria phage lambda N

<400> SEQUENCE: 32

Met Asp Ala Gln Thr Arg Arg Glu Arg Arg Ala Glu Lys Gln Ala
1               5                   10                  15

Gln Trp Lys Ala Ala Asn Pro Leu Leu Val Gly Val Ser Ala Lys Pro
            20                  25                  30

Val Asn Arg Pro Ile Leu Ser Leu Asn Arg Lys Pro Lys Ser Arg Val
        35                  40                  45

Glu Ser Ala Leu Asn Pro Ile Asp Leu Thr Val Leu Ala Glu Tyr His
    50                  55                  60

Lys Gln Ile Glu Ser Asn Leu Gln Arg Ile Glu Arg Lys Asn Gln Arg
65                  70                  75                  80

Thr Trp Tyr Ser Lys Pro Gly Glu Arg Gly Ile Thr Cys Ser Gly Arg
                85                  90                  95

Gln Lys Ile Lys Gly Lys Ser Ile Pro Leu Ile
            100                 105

<210> SEQ ID NO 33
<211> LENGTH: 583
<212> TYPE: PRT
<213> ORGANISM: Planomicrobium okeanokoites

<400> SEQUENCE: 33

Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240
```

Leu Gly Leu Val Lys Gln Gly Lys Lys Glu Phe Ile Ile Pro Thr Leu
            245                 250                 255

Gly Lys Pro Asp Asn Lys Glu Phe Ile Ser His Ala Phe Lys Ile Thr
        260                 265                 270

Gly Glu Gly Leu Lys Val Leu Arg Arg Ala Lys Gly Ser Thr Lys Phe
            275                 280                 285

Thr Arg Val Pro Lys Arg Val Tyr Trp Glu Met Leu Ala Thr Asn Leu
        290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365

Tyr Gln Leu Lys Asp His Ile Leu Gln Phe Val Ile Pro Asn Arg Gly
    370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
        435                 440                 445

Gly Ser Arg Lys Pro Asp Gly Ala Ile Tyr Thr Val Gly Ser Pro Ile
    450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
        515                 520                 525

Lys Gly Asn Tyr Lys Ala Gln Leu Thr Arg Leu Asn His Ile Thr Asn
    530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580

<210> SEQ ID NO 34
<211> LENGTH: 1752
<212> TYPE: DNA
<213> ORGANISM: Planomicrobium okeanokoites

<400> SEQUENCE: 34 atgttttga gtatggtttc taaaataaga actttcggtt gggttcaaaa tccaggtaaa      60
tttgagaatt taaacgagt agttcaagta tttgatagaa attctaaagt acataatgaa     120

```
gtgaaaaata taaagatacc aaccctagtc aagaaagta agatccaaaa agaactagtt      180
gctattatga atcaacatga tttgatttat acatataaag agttagtagg aacaggaact      240
tcaatacgtt cagaagcacc atgcgatgca attattcaag caacaatagc agatcaagga      300
aataaaaaag gctatatcga taattggtca tctgacggtt ttttgcgttg ggcacatgct      360
ttaggattta ttgaatatat aaataaaagt gattcttttg taataactga tgttggactt      420
gcttactcta aatcagctga cggcagcgcc attgaaaaag agttttgat tgaagcgata      480 tcatcttatc ctccagcgat tcgtatttta actttgctag aagatggaca acatttgaca      540
aagtttgatc ttggcaagaa tttaggtttt agtggagaaa gtggatttac ttctctaccg      600
gaaggaattc ttttagatac tctagctaat gctatgccta agataaagg cgaaattcgt      660 aataattggg aaggatcttc agataagtac gcaagaatga taggtggttg gctggataaa      720
ctaggattag taaagcaagg aaaaaaagaa tttatcattc ctactttggg taagccggac      780
aataaagagt ttatatccca cgcttttaaa attactggag aaggtttgaa agtactgcgt      840
cgagcaaaag gctctacaaa atttacacgt gtacctaaaa gagtatattg ggaaatgctt      900
gctacaaacc taaccgataa agagtatgta agaacaagaa gagctttgat tttagaaata      960
ttaatcaaag ctggatcatt aaaaatgaa caaatacaag acaacttgaa gaaattagga     1020
tttgatgaag ttatagaaac tattgaaaat gatatcaaag gcttaattaa cacaggtata     1080
tttatagaaa tcaagggcg atttttatcaa ttgaaagacc atattcttca atttgtaata     1140
cctaatcgtg gtgtgactaa gcaactagtc aaaagtgaac tggaggagaa gaaatctgaa     1200
cttcgtcata aattgaaata tgtgcctcat gaatatattg aattaattga aattgccaga     1260
aattccactc aggatagaat tcttgaaatg aaggtaatgg aatttttat gaaagtttat     1320 ggatatagag gtaaacattt gggtggatca aggaaaccgg acggagcaat ttatactgtc     1380
ggatctccta ttgattacgg tgtgatcgtg gatactaaag cttatagcgg aggttataat     1440
ctgccaattg gccaagcaga tgaaatgcaa cgatatgtcg aagaaaatca aacacgaaac     1500
aaacatatca accctaatga atggtggaaa gtctatccat cttctgtaac ggaatttaag     1560
tttttatttg tgagtggtca cttttaaagga aactacaaag ctcagcttac acgattaaat     1620
catatcacta attgtaatgg agctgttctt agtgtagaag agcttttaat tggtggagaa     1680
atgattaaag ccggcacatt aaccttagag gaagtgagac ggaaatttaa taacggcgag     1740
ataaactttt aa                                                        1752
```

<210> SEQ ID NO 35  
<211> LENGTH: 16  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 35

```
gtaaaacgac ggccag                                                      16
```

<210> SEQ ID NO 36  
<211> LENGTH: 28  
<212> TYPE: RNA  
<213> ORGANISM: Artificial Sequence  
<220> FEATURE:  
<223> OTHER INFORMATION: Description of Artificial Sequence: Synthetic Csy4 RNA binding oligonucleotide

<400> SEQUENCE: 36

-continued

```
guucacugcc guauaggcag cuaagaaa                                    28

<210> SEQ ID NO 37
<211> LENGTH: 252
<212> TYPE: RNA
<213> ORGANISM: Artificial Sequence
<220> FEATURE:
<223> OTHER INFORMATION: Description of Artificial Sequence: Synthetic
      multiplex guide RNA polynucleotide
<220> FEATURE:
<221> NAME/KEY: modified_base
<222> LOCATION: (21)..(40)
<223> OTHER INFORMATION: a, c, u, g, unknown or other
<220> FEATURE:
<221> NAME/KEY: misc_feature
<222> LOCATION: (21)..(40)
<223> OTHER INFORMATION: n is a, c, g, or u
<220> FEATURE:
<221> NAME/KEY: modified_base
<222> LOCATION: (137)..(156)
<223> OTHER INFORMATION: a, c, u, g, unknown or other
<220> FEATURE:
<221> NAME/KEY: misc_feature
<222> LOCATION: (137)..(156)
<223> OTHER INFORMATION: n is a, c, g, or u

<400> SEQUENCE: 37
guucacugcc guauaggcag nnnnnnnnnn nnnnnnnnnn guuuuagagc uagaaauagc    60
aaguuaaaau aaggcuaguc cguuaucaac uugaaaaagu ggcaccgagu cggugcguuc   120
acugccguau aggcagnnnn nnnnnnnnnn nnnnnnguuu uagagcuaga aauagcaagu   180
uaaaauaagg cuaguccguu aucaacuuga aaaaguggca ccgagucggu gcguucacug   240
ccguauaggc ag                                                      252

<210> SEQ ID NO 38
<211> LENGTH: 1167
<212> TYPE: DNA
<213> ORGANISM: Artificial Sequence
<220> FEATURE:
<223> OTHER INFORMATION: Description of Artificial Sequence: Synthetic
      Csy4-FokI N-terminal fusion polynucleotide

<400> SEQUENCE: 38
atggaccact acctcgacat tcgcttgcga ccggacccgg aatttccccc ggcgcaactc    60
atgagcgtgc tcttcggcaa gctccaccag gccctggtgg cacagggcgg ggacaggatc   120
ggcgtgagct cccccgacct cgacgaaagc cgctcccggc tgggcgagcg cctgcgcatt   180
catgcctcgg cggacgacct tcgtgccctg ctcgcccggc cctggctgga agggttgcgg   240
gaccatctgc aattcggaga accggcagtc gtgcctcacc ccacaccgta ccgtcaggtc   300
agtcgggttc aggcgaaaag caatccggaa cgcctgcggc ggcggctcat cgccggcac   360 gatctgagtg aggaggaggc tcggaaacgc attcccgata cggtcgcgag agccttggac   420
ctgcccttcg tcacgctacg cagccagagc accggacagc acttccgtct cttcatccgc   480
cacgggccgt gcaggtgac ggcagaggaa ggaggattca cctgttacgg gttgagcaaa   540
ggaggtttcg ttccctggtt cggtggcggt ggatcccaac tagtcaaaag tgaactggag   600
gagaagaaat ctgaacttcg tcataaattg aaatatgtgc ctcatgaata tattgaatta   660
attgaaattg ccagaaattc cactcaggat agaattcttg aaatgaaggt aatggaattt   720
tttatgaaag tttatggata tagaggtaaa catttgggtg gatcaaggaa accggacgga   780 gcaattata ctgtcggatc tcctattgat tacggtgtga tcgtggatac taaagcttat   840
```

```
agcggaggtt ataatctgcc aattggccaa gcagatgaaa tgcaacgata tgtcgaagaa    900
aatcaaacac gaaacaaaca tatcaaccct aatgaatggt ggaaagtcta tccatcttct    960
gtaacggaat ttaagttttt atttgtgagt ggtcacttta aaggaaacta caaagctcag   1020
cttacacgat taaatcatat cactaattgt aatggagctg ttcttagtgt agaagagctt   1080
ttaattggtg agaaatgat  taaagccggc acattaacct  tagaggaagt cagacggaaa   1140
tttaataacg gcgagataaa cttttga                                        1167
```

<210> SEQ ID NO 39
<211> LENGTH: 388
<212> TYPE: PRT
<213> ORGANISM: Artificial Sequence
<220> FEATURE:
<223> OTHER INFORMATION: Description of Artificial Sequence: Synthetic
      Csy4-FokI N-terminal fusion polypeptide

<400> SEQUENCE: 39

```
Met Asp His Tyr Leu Asp Ile Arg Leu Arg Pro Asp Pro Glu Phe Pro
1               5                   10                  15

Pro Ala Gln Leu Met Ser Val Leu Phe Gly Lys Leu His Gln Ala Leu
            20                  25                  30

Val Ala Gln Gly Gly Asp Arg Ile Gly Val Ser Phe Pro Asp Leu Asp
        35                  40                  45

Glu Ser Arg Ser Arg Leu Gly Glu Arg Leu Arg Ile His Ala Ser Ala
    50                  55                  60

Asp Asp Leu Arg Ala Leu Leu Ala Arg Pro Trp Leu Glu Gly Leu Arg
65                  70                  75                  80

Asp His Leu Gln Phe Gly Glu Pro Ala Val Val Pro His Pro Thr Pro
                85                  90                  95

Tyr Arg Gln Val Ser Arg Val Gln Ala Lys Ser Asn Pro Glu Arg Leu
            100                 105                 110

Arg Arg Arg Leu Met Arg Arg His Asp Leu Ser Glu Glu Glu Ala Arg
        115                 120                 125

Lys Arg Ile Pro Asp Thr Val Ala Arg Ala Leu Asp Leu Pro Phe Val
    130                 135                 140

Thr Leu Arg Ser Gln Ser Thr Gly Gln His Phe Arg Leu Phe Ile Arg
145                 150                 155                 160

His Gly Pro Leu Gln Val Thr Ala Glu Glu Gly Gly Phe Thr Cys Tyr
                165                 170                 175

Gly Leu Ser Lys Gly Gly Phe Val Pro Trp Phe Gly Gly Gly Gly Ser
            180                 185                 190

Gln Leu Val Lys Ser Glu Leu Glu Glu Lys Lys Ser Glu Leu Arg His
        195                 200                 205

Lys Leu Lys Tyr Val Pro His Glu Tyr Ile Glu Leu Ile Glu Ile Ala
    210                 215                 220

Arg Asn Ser Thr Gln Asp Arg Ile Leu Glu Met Lys Val Met Glu Phe
225                 230                 235                 240

Phe Met Lys Val Tyr Gly Tyr Arg Gly Lys His Leu Gly Gly Ser Arg
                245                 250                 255

Lys Pro Asp Gly Ala Ile Tyr Thr Val Gly Ser Pro Ile Asp Tyr Gly
            260                 265                 270

Val Ile Val Asp Thr Lys Ala Tyr Ser Gly Gly Tyr Asn Leu Pro Ile
        275                 280                 285

Gly Gln Ala Asp Glu Met Gln Arg Tyr Val Glu Glu Asn Gln Thr Arg
    290                 295                 300
```

Asn Lys His Ile Asn Pro Asn Glu Trp Trp Lys Val Tyr Pro Ser Ser
305                 310                 315                 320

Val Thr Glu Phe Lys Phe Leu Phe Val Ser Gly His Phe Lys Gly Asn
            325                 330                 335

Tyr Lys Ala Gln Leu Thr Arg Leu Asn His Ile Thr Asn Cys Asn Gly
        340                 345                 350

Ala Val Leu Ser Val Glu Glu Leu Leu Ile Gly Gly Glu Met Ile Lys
    355                 360                 365

Ala Gly Thr Leu Thr Leu Glu Glu Val Arg Arg Lys Phe Asn Asn Gly
370                 375                 380

Glu Ile Asn Phe
385

<210> SEQ ID NO 40
<211> LENGTH: 1167
<212> TYPE: DNA
<213> ORGANISM: Artificial Sequence
<220> FEATURE:
<223> OTHER INFORMATION: Description of Artificial Sequence: Synthetic
      Csy4-FokI C-terminal fusion polynucleotide

<400> SEQUENCE: 40
atgcaactag tcaaaagtga actggaggag aagaaatctg aacttcgtca taaattgaaa      60
tatgtgcctc atgaatatat tgaattaatt gaaattgcca gaaattccac tcaggataga     120
attcttgaaa tgaaggtaat ggaattttt atgaaagttt atggatatag aggtaaacat     180
ttgggtggat caaggaaacc ggacggagca atttatactg tcggatctcc tattgattac     240
ggtgtgatcg tggatactaa agcttatagc ggaggttata atctgccaat tggccaagca     300
gatgaaatgc aacgatatgt cgaagaaaat caaacacgaa acaaacatat caaccctaat     360
gaatggtgga agtctatcc atcttctgta acggaattta gttttttatt tgtgagtggt     420
cactttaaag gaaactacaa agctcagctt acacgattaa atcatatcac taattgtaat     480
ggagctgttc ttagtgtaga agagcttta attggtggag aaatgattaa agccggcaca     540
ttaaccttag aggaagtcag acggaaattt aataacggcg agataaactt ggtggcggt     600
ggatccgacc actacctcga cattcgcttg cgaccggacc cggaatttcc cccggcgcaa     660
ctcatgagcg tgctcttcgg caagctccac caggccctgg tggcacaggg cggggacagg     720
atcggcgtga gcttccccga cctcgacgaa agccgctccc ggctgggcga gcgcctgcgc     780
attcatgcct cggcggacga ccttcgtgcc ctgctcgccc ggccctggct ggaagggttg     840
cgggaccatc tgcaattcgg agaaccggca gtcgtgcctc accccacacc gtaccgtcag     900
gtcagtcggg ttcaggcgaa aagcaatccg gaacgcctgc ggcggcggct catgcgccgg     960
cacgatctga gtgaggagga ggctcggaaa cgcattcccg atacggtcgc gagagccttg    1020
gacctgccct tcgtcacgct acgcagccag agcaccggac agcacttccg tctcttcatc    1080
cgccacgggc cgttgcaggt gacggcagag gaaggaggat tcacctgtta cgggttgagc    1140
aaaggaggtt tcgttccctg gttctga                                        1167

<210> SEQ ID NO 41
<211> LENGTH: 388
<212> TYPE: PRT
<213> ORGANISM: Artificial Sequence
<220> FEATURE:
<223> OTHER INFORMATION: Description of Artificial Sequence: Synthetic
      Csy4-FokI C-terminal fusion polypeptide

<400> SEQUENCE: 41

```
Met Gln Leu Val Lys Ser Glu Leu Glu Glu Lys Ser Glu Leu Arg
1               5                   10                  15

His Lys Leu Lys Tyr Val Pro His Glu Tyr Ile Glu Leu Ile Glu Ile
            20                  25                  30

Ala Arg Asn Ser Thr Gln Asp Arg Ile Leu Glu Met Lys Val Met Glu
            35                  40                  45

Phe Phe Met Lys Val Tyr Gly Tyr Arg Gly Lys His Leu Gly Gly Ser
        50                  55                  60

Arg Lys Pro Asp Gly Ala Ile Tyr Thr Val Gly Ser Pro Ile Asp Tyr
65                  70                  75                  80

Gly Val Ile Val Asp Thr Lys Ala Tyr Ser Gly Gly Tyr Asn Leu Pro
                85                  90                  95

Ile Gly Gln Ala Asp Glu Met Gln Arg Tyr Val Glu Glu Asn Gln Thr
            100                 105                 110

Arg Asn Lys His Ile Asn Pro Asn Glu Trp Trp Lys Val Tyr Pro Ser
        115                 120                 125

Ser Val Thr Glu Phe Lys Phe Leu Phe Val Ser Gly His Phe Lys Gly
    130                 135                 140

Asn Tyr Lys Ala Gln Leu Thr Arg Leu Asn His Ile Thr Asn Cys Asn
145                 150                 155                 160

Gly Ala Val Leu Ser Val Glu Glu Leu Leu Ile Gly Gly Glu Met Ile
                165                 170                 175

Lys Ala Gly Thr Leu Thr Leu Glu Glu Val Arg Arg Lys Phe Asn Asn
            180                 185                 190

Gly Glu Ile Asn Phe Gly Gly Gly Ser Asp His Tyr Leu Asp Ile
        195                 200                 205

Arg Leu Arg Pro Asp Pro Glu Phe Pro Pro Ala Gln Leu Met Ser Val
210                 215                 220

Leu Phe Gly Lys Leu His Gln Ala Leu Val Ala Gln Gly Gly Asp Arg
225                 230                 235                 240

Ile Gly Val Ser Phe Pro Asp Leu Asp Glu Ser Arg Ser Arg Leu Gly
                245                 250                 255

Glu Arg Leu Arg Ile His Ala Ser Ala Asp Asp Leu Arg Ala Leu Leu
            260                 265                 270

Ala Arg Pro Trp Leu Glu Gly Leu Arg Asp His Leu Gln Phe Gly Glu
        275                 280                 285

Pro Ala Val Val Pro His Pro Thr Pro Tyr Arg Gln Val Ser Arg Val
    290                 295                 300

Gln Ala Lys Ser Asn Pro Glu Arg Leu Arg Arg Leu Met Arg Arg
305                 310                 315                 320

His Asp Leu Ser Glu Glu Glu Ala Arg Lys Arg Ile Pro Asp Thr Val
                325                 330                 335

Ala Arg Ala Leu Asp Leu Pro Phe Val Thr Leu Arg Ser Gln Ser Thr
            340                 345                 350

Gly Gln His Phe Arg Leu Phe Ile Arg His Gly Pro Leu Gln Val Thr
        355                 360                 365

Ala Glu Glu Gly Gly Phe Thr Cys Tyr Gly Leu Ser Lys Gly Gly Phe
    370                 375                 380

Val Pro Trp Phe
385
```

<210> SEQ ID NO 42

-continued

```
<211> LENGTH: 79
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 42
ggaaccauuc aaaacagcau agcaaguuaa aauaaggcua guccguuauc aacuugaaaa      60
aguggcaccg agucggugc                                                  79

<210> SEQ ID NO 43
<211> LENGTH: 70
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 43
caaaacagca uagcaaguua aauaaggcu aguccguuau caacuugaaa aaguggcacc       60
gagucggugc                                                            70

<210> SEQ ID NO 44
<211> LENGTH: 45
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 44
uagcaaguua aauaaggcu aguccguuau caacuugaaa aagug                      45

<210> SEQ ID NO 45
<211> LENGTH: 32
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 45
uagcaaguua aauaaggcu aguccguuau ca                                    32

<210> SEQ ID NO 46
<211> LENGTH: 26
<212> TYPE: RNA
<213> ORGANISM: Artificial Sequence
<220> FEATURE:
<223> OTHER INFORMATION: Description of Artificial Sequence: Synthetic
      tracrRNA oligonucleotide

<400> SEQUENCE: 46
uagcaaguua aauaaggcu aguccg                                           26

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 47

Gly Gly Gly Ser
```

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 48

Gly Gly Gly Gly Ser
1               5

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 49
ggtgagtgag tgtgtgcgtg tgg                                              23

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 50
gggcgatgcc acctacgg                                                    18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 51
gagggcgatg ccacctacgg                                                  20

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 52
gcgagggcga tgccacctac gg                                               22

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 53
ggcgagggcg atgccaccta cgg                                          23

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 54
gggcgagggc gatgccacct acgg                                         24

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 55
gagggcgagg gcgatgccac ctacgg                                       26

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 56
gcgagggcga gggcgatgcc acctacgg                                     28

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 57
gcacgggcag cttgccggtg g                                            21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 58
gggcacgggc agcttgccgg tgg                                          23

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 59
gccgttcttc tgcttgtcgg                                              20

```
<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 60
gatgccgttc ttctgcttgt cgg                                              23

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 61
gtgcagatga acttcaggg                                                   19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 62
ggtgcagatg aacttcaggg                                                  20

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 63
ggtggtgcag atgaacttca ggg                                              23

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 64
gaggagctgt tcaccgggg                                                   19

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 65
gcgaggagct gttcaccggg g                                                21
```

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 66
gggcgaggag ctgttcaccg ggg                                           23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 67 gtgggggag tttgctcctg g                                              21

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 68
gggtgggggg agtttgctcc tgg                                           23

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 69
gagtgagtgt gtgcgtgtgg                                               20

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 70
ggtgagtgag tgtgtgcgtg tgg                                           23

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 71
gtccgagcag aagaagaagg g                                             21

```
<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 72
gagtccgagc agaagaagaa ggg                                            23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 73
gatgtagtgt ttccacaggg                                                20

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      target binding site oligonucleotide

<400> SEQUENCE: 74
gcagatgtag tgtttccaca ggg                                            23

<210> SEQ ID NO 75
<211> LENGTH: 67
<212> TYPE: DNA
<213> ORGANISM: Homo sapiens

<400> SEQUENCE: 75
gaagctggag gaggaagggc ctgagtccga gcagaagaag aagggctccc atcacatcaa    60
ccggtgg                                                              67

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gaagctggag gagga                                                     15

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcaaccggtg g                                                         11

<210> SEQ ID NO 78
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gaagctggag gaggaagg                                                       18

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gggctcccat cacatcaacc ggtgg                                               25

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gaagctggag gaggaagggc ctga                                                24

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gaagctggag gagg                                                           14

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaagctggag gaggaagggc ccatcacatc aaccggtgg                                39

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gaagctggag gaggaagggc tcgcacacat caaccggtgg                               40

<210> SEQ ID NO 84
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 84
gaagctggag gaggaagggc cttccatcac atcaaccggt gg                          42

<210> SEQ ID NO 85
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gaagctggag gaggaagggc ctgagtccca tcacatcaac cggtgg                      46

<210> SEQ ID NO 86
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gaagctggag gaggaagggc ctgagtccga gtcccatcac atcaaccggt gg               52

<210> SEQ ID NO 87
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gaagctggag gaggaagggc ctgagtccga gcagaagtcc catcacatca accggtgg         58

<210> SEQ ID NO 88
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gaagctggag gaggaagggc ctgagtcctg ccgtttgtag ccatcacatc aaccggtgg        59

<210> SEQ ID NO 89
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gaagctggag gaggaagggc ctgagtccga gcagaagagc tcccatcaca tcaaccggtg       60
g                                                                       61

<210> SEQ ID NO 90
<211> LENGTH: 61
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gaagctggag gaggaagggc ctgagtccga gcagaagaac tcccatcaca tcaaccggtg     60
g                                                                     61

<210> SEQ ID NO 91
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gaagctggag gaggaagggc ctgagtccga gcagaagaag ggctcccatc acatcaaccg     60
gtgg                                                                  64

<210> SEQ ID NO 92
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gaagctggag gaggaagggc ctgagtccga gcagaagaaa gggctcccat cacatcaacc     60
ggtgg                                                                 65

<210> SEQ ID NO 93
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gaagctggag gaggaagggc ctgagtccga gcagaagaac agaagggctc ccatcacatc     60
aaccggt                                                               67

<210> SEQ ID NO 94
<211> LENGTH: 67
<212> TYPE: DNA
<213> ORGANISM: Homo sapiens

<400> SEQUENCE: 94
gaagctggag gaggaagggc ctgagtccga gcagaagaag aagggctccc atcacatcaa     60
ccggtgg                                                               67

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
```
gaagctggag gaggaagggc ctgagtccga g    31

<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gaagctggag g    11

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gaagctggag g    11

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gaagctggag gaggaagggc ctgagtgg    28

<210> SEQ ID NO 99
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gaagctggag gaggaagggc tcccatcaca tcaaccggtg g    41

<210> SEQ ID NO 100
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gaagctggag gaggaagggc ctgagtccat cacatcaacc ggtgg    45

<210> SEQ ID NO 101
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101

```
gaagctggag gaggaagggc ctgagtccca tcacatcaac cggtgg                    46
```

<210> SEQ ID NO 102
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102

```
gaagctggag gaggaagggc ctgagtccga gcatcacatc aaccggtgg                 49
```

<210> SEQ ID NO 103
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103

```
gaagctggag gaggaagggc ctgagtccga gctcccatca catcaaccgg tgg            53
```

<210> SEQ ID NO 104
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104

```
gaagctggag gaggaagggc ctgagtccga gcagaagggc tcccatcaca tcaaccggtg     60
g                                                                     61
```

<210> SEQ ID NO 105
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105

```
gaagctggag gaggaagggc ctgagtccga gcagaagaag ggctcccatc acatcaaccg     60
gtgg                                                                  64
```

<210> SEQ ID NO 106
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
gaagctggag gaggaagggc ctgagtccga gcagaaagaa gggctcccat cacatcaacc     60
ggtgg                                                                 65
```

<210> SEQ ID NO 107
<211> LENGTH: 67
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 107
gaagctggag gaggaagggc ctgagtccga gcagaagaac agaagggctc ccatcacatc    60
aaccggt                                                              67

<210> SEQ ID NO 108
<211> LENGTH: 23
<212> TYPE: DNA
<213> ORGANISM: Artificial Sequence
<220> FEATURE:
<223> OTHER INFORMATION: Synthetic target binding site oligonucleotide

<400> SEQUENCE: 108
ccacacgcac acactcactc acc                                            23

<210> SEQ ID NO 109
<211> LENGTH: 20
<212> TYPE: RNA
<213> ORGANISM: Artificial Sequence
<220> FEATURE:
<223> OTHER INFORMATION: Synthetic target binding site oligonucleotide

<400> SEQUENCE: 109
ggugagugag ugugugcgug                                                20

<210> SEQ ID NO 110
<211> LENGTH: 20
<212> TYPE: DNA
<213> ORGANISM: Artificial Sequence
<220> FEATURE:
<223> OTHER INFORMATION: Synthetic target binding site oligonucleotide

<400> SEQUENCE: 110
gtttgtactt tgtcctccgg                                                20

<210> SEQ ID NO 111
<211> LENGTH: 23
<212> TYPE: DNA
<213> ORGANISM: Artificial Sequence
<220> FEATURE:
<223> OTHER INFORMATION: Synthetic target binding site oligonucleotide

<400> SEQUENCE: 111
gccgtttgta ctttgtcctc cgg                                            23

<210> SEQ ID NO 112
<211> LENGTH: 21
<212> TYPE: DNA
<213> ORGANISM: Artificial Sequence
<220> FEATURE:
<223> OTHER INFORMATION: Synthetic target binding site oligonucleotide

<400> SEQUENCE: 112
gaagactgag gctacatagg g                                              21

<210> SEQ ID NO 113
<211> LENGTH: 23
<212> TYPE: DNA
<213> ORGANISM: Artificial Sequence
<220> FEATURE:
<223> OTHER INFORMATION: Synthetic target binding site oligonucleotide

<400> SEQUENCE: 113
```

```
gggaagactg aggctacata ggg                                         23
```

<210> SEQ ID NO 114
<211> LENGTH: 20
<212> TYPE: DNA
<213> ORGANISM: Artificial Sequence
<220> FEATURE:
<223> OTHER INFORMATION: Synthetic target binding site oligonucleotide

<400> SEQUENCE: 114

```
gcccccagag cagccactgg                                             20
```

<210> SEQ ID NO 115
<211> LENGTH: 23
<212> TYPE: DNA
<213> ORGANISM: Artificial Sequence
<220> FEATURE:
<223> OTHER INFORMATION: Synthetic target binding site oligonucleotide

<400> SEQUENCE: 115

```
gaggccccca gagcagccac tgg                                         23
```

US 9,885,033 B2

INCREASING SPECIFICITY FOR RNA-GUIDED GENOME EDITING

CLAIM OF PRIORITY

This application is a U.S. National Phase Application under 35 U.S.C. § 371 of International Patent Application No. PCT/US2014/029304, filed on Mar. 14, 2014, which claims priority under 35 USC § 119(e) to U.S. patent application Ser. Nos. 61/799,647, filed on Mar. 15, 2013; 61/838,178, filed on Jun. 21, 2013; 61/838,148, filed on Jun. 21, 2013, and 61/921,007, filed on Dec. 26, 2013. The entire contents of the foregoing are hereby incorporated by reference.

FEDERALLY SPONSORED RESEARCH OR DEVELOPMENT

This invention was made with Government support under Grant Nos. DP1 GM105378 awarded by the National Institutes of Health. The Government has certain rights in the invention.

TECHNICAL FIELD

Methods for increasing specificity of RNA-guided genome editing, e.g., editing using CRISPR/Cas9 systems.

BACKGROUND

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from *S. pyogenes* (hereafter simply Cas9) can be guided via base pair complementarity between the first 20 nucleotides of an engineered gRNA and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). Previous studies performed in vitro (Jinek et al., Science 337, 816-821 (2012)), in bacteria (Jiang et al., Nat Biotechnol 31, 233-239 (2013)) and in human cells (Cong et al., Science 339, 819-823 (2013)) have shown that Cas9-mediated cleavage can, in some cases, be abolished by single mismatches at the gRNA/target site interface, particularly in the last 10-12 nucleotides (nts) located in the 3' end of the 20 nt gRNA complementarity region.

SUMMARY

Studies have shown that CRISPR-Cas nucleases can tolerate up to five mismatches and still cleave; it is hard to predict the effects of any given single or combination of mismatches on activity. Taken together, these nucleases can show significant off-target effects but it can be challenging to predict these sites. Described herein are methods of genome editing using the CRISPR/Cas system, e.g., using Cas9 or Cas9-based fusion proteins.

Thus, in a first aspect, the invention provides a synthetic guide ribonucleic acid, wherein: one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain; and/or wherein one or more of the nucleotides is a deoxyribonucleic acid.

In one aspect, the invention provides a guide RNA molecule having a target complementarity region of 17-20 nucleotides, e.g., a sequence complementary to the complementary strand of 17-20 consecutive nucleotides of a target sequence, preferably a target sequence immediately 5' of a protospacer adjacent motif (PAM), e.g., NGG, NAG, or NNGG, wherein one or more of the RNA nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., one or more of the nucleotides within the sequence $X_{17-20}$, one or more of the nucleotides within the sequence $X_N$, or one or more of the nucleotides within any sequence of the gRNA. In no case is the $X_{17-20}$ identical to a sequence that naturally occurs adjacent to the rest of the RNA. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In one aspect, the invention provides a ribonucleic acid comprising or consisting of the sequence:

```
                                         (SEQ ID NO: 4)
(X17-20) GUUUUAGAGCUAUGCUGUUUUG (XN);

(SEQ ID NO: 5)
(X17-20) GUUUUAGAGCUA;

(SEQ ID NO: 6)
(X17-20) GUUUUAGAGCUAUGCUGUUUUG;

(SEQ ID NO: 7)
(X17-20) GUUUUAGAGCUAUGCU;

(SEQ ID NO: 8)
(X17-20) GUUUUAGAGCUAGAAAUAGCAAGUUAAAAUAAGGCUAGUCCG
(XN);

(SEQ ID NO: 9)
(X17-20) GUUUUAGAGCUAUGCUGAAAAGCAUAGCAAGUUAAAAUAAGG
CUAGUCCGUUAUC (XN);
```

($X_{17-20}$) GUUUUAGAGCUAUGCUGUUUUGGAAACAAAACAGCAUAGCAAGUUAAAAUAAGGCUAGUCCGUUAUC ($X_N$); (SEQ ID NO: 10)

($X_{17-20}$) GUUUUAGAGCUAGAAAUAGCAAGUUAAAAUAAGGCUAGUCCGUUAUCAACUUGAAAAAGUGGCACCGAGUCGGUG ($X_N$), (SEQ ID NO: 11)

($X_{17-20}$) GUUUAAGAGCUAGAAAUAGCAAGUUAAAAUAAGGCUAGUCCGUUAUCAACUUGAAAAAGUGGCACCGAGUCGGUGC; (SEQ ID NO: 12)

($X_{17-20}$) GUUUUAGAGCUAUGCUGGAAACAGCAUAGCAAGUUUAAAUAAGGCUAGUCCGUUAUCAACUUGAAAAAGUGGCACCGAGUCGGUGC; or (SEQ ID NO: 13)

($X_{17-20}$) GUUUAAGAGCUAUGCUGGAAACAGCAUAGCAAGUUUAAAUAAGGCUAGUCCGUUAUCAACUUGAAAAAGUGGCACCGAGUCGGUGC, (SEQ ID NO: 14)

wherein $X_{17-20}$ is a sequence complementary to the complementary strand of 17-20 consecutive nucleotides of a target sequence (though in some embodiments this complementarity region may be longer than 20 nts, e.g., 21, 22, 23, 24, 25 or more nts), preferably a target sequence immediately 5' of a protospacer adjacent motif (PAM), e.g., NGG, NAG, or NNGG, wherein one or more of the RNA nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., one or more of the nucleotides within the sequence $X_{17-20}$, one or more of the nucleotides within the sequence $X_N$, or one or more of the nucleotides within any sequence of the gRNA. In no case is the $X_{17-20}$ identical to a sequence that naturally occurs adjacent to the rest of the RNA. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In another aspect, the invention provides hybrid nucleic acids comprising or consisting of the sequence:
($X_{17-20}$) GUUUUAGAGCUAUGCUGUUUUG($X_N$) (SEQ ID NO:4);
($X_{17-20}$)GUUUUAGAGCUA (SEQ ID NO:5);
($X_{17-20}$) GUUUUAGAGCUAUGCUGUUUUG (SEQ ID NO:6);
($X_{17-20}$)GUUUUAGAGCUAUGCU (SEQ ID NO:7);
($X_{17-20}$)GUUUUAGAGCUAGAAAUAG-CAAGUUAAAAUAAGGCUAGUCCG($X_N$) (SEQ ID NO:8);
($X_{17-20}$)GUUUUAGAGCUAUGCUGAAAAGCAUAG-CAAGUUAAAAUAAGGCU AGUCCGUUAUC($X_N$) (SEQ ID NO:9);
($X_{17-20}$)GUUUUAGAGCUAUGCUGUUUUG-GAAACAAAACAGCAUAGCAAGU UAAAAUAAGGCUAGUCCGUUAUC($X_N$) (SEQ ID NO:10);
($X_{17-20}$)GUUUUAGAGCUAGAAAUAG-CAAGUUAAAAUAAGGCUAGUCCGUU AUCAAC-UUGAAAAAGUGGCACCGAGUCGGUGC($X_N$) (SEQ ID NO:11),
($X_{17-20}$)GUUUAAGAGCUAGAAAUAG-CAAGUUUAAAUAAGGCUAGUCCGUU AUCAAC-UUGAAAAAGUGGCACCGAGUCGGUGC(SEQ ID NO:12);
($X_{17-20}$)GUUUUAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:13); or
($X_{17-20}$)GUUUAAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:14), wherein the $X_{17-20}$ is a sequence complementary to the complementary strand of 17-20 consecutive nucleotides of a target sequence (though in some embodiments this complementarity region may be longer than 20 nts, e.g., 21, 22, 23, 24, 25 or more nts), preferably a target sequence immediately 5' of a protospacer adjacent motif (PAM), e.g., NGG, NAG, or NNGG, wherein the nucleic acid is at least partially or wholly DNA, or is partially RNA and partially DNA. In no case is the $X_{17-20}$ identical to a sequence that naturally occurs adjacent to the rest of the RNA. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In another aspect, the invention provides DNA molecules encoding the ribonucleic acids described herein.

In yet another aspect, the invention provides methods for inducing a single or double-stranded break in a target region of a double-stranded DNA molecule, e.g., in a genomic sequence in a cell. The methods include expressing in or introducing into the cell: a Cas9 nuclease or nickase; and (a) a guide RNA that includes one or more deoxyribonucleotides (e.g., where the sequence may also be partially or wholly DNA but with thymine in place or uracil), e.g., a guide RNA that includes a sequence of 17-20 nucleotides that are complementary to the complementary strand of a target sequence, preferably a target sequence immediately 5' of a protospacer adjacent motif (PAM), e.g., NGG, NAG, or NNGG, wherein the guide RNA includes one or more deoxyribonuclotides (e.g., where the defined sequence may also be partially or wholly DNA but with thymine in place or uracil), e.g., a hybrid nucleic acid as described herein; or (b) a guide RNA wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., a guide RNA that includes a sequence of 17-20 nucleotides that are complementary to a target sequence, preferably a target sequence immediately 5' of a protospacer adjacent motif (PAM), e.g., NGG, NAG, or NNGG, wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., a ribonucleic acid as described herein.

In yet another aspect, the invention provides methods for inducing a single or double-stranded break in a target region of a double-stranded DNA molecule, e.g., in a genomic sequence in a cell. The methods include expressing in or introducing into the cell:

a Cas9 nuclease or nickase;

a tracrRNA, e.g., comprising the sequence of GUUUUAGAGCUAGAAAUAGCAAGUUAAAAUAAGGCUAGUCCGUUAUCA ACUUGAAAAAGUGGCACCGAGTCGGUGCUUUU (SEQ ID NO:15) or an active portion thereof, UAGCAAGUUAAAAUAAGGCUAGUCCGUUAUCAACUUGAAAAAGUGGCA CCGAGUCGGUGC (SEQ ID NO:16) or an active portion thereof; AGCAUAGCAAGUUAAAAUAAGGCUAGUCCGUUAUCAACUUGAAAAAGU GGCACCGAGUCGGUGC (SEQ ID NO:17) or an active portion thereof, GGAACCAUUCAAAACAGCAUAGCAAGUUAAAAUAAGGCUAGUCCGUUA UCAACUUGAAAAAGUGGCACCGAGUCGGUGC (SEQ ID NO:42) or an active portion thereof; UAGCAAGUUAAAAUAAGGCUAGUCCGUUAUCAACUUGAAAAAGUGGCA CCGAGUCGGUGC (SEQ ID NO:16) or an active portion thereof; CAAAACAGCAUAGCAAGUUAAAAUAAGGCUAGUCCGUUAUCAACUUGA AAAGUGGCACCGAGUCGGUGC (SEQ ID NO:43) or an active portion thereof; AGCAUAGCAAGUUAAAAUAAGGCUAGUCCGUUAUCAACUUGAAAAAGU GGCACCGAGUCGGUGC (SEQ ID NO:17) or an active portion thereof; UAGCAAGUUAAAAUAAGGCUAGUCCGUUAUCAACUUGAAAAAGUG (SEQ ID NO:44) or an active portion thereof; UAGCAAGUUAAAAUAAGGCUAGUCCGUUAUCA (SEQ ID NO:45) or an active portion thereof; or UAGCAAGUUAAAAUAAGGCUAGUCCG (SEQ ID NO:45) or an active portion thereof; and (a) a crRNA that includes or more deoxyribonuclotides (e.g., wherein the sequence may also be partially or wholly DNA but with thymine in place or uracil), e.g., wherein the target complementarity region is at least partially or wholly DNA, e.g., a crRNA that includes a sequence of 17-20 nucleotides that are complementary to a target sequence, preferably a target sequence immediately 5' of a protospacer adjacent motif (PAM), e.g., NGG, NAG, or NNGG, wherein the crRNA includes one or more deoxyribonuclotides (e.g., where the defined sequence may also be partially or wholly DNA but with thymine in place or uracil), e.g., wherein the crRNA consists of the sequence: 5'-$X_{17\text{-}20}$GUUUUAGAGCUAUGCUGUUUUG($X_N$)-3' (SEQ ID NO:46); ($X_{17\text{-}20}$)GUUUUAGAGCUA (SEQ ID NO:5); ($X_{17\text{-}20}$) GUUUUAGAGCUAUGCUGUUUUG (SEQ ID NO:6); or ($X_{17\text{-}20}$)GUUUUAGAGCUAUGCU (SEQ ID NO:7); where the $X_{17\text{-}20}$ is at least partially or wholly DNA and is a sequence complementary to 17-20 consecutive nucleotides of a target sequence; or (b) a crRNA that includes one or more nucleotides that are modified, e.g., locked (2'-O-4'-C methylene bridge), is 5'-methylcytidine, is 2'-O-methyl-pseudouridine, or in which the ribose phosphate backbone has been replaced by a polyamide chain, e.g., wherein one or more of the nucleotides in the target complementarity region is modified, e.g., a crRNA that includes a sequence of 17-20 nucleotides that are complementary to a target sequence, preferably a target sequence immediately 5' of a protospacer adjacent motif (PAM), e.g., NGG, NAG, or NNGG, wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., wherein the crRNA consists of the sequence: 5'-$X_{17\text{-}20}$GUUUUAGAGCUAUGCUGUUUUG($X_N$)-3' (SEQ ID NO:46); ($X_{17\text{-}20}$) GUUUUAGAGCUA (SEQ ID NO:5); ($X_{17\text{-}20}$)GUUUUAGAGCUAUGCUGUUUUG (SEQ ID NO:6); or ($X_{17\text{-}20}$) GUUUUAGAGCUAUGCU (SEQ ID NO:7); where one or more of the $X_{17\text{-}20}$ wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain. In no case is the $X_{17\text{-}20}$ identical to a sequence that naturally occurs adjacent to the rest of the RNA. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In some embodiments wherein ($X_{17\text{-}20}$)GUUUUAGAGCUAUGCUGUUUUG (SEQ ID NO:6) is used as a crRNA, the following tracrRNA is used: GGAACCAUUCAAAACAGCAUAGCAAGUUAAAAUAAGGCUAGUCCGUUA UCAACUUGAAAAAGUGGCACCGAGUCGGUGC (SEQ ID NO:8) or an active portion thereof. In some embodiments wherein ($X_{17\text{-}20}$)GUUUUAGAGCUA (SEQ ID NO:5) is used as a crRNA, the following tracrRNA is used: UAGCAAGUUAAAAUAAGGCUAGUCCGUUAUCAACUUGAAAAAGUGGCA CCGAGUCGGUGC (SEQ ID NO:16) or an active portion thereof. In some embodiments wherein ($X_{17\text{-}20}$) GUUUUAGAGCUAUGCU (SEQ ID NO:4) is used as a crRNA, the following tracrRNA is used: AGCAUAGCAAGUUAAAAUAAGGCUAGUCCGUUAUCAACUUGAAAAAGU GGCACCGAGUCGGUGC (SEQ ID NO:17) or an active portion thereof.

In yet another aspect, the invention provides methods for sequence-specifically inducing a pair of nicks in a double-stranded DNA molecule, e.g., in a genomic sequence in a cell. The methods include expressing in the cell, or introducing into the cell or contacting the cell with, a Cas9-nickase as known in the art or described herein, and:

(a) two guide RNAs, wherein one of the two guide RNAs includes sequence that is complementary to one strand of the target sequence and the second of the two guide RNAS includes sequence that is complementary to the other strand of the target sequence, such that using both guide RNAs results in targeting both strands, and the Cas9-nickase results in cuts being introduced into each strand; or (b) a tracrRNA and two crRNAs wherein one of the two crRNAs includes sequence that is complementary to one strand of the target sequence and the second of the two crRNAs is complementary to the other strand of the target sequence, such that using both crRNAs results in targeting both strands, and the Cas9-nickase cuts each strand.

In some embodiments, the method includes contacting the cell with two nickases, wherein the first nickase comprises a Cas9 with a mutation at D10, E762, H983, or D986 and the second nickase comprises a Cas9 with a mutation at H840 or N863.

In some embodiments wherein $(X_{17-20})$GUUUUA-GAGCUAUGCUGUUUUG (SEQ ID NO:6) is used as a crRNA, the following tracrRNA is used: GGAACCAUUCAAAACAGCAUAG-CAAGUUAAAAUAAGGCUAGUCCGUUA UCAAC-UUGAAAAAGUGGCACCGAGUCGGUGC (SEQ ID NO:8) or an active portion thereof. In some embodiments wherein $(X_{17-20})$GUUUUAGAGCUA (SEQ ID NO:5) is used as a crRNA, the following tracrRNA is used: UAGCAAGUUAAAAUAAGGCUAGUCCGUUAU-CAACUUGAAAAAGUGGCA CCGAGUCGGUGC (SEQ ID NO:16) or an active portion thereof. In some embodiments wherein $(X_{17-20})$ GUUUUAGAGCUAUGCU (SEQ ID NO:4) is used as a crRNA, the following tracrRNA is used: AGCAUAGCAAGUUAAAAUAAGGCUAGUC-CGUUAUCAACUUGAAAAAGU GGCACCGAGUCG-GUGC (SEQ ID NO:17) or an active portion thereof.

In an additional aspect, the invention provides three-part fusion guide nucleic acid comprising, in any order that preserves activity of each part: (1) a first sequence that is complementary to the complementary strand of a target genomic sequence, e.g., a first sequence of 17-20 or 17-25 consecutive nucleotides that is complementary to 17-20 or 17-25 consecutive nucleotides of the complementary strand of a target sequence; (2) a second sequence comprising all or part of a Cas9 guide RNA that forms a stem-loop sequence that is recognized by and binds to Cas9; and (3) a third sequence that binds to an RNA binding protein, e.g., MS2, CRISPR/Cas Subtype Ypest protein 4 (Csy4), or lambda N. In some embodiments, the first and second sequences comprise:
$(X_{17-20})$ GUUUUAGAGCUAUGCUGUUUUG$(X_N)$ (SEQ ID NO:4);
$(X_{17-20})$GUUUUAGAGCUA (SEQ ID NO:5);
$(X_{17-20})$ GUUUUAGAGCUAUGCUGUUUUG (SEQ ID NO:6);
$(X_{17-20})$GUUUUAGAGCUAUGCU (SEQ ID NO:7);
$(X_{17-20})$GUUUUAGAGCUAGAAAUAG-CAAGUUAAAAUAAGGCUAGUCCG$(X_N)$ (SEQ ID NO:8);
$(X_{17-20})$GUUUUAGAGCUAUGCUGAAAAGCAUAG-CAAGUUAAAAUAAGGCU AGUCCGUUAUC$(X_N)$ (SEQ ID NO:9);
$(X_{17-20})$GUUUUAGAGCUAUGCUGUUUUG-GAAACAAAACAGCAUAGCAAGU UAAAAUAAGGCUAGUCCGUUAUC$(X_N)$ (SEQ ID NO:10);
$(X_{17-20})$GUUUUAGAGCUAGAAAUAG-CAAGUUAAAAUAAGGCUAGUCCGUU AUCAAC-UUGAAAAAGUGGCACCGAGUCGGUGC$(X_N)$ (SEQ ID NO:11),
$(X_{17-20})$GUUUAAGAGCUAGAAAUAG-CAAGUUUAAAUAAGGCUAGUCCGUU AUCAAC-UUGAAAAAGUGGCACCGAGUCGGUGC(SEQ ID NO:12);
$(X_{17-20})$GUUUUAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:13); or
$(X_{17-20})$GUUUAAGAGCUAUGCUGGAAACAG-CAUAGCAAGUUAAAUAAGG CUAGUCCGUUAU-CAACUUGAAAAGUGGCACCGAGUCGGUGC (SEQ ID NO:14), wherein $X_{17-20}$ is a sequence complementary to 17-20 nts of a target sequence. In no case is the $X_N$ identical to a sequence that naturally occurs adjacent to the rest of the RNA. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In yet another aspect, the invention provides tracrRNA molecule comprising a sequence GUUUUAGAGCUAGAAAUAG-CAAGUUAAAAUAAGGCUAGUCCGUUAUCA ACUUGAAAAAGUGGCACCGAGTCGGUGCUUUU (SEQ ID NO:15) or an active portion thereof, UAGCAAGUUAAAAUAAGGCUAGUCCGUUAU-CAACUUGAAAAAGUGGCA CCGAGUCGGUGC (SEQ ID NO:16) or an active portion thereof; or AGCAUAGCAAGUUAAAAUAAGGCUAGUC-CGUUAUCAACUUGAAAAAGU GGCACCGAGUCG-GUGC (SEQ ID NO:17) or an active portion thereof, linked to a sequence that binds to an RNA binding protein, e.g., MS2, Csy4 (e.g., GUUCACUGCCGUAUAGGCAG or GUUCACUGCCGUAUAGGCAGCUAAGAAA), or lambda N. In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. Additional exemplary tracrRNA sequences include: GGAACCAUUCAAAACAGCAUAG-CAAGUUAAAAUAAGGCUAGUCCGUUA UCAAC-UUGAAAAAGUGGCACCGAGUCGGUGC (SEQ ID NO:42) or an active portion thereof; UAGCAAGUUAAAAUAAGGCUAGUCCGUUAU-CAACUUGAAAAAGUGGCA CCGAGUCGGUGC (SEQ ID NO:16) or an active portion thereof; CAAAACAGCAUAGCAAGUUAAAAUAAGGCUAGU-CCGUUAUCAACUUGA AAAAGUGGCACCGAGUCG-GUGC (SEQ ID NO:43) or an active portion thereof; AGCAUAGCAAGUUAAAAUAAGGCUAGUC-CGUUAUCAACUUGAAAAAGU GGCACCGAGUCG-GUGC (SEQ ID NO:17) or an active portion thereof; UAGCAAGUUAAAAUAAGGCUAGUCCGUUAU-CAACUUGAAAAAGUG (SEQ ID NO:44) or an active portion thereof; UAGCAAGUUAAAAUAAGGCUAGUCCGUUAUCA (SEQ ID NO:45) or an active portion thereof; or UAGCAAGUUAAAAUAAGGCUAGUCCG (SEQ ID NO:45) or an active portion thereof.

In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In some embodiments wherein (X$_{17-20}$)GUUUUA-GAGCUAUGCUGUUUUG (SEQ ID NO:6) is used as a crRNA, the following tracrRNA is used: GGAACCAUUCAAAACAGCAUAG-CAAGUUAAAAUAAGGCUAGUCCGUUA UCAAC-UUGAAAAAGUGGCACCGAGUCGGUGC (SEQ ID NO:8) or an active portion thereof. In some embodiments wherein (X$_{17-20}$)GUUUUAGAGCUA (SEQ ID NO:5) is used as a crRNA, the following tracrRNA is used: UAGCAAGUUAAAAUAAGGCUAGUCCGUUAU-CAACUUGAAAAAGUGGCA CCGAGUCGGUGC (SEQ ID NO:16) or an active portion thereof. In some embodiments wherein (X$_{17-20}$) GUUUUAGAGCUAUGCU (SEQ ID NO:4) is used as a crRNA, the following tracrRNA is used: AGCAUAGCAAGUUAAAAUAAGGCUAGUC-CGUUAUCAACUUGAAAAAGU GGCACCGAGUCG-GUGC (SEQ ID NO:17) or an active portion thereof.

In another aspect, the invention provides DNA molecules encoding the three-part fusion guide nucleic acids or the tracrRNA described herein.

In yet another aspect, the invention provides fusion proteins comprising an RNA binding protein, e.g., MS2, Csy4, or lambda N, linked to a catalytic domain of a FokI nuclease or to a heterologous functional domain (HFD) as described herein, optionally with an intervening linker of 2-30, e.g., 5-20 nts, and DNA molecules encoding the fusion proteins. In some embodiment, the fusion protein comprises a FokI catalytic domain sequence fused to the N terminus of Csy4, with an intervening linker, optionally a linker of from 2-30 amino acids, e.g., 4-12 amino acids, e.g., Gly$_4$Ser, (Gly$_4$Ser)$_{1-5}$. In some embodiments the HFD modifies gene expression, histones, or DNA, e.g., transcriptional activation domain, transcriptional repressors (e.g., silencers such as Heterochromatin Protein 1 (HP1), e.g., HP1α or HP1β, or a transcriptional repression domain, e.g., Krueppel-associated box (KRAB) domain, ERF repressor domain (ERD), or mSin3A interaction domain (SID)), enzymes that modify the methylation state of DNA (e.g., DNA methyltransferase (DNMT) or Ten-Eleven Translocation (TET) proteins, e.g., TET1, also known as Tet Methylcytosine Dioxygenase 1), or enzymes that modify histone subunit (e.g., histone acetyltransferases (HAT), histone deacetylases (HDAC), or histone methyltransferase or histone demethylases).

In a further aspect, the invention provides methods for sequence-specifically inducing a break in a double-stranded DNA molecule, e.g., in a genomic sequence in a cell. The methods include expressing in the cell, or contacting the cell with a fusion protein comprising an RNA binding protein, e.g., MS2, Csy4, or lambda N, linked to a catalytic domain of a FokI nuclease, optionally with an intervening linker of 2-30, e.g., 5-20 nts,
a dCas9 protein; and
(a) a three-part fusion guide nucleic acid described herein,
(b) a tracrRNA as described herein, and a crRNA suitable for use with the tracrRNA; and/or
(c) a DNA molecule encoding a three-part fusion guide nucleic acid or tracrRNA as described herein.

In yet another aspect, the invention provides vectors comprising the DNA molecules described herein, and host cells expressing the vectors.

In an additional aspect, the invention provides methods for modifying a target region of a double-stranded DNA molecule, e.g., in a genomic sequence in a cell. The methods include expressing in or introducing into the cell:
a dCas9-heterologous functional domain fusion protein (dCas9-HFD); and (a) a guide RNA that includes one or more deoxyribonuclotides (e.g., where the sequence may also be partially or wholly DNA but with thymine in place or uracil), e.g., a guide RNA that includes a sequence of 17-20 nucleotides that are complementary to the complementary strand of a target sequence, preferably a target sequence immediately 5' of a protospacer adjacent motif (PAM), e.g., NGG, NAG, or NNGG, wherein the guide RNA includes one or more deoxyribonuclotides (e.g., where the defined sequence may also be partially or wholly DNA but with thymine in place or uracil), e.g., hybrid nucleic acid as described herein; or
(b) a guide RNA wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., a guide RNA that includes a sequence of 17-20 nucleotides that are complementary to the complementary strand of a target sequence, preferably a target sequence immediately 5' of a protospacer adjacent motif (PAM), e.g., NGG, NAG, or NNGG, wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., a synthetic ribonucleic acid as described herein. In no case is the X$_{17-20}$ identical to a sequence that naturally occurs adjacent to the rest of the RNA. In some embodiments the RNA includes one or more, e.g., up to 3, e.g., one, two, or three, additional nucleotides at the 5' end of the RNA molecule that is not complementary to the target sequence.

In another aspect, the invention provides methods for modifying a target region of a double-stranded DNA molecule, e.g., in a genomic sequence in a cell. The methods include expressing in or introducing into the cell:
a dCas9-heterologous functional domain fusion protein (dCas9-HFD);
a tracrRNA, e.g., comprising the sequence of tracrRNA molecule comprising a sequence GUUUUAGAGCUA-GAAAUAGCAAGUUAAAAUAAGGCUAGUC-CGUUAUCA ACUUGAAAAAGUGGCACCGAGTCG-GUGCUUUU (SEQ ID NO:15) or an active portion thereof, UAGCAAGUUAAAAUAAGGCUAGUCCGUUAU-CAACUUGAAAAAGUGGCA CCGAGUCGGUGC (SEQ ID NO:16) or an active portion thereof; or AGCAUAG-CAAGUUAAAAUAAGGCUAGUCCGUUAUCAAC-UUGAAAAAGU GGCACCGAGUCGGUGC (SEQ ID NO:17) or an active portion thereof; and
(a) a crRNA that includes or more deoxyribonuclotides (e.g., wherein the sequence may also be partially or wholly DNA but with thymine in place or uracil), e.g., wherein the target complementarity region is at least partially or wholly DNA, e.g., a crRNA that includes a sequence of 17-20 nucleotides that are complementary to the complementary strand of a target sequence, preferably a target sequence immediately 5' of a protospacer adjacent motif (PAM), e.g., NGG, NAG, or NNGG, wherein the crRNA includes one or more deoxyribonuclotides (e.g., where the defined sequence may also be partially or wholly DNA but with thymine in place or uracil), e.g., wherein the crRNA consists of the sequence:
5'-X$_{17-20}$GUUUUAGAGCUAUGCUGUUUUG(X$_N$)-3' (SEQ ID NO:46);
(X$_{17-20}$)GUUUUAGAGCUA (SEQ ID NO:5);
(X$_{17-20}$)GUUUUAGAGCUAUGCUGUUUUG (SEQ ID NO:6); or ($X_{17-20}$)GUUUUAGAGCUAUGCU (SEQ ID NO:7); where the $X_{17-20}$ is at least partially or wholly DNA and is a sequence complementary to 17-20 consecutive nucleotides of a target sequence; or (b) a crRNA that includes one or more nucleotides that are modified, e.g., locked (2'-O-4'-C methylene bridge), is 5'-methylcytidine, is 2'-O-methyl-pseudouridine, or in which the ribose phosphate backbone has been replaced by a polyamide chain, e.g., wherein one or more of the nucleotides in the target complementarity region is modified, e.g., a crRNA that includes a sequence of 17-20 nucleotides that are complementary to the complementary strand of a target sequence, preferably a target sequence immediately 5' of a protospacer adjacent motif (PAM), e.g., NGG, NAG, or NNGG, wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., wherein the crRNA consists of the sequence:
5'-$X_{17-20}$GUUUUAGAGCUAUGCUGUUUUG($X_N$)-3' (SEQ ID NO:46);
($X_{17-20}$)GUUUUAGAGCUA (SEQ ID NO:5);
($X_{17-20}$)GUUUUAGAGCUAUGCUGUUUUG (SEQ ID NO:6); or
($X_{17-20}$)GUUUUAGAGCUAUGCU (SEQ ID NO:7); where one or more of the $X_{17-20}$ wherein one or more of the nucleotides is modified, e.g., locked (2'-O-4'-C methylene bridge), is 5'-methylcytidine, is 2'-O-methyl-pseudouridine, or in which the ribose phosphate backbone has been replaced by a polyamide chain. In no case is the $X_{17-20}$ identical to a sequence that naturally occurs adjacent to the rest of the RNA. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, additional nucleotides at the 5' end of the RNA molecule that is not complementary to the target sequence.

In some embodiments, the dCas9-heterologous functional domain fusion protein (dCas9-HFD) comprises a HFD that modifies gene expression, histones, or DNA, e.g., transcriptional activation domain, transcriptional repressors (e.g., silencers such as Heterochromatin Protein 1 (HP1), e.g., HP1α or HP1β, or a transcriptional repression domain, e.g., Krueppel-associated box (KRAB) domain, ERF repressor domain (ERD), or mSin3A interaction domain (SID)), enzymes that modify the methylation state of DNA (e.g., DNA methyltransferase (DNMT) or Ten-Eleven Translocation (TET) proteins, e.g., TET1, also known as Tet Methylcytosine Dioxygenase 1), or enzymes that modify histone subunit (e.g., histone acetyltransferases (HAT), histone deacetylases (HDAC), or histone methyltransferase or histone demethylases). In some embodiments, the heterologous functional domain is a transcriptional activation domain, e.g., a transcriptional activation domain from VP64 or NF-κB p65; an enzyme that catalyzes DNA demethylation, e.g., a TET; or histone modification (e.g., LSD1, histone methyltransferase, HDACs, or HATs) or a transcription silencing domain, e.g., from Heterochromatin Protein 1 (HP1), e.g., HP1α or HP1β; or a biological tether, e.g., CRISPR/Cas Subtype Ypest protein 4 (Csy4), MS2, or lambda N protein. Cas9-HFD are described in a U.S. Provisional Patent Application Ser. No. 61/799,647, Filed on Mar. 15, 2013, U.S. Ser. No. 61/838,148, filed on Jun. 21, 2013, and PCT International Application No. PCT/US14/27335, all of which are incorporated herein by reference in its entirety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

```
                                         SEQ ID NO: 1
    EGFP Site 1 GGGCACGGGCAGCTTGCCGGTGG SEQ ID NO: 2
    EGFP Site 2 GATGCCGTTCTTCTGCTTGTCGG SEQ ID NO: 3
    EGFP Site 3 GGTGGTGCAGATGAACTTCAGGG
```

Figure 2A:
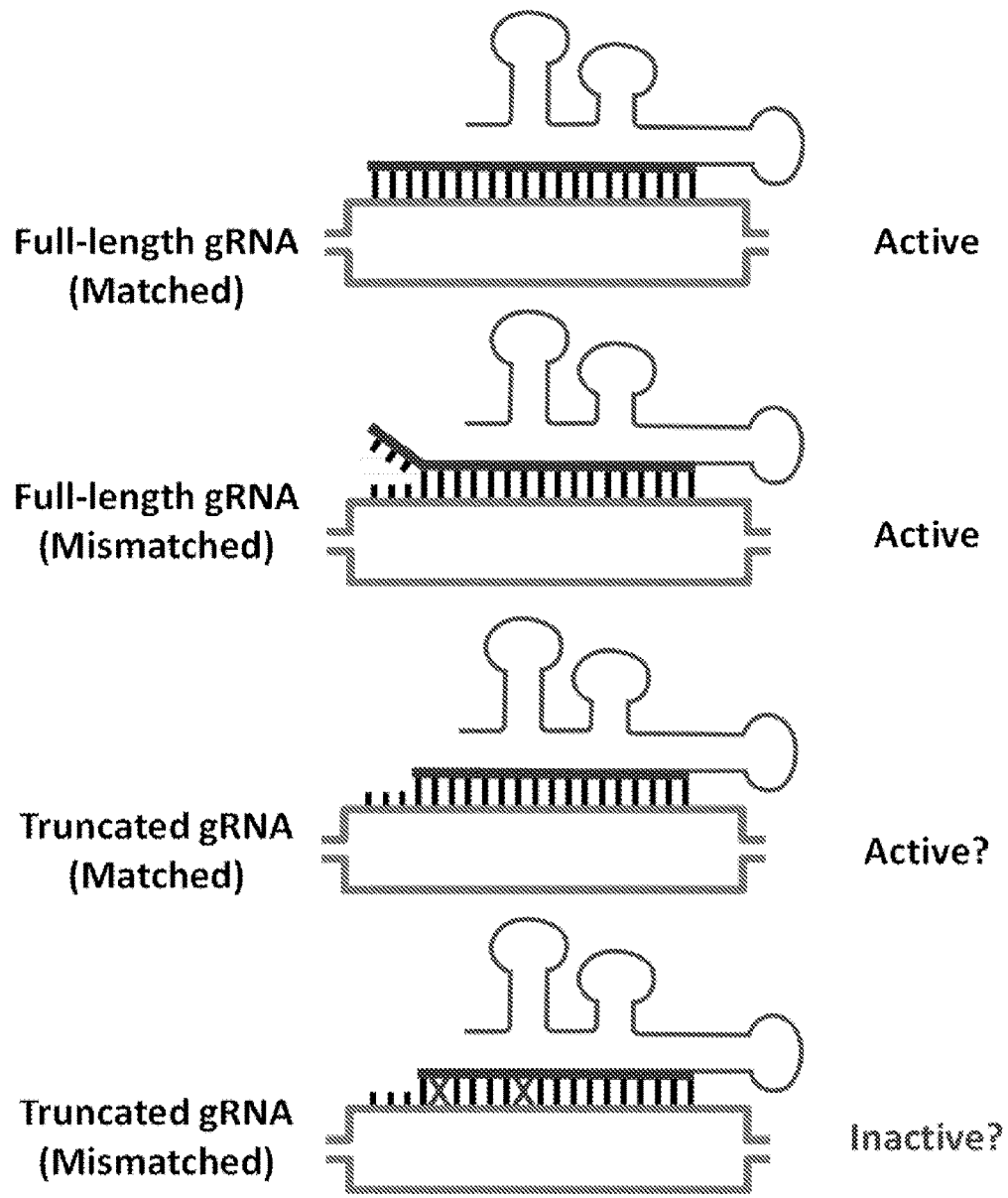
FIG. 2A: Schematic illustrating the rationale for truncating the 5' complementarity region of a gRNA. Thick black lines=target DNA site, line structure=gRNA, grey oval=Cas9 nuclease, black lines indicate base pairing between gRNA and target DNA site.
Figure 2B:
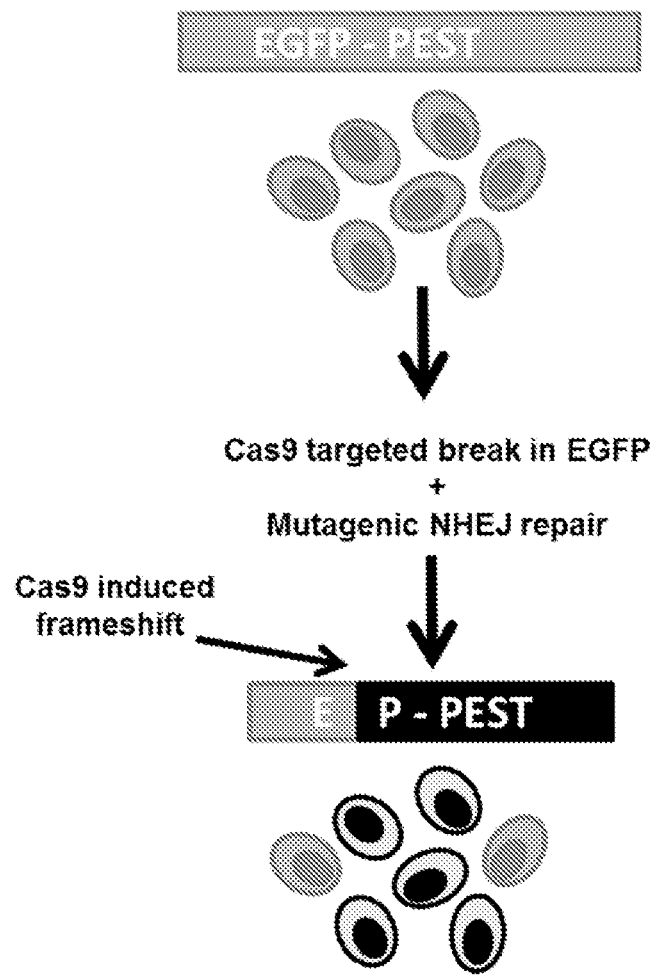
FIG. 2B: Schematic overview of the EGFP disruption assay. Repair of targeted Cas9-mediated double-stranded breaks in a single integrated EGFP-PEST reporter gene by error-prone NHEJ-mediated repair leads to frame-shift mutations that disrupt the coding sequence and associated loss of fluorescence in cells.
Figure 2C:
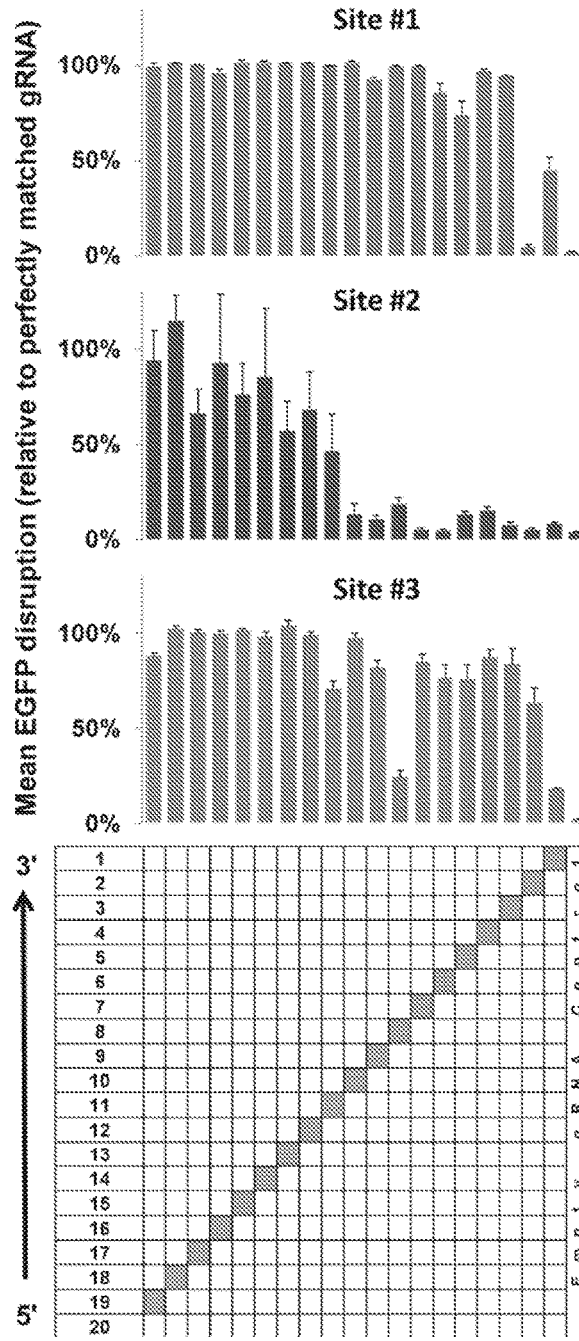
FIGS. 2C-F: Activities of CRISPR RNA-guided nucleases (RGNs) with gRNAs bearing (C) single mismatches, (D) adjacent double mismatches, (E) variably spaced double mismatches, and (F) increasing numbers of adjacent mismatches assayed on three different target sites in the EGFP reporter gene sequence. Mean activities of replicates (see Online Methods) are shown, normalized to the activity of a perfectly matched gRNA. Error bars indicate standard errors of the mean. Positions mismatched in each gRNA are highlighted in grey in the grid below. Sequences of the three EGFP target sites were as follows.
Figure 2D:
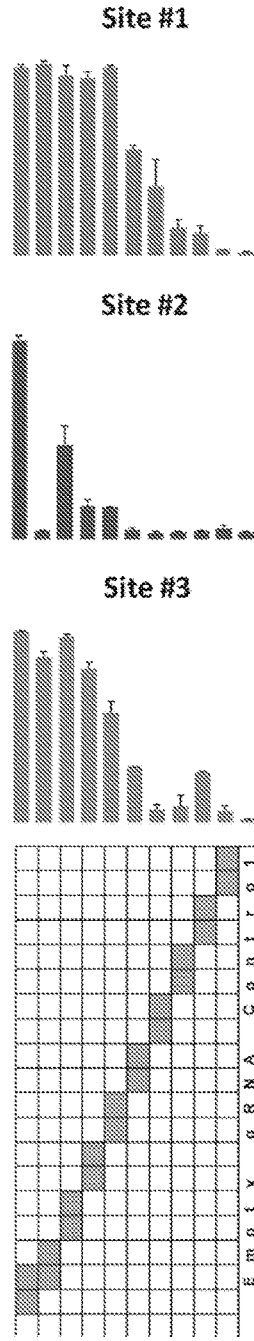
Figure 2E:
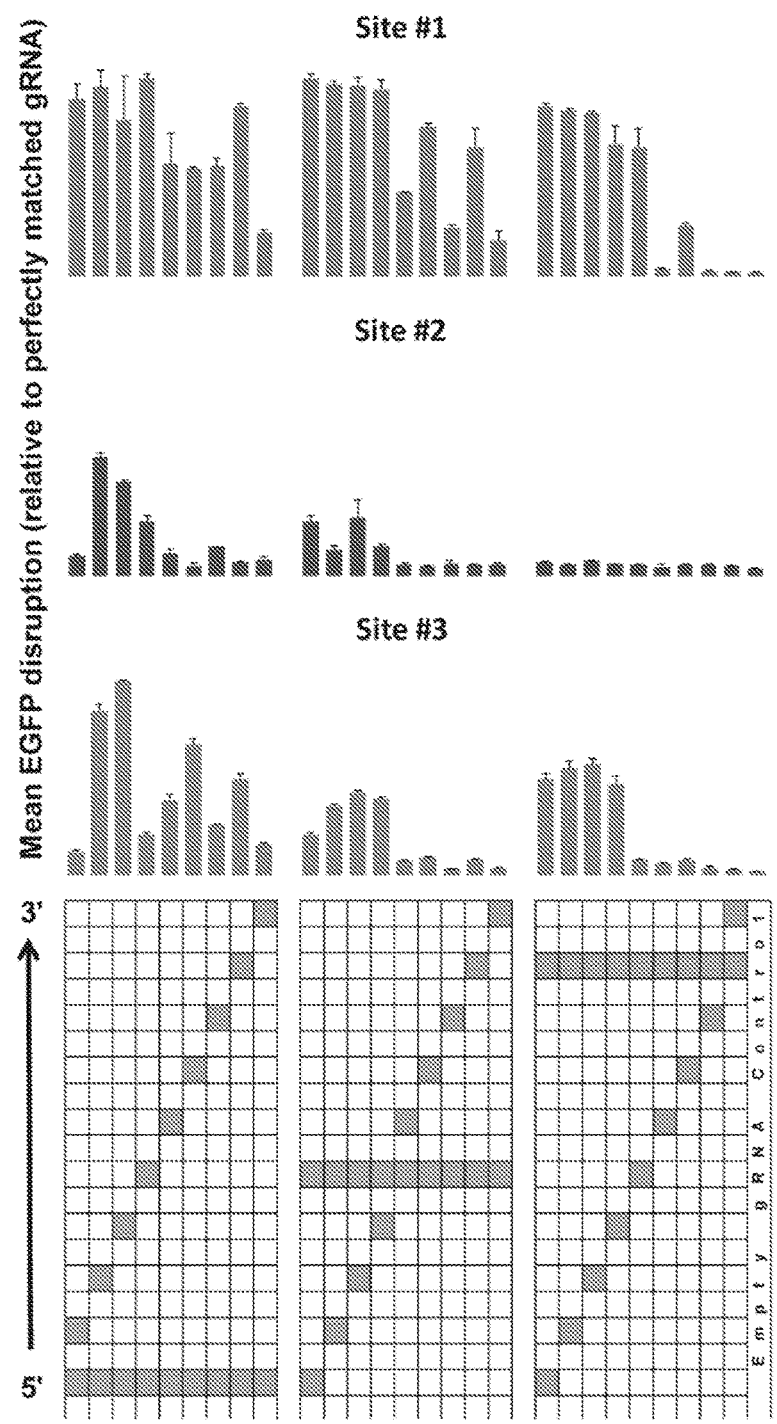
Figure 2F:
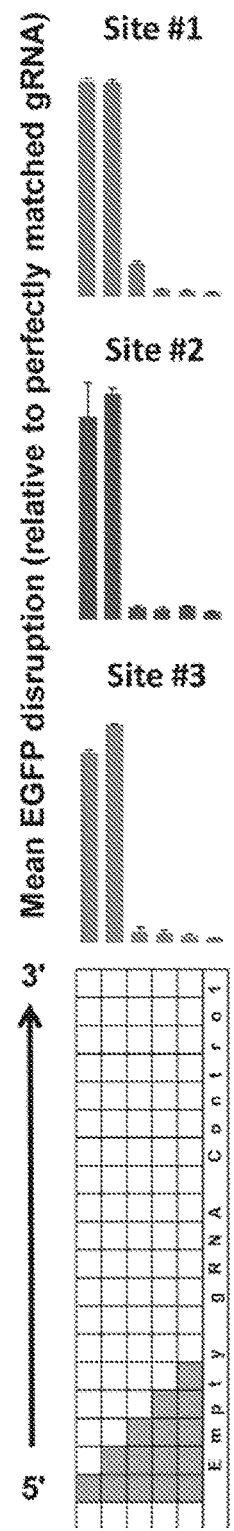
Figure 2G:
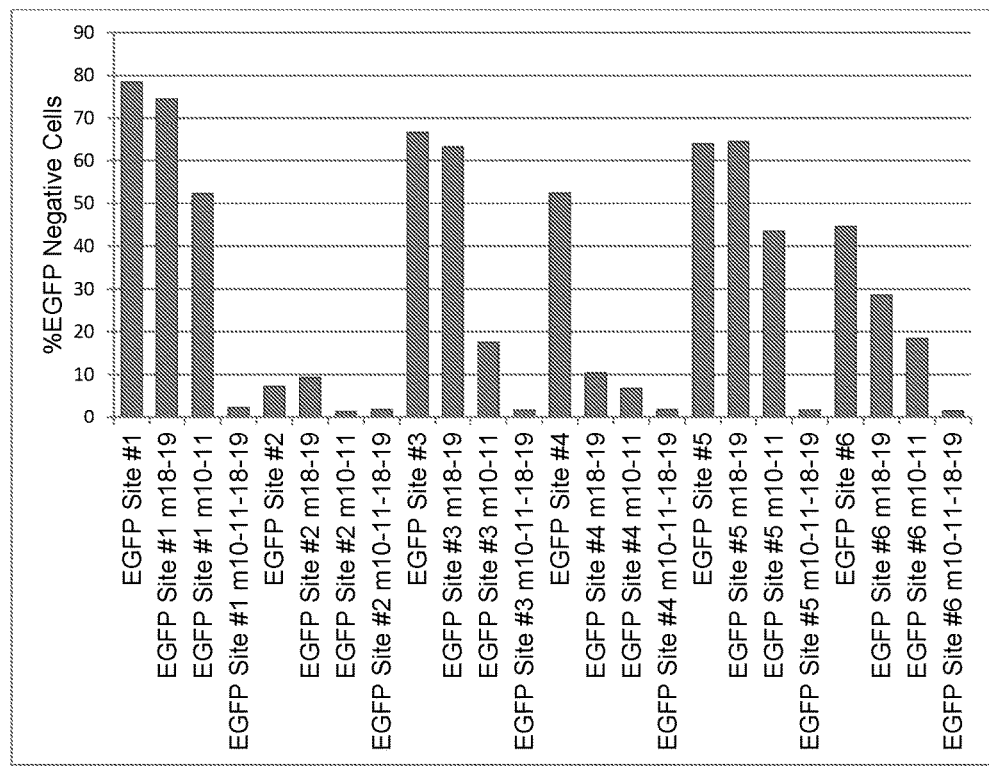

FIG. 2G: Mismatches at the 5' end of the gRNA make CRISPR/Cas more sensitive more 3' mismatches. The gRNAs Watson-Crick base pair between the RNA&DNA with the exception of positions indicated with an "m" which are mismatched using the Watson-Crick transversion (i.e. EGFP Site#2 M18-19 is mismatched by changing the gRNA to its Watson-Crick partner at positions 18 & 19. Although positions near the 5' of the gRNA are generally very well tolerated, matches in these positions are important for nuclease activity when other residues are mismatched. When all four positions are mismatched, nuclease activity is no longer detectable. This further demonstrates that matches at these 5' position can help compensate for mismatches at other more 3' positions. Note these experiments were performed with a non-codon optimized version of Cas9 which can show lower absolute levels of nuclease activity as compared to the codon optimized version.

Figure 2H:
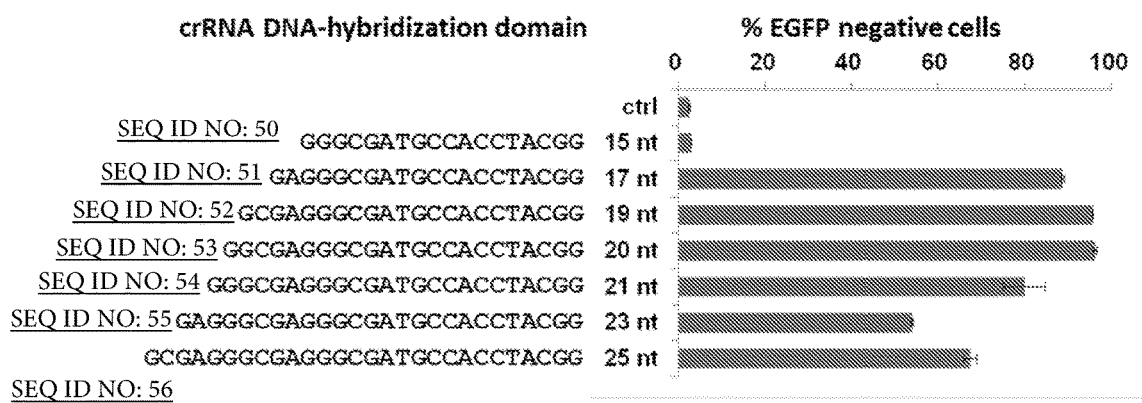

FIG. 2H: Efficiency of Cas9 nuclease activities directed by gRNAs bearing variable length complementarity regions ranging from 15 to 25 nts in a human cell-based U2OS EGFP disruption assay. Expression of a gRNA from the U6 promoter requires the presence of a 5' G and therefore it was only possible to evaluate gRNAs harboring certain lengths of complementarity to the target DNA site (15, 17, 19, 20, 21, 23, and 25 nts).

Figure 3A:
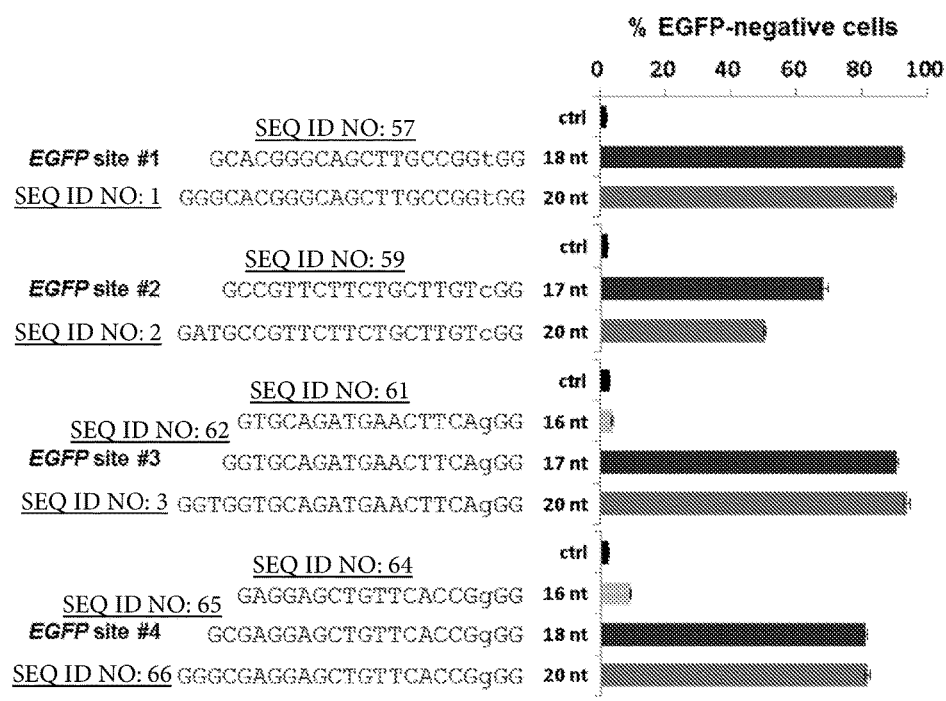

FIG. 3A: Efficiencies of EGFP disruption in human cells mediated by Cas9 and full-length or shortened gRNAs for four target sites in the EGFP reporter gene. Lengths of complementarity regions and corresponding target DNA sites are shown. Ctrl=control gRNA lacking a complementarity region.

Figure 3B:
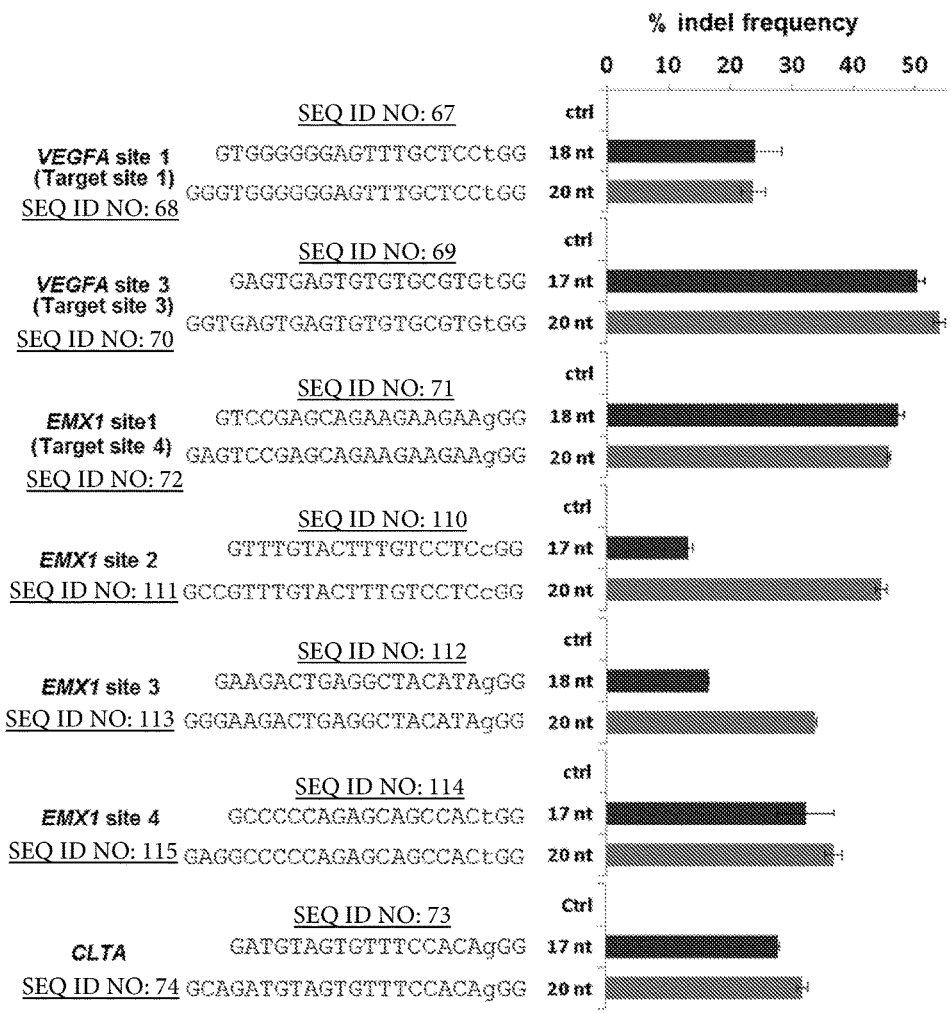

FIG. 3B: Efficiencies of targeted indel mutations introduced at seven different human endogenous gene targets by matched standard and tru-RGNs. Lengths of complementarity regions and corresponding target DNA sites are shown. Indel frequencies were measured by T7EI assay. Ctrl=control gRNA lacking a complementarity region.

FIG. 3C: DNA sequences of indel mutations induced by RGNs using a tru-gRNA or a matched full-length gRNA targeted to the EMX1 site. The portion of the target DNA site that interacts with the gRNA complementarity region is highlighted in grey with the first base of the PAM sequence shown in lowercase. Deletions are indicated by dashes highlighted in grey and insertions by italicized letters highlighted in grey. The net number of bases deleted or inserted and the number of times each sequence was isolated are shown to the right.

Figure 3D:
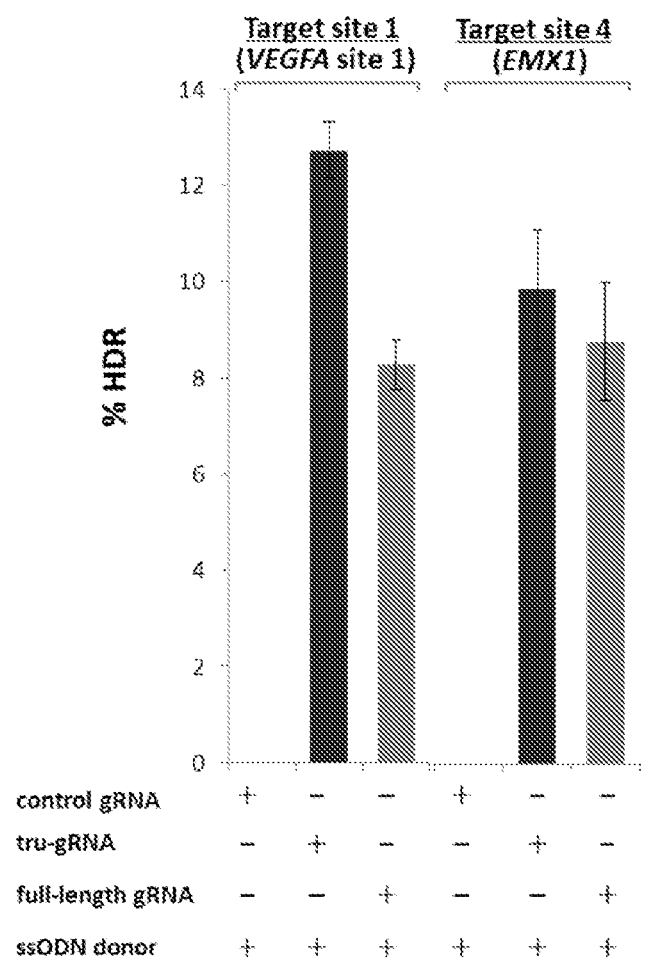

FIG. 3D: Efficiencies of precise HDR/ssODN-mediated alterations introduced at two endogenous human genes by matched standard and tru-RGNs. % HDR was measured using a BamHI restriction digest assay (see the Experimental Procedures for Example 2). Control gRNA=empty U6 promoter vector.

FIG. 3E: U2OS.EGFP cells were transfected with variable amounts of full-length gRNA expression plasmids (top) or tru-gRNA expression plasmids (bottom) together with a fixed amount of Cas9 expression plasmid and then assayed for percentage of cells with decreased EGFP expression. Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites.

FIG. 3F: U2OS.EGFP cells were transfected with variable amount of Cas9 expression plasmid together with variable amounts of full-length gRNA expression plasmids (top) or tru-gRNA expression plasmids (bottom) (amounts determined for each tru-gRNA from the experiments of FIG. 3E). Mean values from duplicate experiments are shown with standard errors of the mean. Note that the data obtained with tru-gRNA matches closely with data from experiments performed with full-length gRNA expression plasmids instead of tru-gRNA plasmids for these three EGFP target sites. The results of these titrations determined the concentrations of plasmids used in the EGFP disruption assays performed in Examples 1 and 2.

Figure 4:
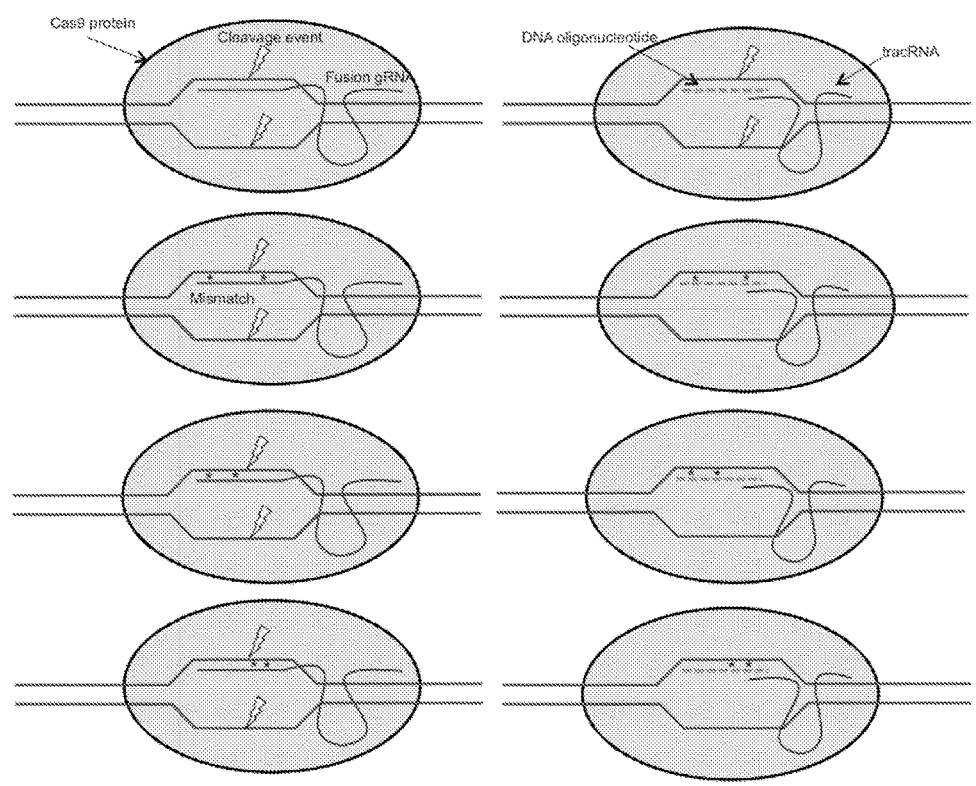

FIG. 4: Schematic representation of gRNA-guided RGN and DNA-guided Cas9 nuclease. The gRNA fusion RNA molecule can bind to both its on-target sequence (no asterisks) and a wide range of off-target sites (mismatches denoted by asterisks) and induce DNA cleavage. Because of the increased sensitivity of DNA-DNA duplexes to mismatches, a DNA-guided Cas9 nuclease system that uses a short DNA oligonucleotide with complementarity to a tracRNA may no longer be able to bind and cut at off-target sites, but may still function in genomic localization of Cas9. This may lead to a marked increase in Cas9-mediated nuclease activity over traditional RGNs.

Figure 5:
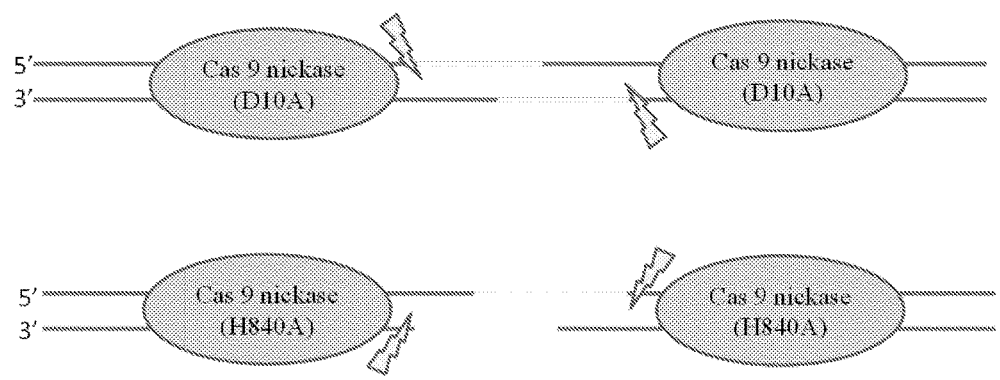

FIG. 5: Pairs of Cas9 RNA-guided nickases used to create paired nicks on opposing strands of DNA FIG. 6: Schematic illustrating recruitment of two RNA-binding protein-FokI nuclease domain fusions to the DNA (see text for details).

FIG. 7A: Variant gRNAs bearing a Csy4 binding site can function to recruit Cas9 to specific sites in human cells.

FIG. 7B: Three-part complex of catalytically inactive Cas9 nuclease (dCas9), gRNA with Csy4 recognition site, and FokI-Csy4 fusion. Protospacer adjacent motif (PAM) sequences are facing 'outward' in this configuration.

Figure 7C:
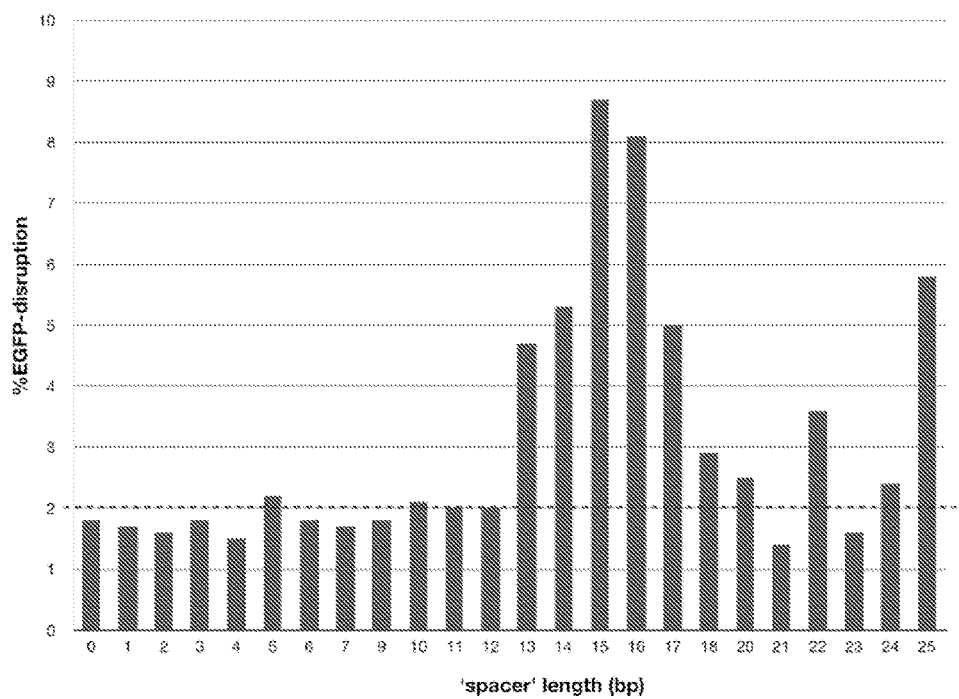

FIG. 7C: dCas9/gRNA/FokI-Csy4 pairs with spacer lengths of 15-16 bp showing the highest level of activity in an EGFP-disruption assay.

FIG. 7D: T7 endonuclease I assay showing molecular evidence of non-homologous end joining-mediated DNA double-stranded break repair in dCas9/gRNA/FokI-Csy4 treated samples, but not in negative controls.

DETAILED DESCRIPTION

CRISPR RNA-guided nucleases (RGNs) have rapidly emerged as a facile and efficient platform for genome editing. Although Marraffini and colleagues (Jiang et al., Nat Biotechnol 31, 233-239 (2013)) recently performed a systematic investigation of Cas9 RGN specificity in bacteria, the specificities of RGNs in human cells have not been extensively defined. Understanding the scope of RGN-mediated off-target effects in human and other eukaryotic cells will be critically essential if these nucleases are to be used widely for research and therapeutic applications. The present inventors have used a human cell-based reporter assay to characterize off-target cleavage of Cas9-based RGNs. Single and double mismatches were tolerated to varying degrees depending on their position along the guide RNA (gRNA)-DNA interface. Off-target alterations induced by four out of six RGNs targeted to endogenous loci in human cells were readily detected by examination of partially mismatched sites. The off-target sites identified harbor up to five mismatches and many are mutagenized with frequencies comparable to (or higher than) those observed at the intended on-target site. Thus RGNs are highly active even with imperfectly matched RNA-DNA interfaces in human cells, a finding that might confound their use in research and therapeutic applications.

The results described herein reveal that predicting the specificity profile of any given RGN is neither simple nor straightforward. The EGFP reporter assay experiments show that single and double mismatches can have variable effects on RGN activity in human cells that do not strictly depend upon their position(s) within the target site. For example, consistent with previously published reports, alterations in the 3' half of the gRNA/DNA interface generally have greater effects than those in the 5' half (Jiang et al., Nat Biotechnol 31, 233-239 (2013); Cong et al., Science 339, 819-823 (2013); Jinek et al., Science 337, 816-821 (2012)); however, single and double mutations in the 3' end sometimes also appear to be well tolerated whereas double mutations in the 5' end can greatly diminish activities. In addition, the magnitude of these effects for mismatches at any given position(s) appears to be site-dependent. Comprehensive profiling of a large series of RGNs with testing of all possible nucleotide substitutions (beyond the Watson-Crick transversions used in our EGFP reporter experiments) may help provide additional insights into the range of potential off-targets. In this regard, the recently described bacterial cell-based method of Marraffini and colleagues (Jiang et al., Nat Biotechnol 31, 233-239 (2013)) or the in vitro, combinatorial library-based cleavage site-selection methodologies previously applied to ZFNs by Liu and colleagues (Pattanayak et al., Nat Methods 8, 765-770 (2011)) might be useful for generating larger sets of RGN specificity profiles.

Despite these challenges in comprehensively predicting RGN specificities, it was possible to identify bona fide off-targets of RGNs by examining a subset of genomic sites that differed from the on-target site by one to five mismatches. Notably, under conditions of these experiments, the frequencies of RGN-induced mutations at many of these off-target sites were similar to (or higher than) those observed at the intended on-target site, enabling the detection of mutations at these sites using the T7EI assay (which, as performed in our laboratory, has a reliable detection limit of ~2 to 5% mutation frequency). Because these mutation rates were very high, it was possible to avoid using deep sequencing methods previously required to detect much lower frequency ZFN- and TALEN-induced off-target alterations (Pattanayak et al., Nat Methods 8, 765-770 (2011); Perez et al., Nat Biotechnol 26, 808-816 (2008); Gabriel et al., Nat Biotechnol 29, 816-823 (2011); Hockemeyer et al., Nat Biotechnol 29, 731-734 (2011)). Analysis of RGN off-target mutagenesis in human cells also confirmed the difficulties of predicting RGN specificities—not all single and double mismatched off-target sites show evidence of mutation whereas some sites with as many as five mismatches can also show alterations. Furthermore, the bona fide off-target sites identified do not exhibit any obvious bias toward transition or transversion differences relative to the intended target sequence.

Although off-target sites were seen for a number of RGNs, identification of these sites was neither comprehensive nor genome-wide in scale. For the six RGNs studied, only a very small subset of the much larger total number of potential off-target sequences in the human genome (sites that differ by three to six nucleotides from the intended target site) was examined. Although examining such large numbers of loci for off-target mutations by T7EI assay is neither a practical nor a cost-effective strategy, the use of high-throughput sequencing in future studies might enable the interrogation of larger numbers of candidate off-target sites and provide a more sensitive method for detecting bona fide off-target mutations. For example, such an approach might enable the unveiling of additional off-target sites for the two RGNs for which we failed to uncover any off-target mutations. In addition, an improved understanding both of RGN specificities and of any epigenomic factors (e.g., DNA methylation and chromatin status) that may influence RGN activities in cells might also reduce the number of potential sites that need to be examined and thereby make genome-wide assessments of RGN off-targets more practical and affordable.

As described herein, a number of strategies can be used to minimize the frequencies of genomic off-target mutations. For example, the specific choice of RGN target site can be optimized; given that off-target sites that differ at up to five positions from the intended target site can be efficiently mutated by RGNs, choosing target sites with minimal numbers of off-target sites as judged by mismatch counting seems unlikely to be effective; thousands of potential off-target sites that differ by four or five positions within the 20 bp RNA:DNA complementarity region will typically exist for any given RGN targeted to a sequence in the human genome. It is also possible that the nucleotide content of the gRNA complementarity region might influence the range of potential off-target effects. For example, high GC-content has been shown to stabilize RNA:DNA hybrids (Sugimoto et al., Biochemistry 34, 11211-11216 (1995)) and therefore might also be expected to make gRNA/genomic DNA hybridization more stable and more tolerant to mismatches. Additional experiments with larger numbers of gRNAs will be needed to assess if and how these two parameters (numbers of mismatched sites in the genome and stability of the RNA:DNA hybrid) influence the genome-wide specificities of RGNs. However, it is important to note that even if such predictive parameters can be defined, the effect of implementing such guidelines would be to further restrict the targeting range of RGNs.

One potential general strategy for reducing RGN-induced off-target effects might be to reduce the concentrations of gRNA and Cas9 nuclease expressed in the cell. This idea was tested using the RGNs for VEGFA target sites 2 and 3 in U2OS.EGFP cells; transfecting less gRNA- and Cas9-expressing plasmid decreased the mutation rate at the on-target site but did not appreciably change the relative rates of off-target mutations. Consistent with this, high-level off-target mutagenesis rates were also observed in two other human cell types (HEK293 and K562 cells) even though the absolute rates of on-target mutagenesis are lower than in U2OS.EGFP cells. Thus, reducing expression levels of gRNA and Cas9 in cells is not likely to provide a solution for reducing off-target effects. Furthermore, these results also suggest that the high rates of off-target mutagenesis observed in human cells are not caused by overexpression of gRNA and/or Cas9.

The finding that significant off-target mutagenesis can be induced by RGNs in three different human cell types has important implications for broader use of this genome-editing platform. For research applications, the potentially confounding effects of high frequency off-target mutations will need to be considered, particularly for experiments involving either cultured cells or organisms with slow generation times for which the outcrossing of undesired alterations would be challenging. One way to control for such effects might be to utilize multiple RGNs targeted to different DNA sequences to induce the same genomic alteration because off-target effects are not random but instead related to the targeted site. However, for therapeutic applications, these findings clearly indicate that the specificities of RGNs will need to be carefully defined and/or improved if these nucleases are to be used safely in the longer term for treatment of human diseases.

Methods for Improving Specificity

As shown herein, CRISPR-Cas RNA-guided nucleases based on the *S. pyogenes* Cas9 protein can have significant off-target mutagenic effects that are comparable to or higher than the intended on-target activity (Example 1). Such off-target effects can be problematic for research and in particular for potential therapeutic applications. Therefore, methods for improving the specificity of CRISPR-Cas RNA guided nucleases (RGNs) are needed.

As described in Example 1, Cas9 RGNs can induce high-frequency indel mutations at off-target sites in human cells (see also Cradick et al., 2013; Fu et al., 2013; Hsu et al., 2013; Pattanayak et al., 2013). These undesired alterations can occur at genomic sequences that differ by as many as five mismatches from the intended on-target site (see Example 1). In addition, although mismatches at the 5' end of the gRNA complementarity region are generally better tolerated than those at the 3' end, these associations are not absolute and show site-to-site-dependence (see Example 1 and Fu et al., 2013; Hsu et al., 2013; Pattanayak et al., 2013). As a result, computational methods that rely on the number and/or positions of mismatches currently have limited predictive value for identifying bona fide off-target sites. Therefore, methods for reducing the frequencies of off-target mutations remain an important priority if RNA-guided nucleases are to be used for research and therapeutic applications.

Strategy #1: Synthetic Alternatives to Standard gRNAs to Improve Specificity

Guide RNAs generally speaking come in two different systems: System 1, which uses separate crRNA and tracrRNAs that function together to guide cleavage by Cas9, and System 2, which uses a chimeric crRNA-tracrRNA hybrid that combines the two separate guide RNAs in a single system (referred to as a single guide RNA or sgRNA, see also Jinek et al., Science 2012; 337:816-821). The tracrRNA can be variably truncated and a range of lengths has been shown to function in both the separate system (system 1) and the chimeric gRNA system (system 2). For example, in some embodiments, tracrRNA may be truncated from its 3' end by at least 1, 2, 3, 4, 5, 6, 7, 8, 9, 10, 15, 20, 25, 30, 35 or 40 nts. In some embodiments, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. See, e.g., Jinek et al., Science 2012; 337:816-821; Mali et al., Science. 2013 Feb. 15; 339(6121):823-6; Cong et al., Science. 2013 Feb. 15; 339 (6121):819-23; and Hwang and Fu et al., Nat Biotechnol. 2013 March; 31(3):227-9; Jinek et al., Elife 2, e00471 (2013)). For System 2, generally the longer length chimeric gRNAs have shown greater on-target activity but the relative specificities of the various length gRNAs currently remain undefined and therefore it may be desirable in certain instances to use shorter gRNAs. In some embodiments, the gRNAs are complementary to a region that is within about 100-800 bp upstream of the transcription start site, e.g., is within about 500 bp upstream of the transcription start site, includes the transcription start site, or within about 100-800 bp, e.g., within about 500 bp, downstream of the transcription start site. In some embodiments, vectors (e.g., plasmids) encoding more than one gRNA are used, e.g., plasmids encoding, 2, 3, 4, 5, or more gRNAs directed to different sites in the same region of the target gene.

Described herein are guide RNAs, e.g., single gRNAs or crRNA and tracrRNA, that include one or more modified (e.g., locked) nucleotides or deoxyribonucleotides.

Strategy 1A: Modified Nucleic Acid Molecules

Modified RNA oligonucleotides such as locked nucleic acids (LNAs) have been demonstrated to increase the specificity of RNA-DNA hybridization by locking the modified oligonucleotides in a more favorable (stable) conformation.

For example, 2'-O-methyl RNA is a modified base where there is an additional covalent linkage between the 2' oxygen and 4' carbon which when incorporated into oligonucleotides can improve overall thermal stability and selectivity (formula I).

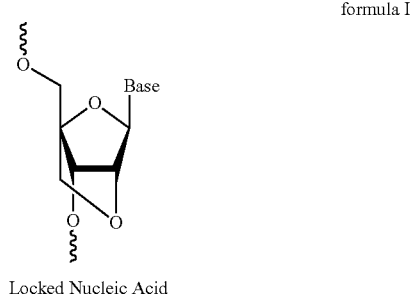

formula I

Locked Nucleic Acid

Guide RNAs as described herein may be synthetic guide RNA molecules wherein one, some or all of the nucleotides 5' region of the guide RNA complementary to the target sequence are modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In another embodiment, one, some or all of the nucleotides of the gRNA sequence may be modified, e.g., locked (2'-O-4'-C methylene bridge), 5'-methylcytidine, 2'-O-methyl-pseudouridine, or in which the ribose phosphate backbone has been replaced by a polyamide chain (peptide nucleic acid), e.g., a synthetic ribonucleic acid.

In a cellular context, complexes of Cas9 with these synthetic gRNAs could be used to improve the genome-wide specificity of the CRISPR/Cas9 nuclease system. Exemplary modified or synthetic gRNAs may comprise, or consist of, the following sequences:

($X_{17-20}$) GUUUUAGAGCUAUGCUGUUUUG($X_N$) (SEQ ID NO:4);

($X_{17-20}$)GUUUUAGAGCUA (SEQ ID NO:5);

($X_{17-20}$)GUUUUAGAGCUAUGCUGUUUUG (SEQ ID NO:6);

($X_{17-20}$)GUUUUAGAGCUAUGCU (SEQ ID NO:7);

($X_{17-20}$)GUUUUAGAGCUAGAAAUAG-CAAGUUAAAAUAAGGCUAGUCCG($X_N$) (SEQ ID NO:8);

($X_{17-20}$)GUUUUAGAGCUAUGCUGAAAAGCAUAG-CAAGUUAAAAUAAGGCU AGUCCGUUAUC($X_N$) (SEQ ID NO:9);

($X_{17-20}$)GUUUUAGAGCUAUGCUGUUUUG-GAAACAAAACAGCAUAGCAAGU UAAAAUAAGGCUAGUCCGUUAUC($X_N$) (SEQ ID NO:10);

($X_{17-20}$)GUUUUAGAGCUAGAAAUAG-CAAGUUAAAAUAAGGCUAGUCCGUU AUCAAC-UUGAAAAAGUGGCACCGAGUCGGUGC($X_N$) (SEQ ID NO:11), ($X_{17-20}$)GUUUAAGAGCUAGAAAUAG-CAAGUUUAAAUAAGGCUAGUCCGUU AUCAAC-UUGAAAAAGUGGCACCGAGUCGGUGC(SEQ ID NO:12);

($X_{17-20}$)GUUUUAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:13); or ($X_{17-20}$)GUUUAAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:14), wherein $X_{17-20}$ is a sequence complementary to 17-20 nts of a target sequence, preferably a target sequence immediately 5' of a protospacer adjacent motif (PAM), e.g., NGG, NAG, or NNGG, and further wherein one or more of the nucleotides are locked, e.g., one or more of the nucleotides within the sequence $X_{17-20}$, one or more of the nucleotides within the sequence $X_N$, or one or more of the nucleotides within any sequence of the gRNA. In some embodiments, $X_{17-20}$ is $X_{17-18}$, e.g., is 17-18 nucleotides long; in some embodiments, the target complementarity can be longer, e.g., 17-20, 21, 22, 23, 24, 25, or more nucleotides long. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

In addition, in a system that uses separate crRNA and tracrRNA, one or both can be synthetic and include one or more locked nucleotides, as dual gRNAs (e.g., the crRNA and tracrRNA found in naturally occurring systems) can also be modified. In this case, a single tracrRNA would be used in conjunction with multiple different crRNAs expressed using the present system, e.g., the following:
($X_{17-20}$)GUUUUAGAGCUA (SEQ ID NO:5);
($X_{17-20}$)GUUUUAGAGCUAUGCUGUUUUG (SEQ ID NO:6); or
($X_{17-20}$)GUUUUAGAGCUAUGCU (SEQ ID NO:7); and a tracrRNA sequence. In this case, the crRNA is used as the guide RNA in the methods and molecules described herein, and the tracrRNA can be expressed from the same or a different DNA molecule. In some embodiments, the methods include contacting the cell with a tracrRNA comprising or consisting of the sequence GGAACCAUUCAAAACAG-CAUAGCAAGUUAAAAUAAGGCUAGUCCGUUA UCAACUUGAAAAAGUGGCACCGAGUCGGUGC (SEQ ID NO:15) or an active portion thereof (an active portion is one that retains the ability to form complexes with Cas9 or dCas9). In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. Exemplary tracrRNA sequences in addition to SEQ ID NO:8 include the following:
UAGCAAGUUAAAAUAAGGCUAGUCCGUUAU-CAACUUGAAAAAGUGGCA CCGAGUCGGUGC (SEQ ID NO:16) or an active portion thereof; or
AGCAUAGCAAGUUAAAAUAAGGCUAGUC-CGUUAUCAACUUGAAAAAGU GGCACCGAGUCG-GUGC (SEQ ID NO:17) or an active portion thereof.

In some embodiments wherein ($X_{17-20}$)GUUUUA-GAGCUAUGCUGUUUUG (SEQ ID NO:6) is used as a crRNA, the following tracrRNA is used:
GGAACCAUUCAAAACAGCAUAG-CAAGUUAAAAUAAGGCUAGUCCGUUA UCAAC-UUGAAAAAGUGGCACCGAGUCGGUGC (SEQ ID NO:15) or an active portion thereof. In some embodiments wherein ($X_{17-20}$)GUUUUAGAGCUA (SEQ ID NO:5) is used as a crRNA, the following tracrRNA is used:
UAGCAAGUUAAAAUAAGGCUAGUCCGUUAU-CAACUUGAAAAAGUGGCA CCGAGUCGGUGC (SEQ ID NO:16) or an active portion thereof. In some embodiments wherein ($X_{17-20}$)GUUUUAGAGCUAUGCU (SEQ ID NO:7) is used as a crRNA, the following tracrRNA is used:
AGCAUAGCAAGUUAAAAUAAGGCUAGUC-CGUUAUCAACUUGAAAAAGU GGCACCGAGUCG-GUGC (SEQ ID NO:17) or an active portion thereof.

In a system that uses separate crRNA and tracrRNA, one or both can be synthetic and include one or more modified (e.g., locked) nucleotides.

In some embodiments, the single guide RNAs or crRNAs or tracrRNAs includes one or more Adenine (A) or Uracil (U) nucleotides on the 3' end.

The methods described can include contacting the cell with a locked gRNA as described herein, and contacting the cell with or expressing in the cell a nuclease that can be guided by the locked gRNAs, e.g., a Cas9 nuclease, e.g., as described in Mali et al., a Cas9 nickase as described in Jinek et al., 2012; or a dCas9-heterofunctional domain fusion (dCas9-HFD) as described in U.S. Provisional Patent Applications U.S. Ser. No. 61/799,647, Filed on Mar. 15, 2013, U.S. Ser. No. 61/838,148, filed on Jun. 21, 2013, and PCT International Application No. PCT/US14/27335, all of which are incorporated herein by reference in its entirety.

Strategy 1B: DNA-Based Guide Molecules

Existing Cas9-based RGNs use gRNA-DNA heteroduplex formation to guide targeting to genomic sites of interest. However, RNA-DNA heteroduplexes can form a more promiscuous range of structures than their DNA-DNA counterparts. In effect, DNA-DNA duplexes are more sensitive to mismatches, suggesting that a DNA-guided nuclease may not bind as readily to off-target sequences, making them comparatively more specific than RNA-guided nucleases. To this end, we propose an engineered Cas9-based RGN wherein a short DNA oligonucleotide replaces all or part of the complementarity region of a gRNA (for example, see FIG. 4). This DNA-based molecule could replace either all or part of the gRNA in a single gRNA system or alternatively might replace all of part of the crRNA in a dual crRNA/tracrRNA system. Such a system that incorporates DNA into the complementarity region should more reliably target the intended genomic DNA sequences due to the general intolerance of DNA-DNA duplexes to mismatching compared to RNA-DNA duplexes. Methods for making such duplexes are known in the art, See, e.g., Barker et al., BMC Genomics. 2005 Apr. 22; 6:57; and Sugimoto et al., Biochemistry. 2000 Sep. 19; 39(37):11270-81. Thus, in some embodiments, described herein are hybrid guide DNA/RNAs consisting of the sequence:
($X_{17-20}$) GUUUUAGAGCUAUGCUGUUUUG($X_N$) (SEQ ID NO:4);
($X_{17-20}$)GUUUUAGAGCUA (SEQ ID NO:5);
($X_{17-20}$) GUUUUAGAGCUAUGCUGUUUUG (SEQ ID NO:6);
($X_{17-20}$)GUUUUAGAGCUAUGCU (SEQ ID NO:7);
($X_{17-20}$)GUUUUAGAGCUAGAAAUAG-CAAGUUAAAAUAAGGCUAGUCCG($X_N$(SEQ ID NO:8);
($X_{17-20}$)GUUUUAGAGCUAUGCUGAAAAGCAUAG-CAAGUUAAAAUAAGGCU AGUCCGUUAUC($X_N$) (SEQ ID NO:9);

$(X_{17-20})$GUUUUAGAGCUAUGCUGUUUUG-GAAACAAAACAGCAUAGCAAGU UAAAAUAAGGCUAGUCCGUUAUC$(X_N)$ (SEQ ID NO:10);
$(X_{17-20})$GUUUUAGAGCUAGAAAUAG-CAAGUUUAAAAUAAGGCUAGUCCGUU AUCAAC-UUGAAAAAGUGGCACCGAGUCGGUGC$(X_N)$ (SEQ ID NO:11),
$(X_{17-20})$GUUUAAGAGCUAGAAAUAG-CAAGUUUAAAAUAAGGCUAGUCCGUU AUCAAC-UUGAAAAAGUGGCACCGAGUCGGUGC(SEQ ID NO:12);
$(X_{17-20})$GUUUUAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:13); or
$(X_{17-20})$GUUUAAGAGCUAUGCUGGAAACAG-CAUAGCAAGUUUAAAUAAGG CUAGUCCGUUAU-CAACUUGAAAAAGUGGCACCGAGUCGGUGC (SEQ ID NO:14), wherein the $X_{17-20}$ is a sequence complementary to 17-20 nts of a target sequence, preferably a target sequence immediately 5' of a protospacer adjacent motif (PAM), e.g., NGG, NAG, or NNGG, wherein the $X_{17-20}$ is at least partially or wholly DNA, e.g., one or more of the nucleotides are deoxyribonucleotides (e.g., is all or partially DNA, e.g. DNA/RNA hybrids), e.g., one or more of the nucleotides within the sequence $X_{17-20}$, one or more of the nucleotides within the sequence $X_N$, or one or more of the nucleotides within any sequence of the gRNA is a deoxyribonucleotide. In some embodiments, $X_{17-20}$ is $X_{17-18}$, e.g., is 17-18 nucleotides long. $X_N$ is any sequence, wherein N (in the RNA) can be 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

In addition, in a system that uses separate crRNA and tracrRNA, one or both can be synthetic and include one or more deoxyribonucleotides, as dual gRNAs (e.g., the crRNA and tracrRNA found in naturally occurring systems) can also be hybrids. In this case, a single tracrRNA would be used in conjunction with multiple different crRNAs expressed using the present system, e.g., the following:
$(X_{17-20})$GUUUUAGAGCUA (SEQ ID NO:5);
$(X_{17-20})$GUUUUAGAGCUAUGCUGUUUUG (SEQ ID NO:6); or
$(X_{17-20})$GUUUUAGAGCUAUGCU (SEQ ID NO:7); and a tracrRNA sequence. In this case, the crRNA is used as the guide RNA in the methods and molecules described herein, and the tracrRNA can be expressed from the same or a different DNA molecule. In some embodiments, the methods include contacting the cell with a tracrRNA comprising or consisting of the sequence GGAACCAUUCAAAACAG-CAUAGCAAGUUAAAAUAAGGCUAGUCCGUUA UCAACUUGAAAAAGUGGCACCGAGUCGGUGC (SEQ ID NO:15) or an active portion thereof (an active portion is one that retains the ability to form complexes with Cas9 or dCas9). In some embodiments, the tracrRNA molecule may be truncated from its 3' end by at least 1, 2, 3, 4, 5, 6, 7, 8, 9, 10, 15, 20, 25, 30, 35 or 40 nts. In another embodiment, the tracrRNA molecule may be truncated from its 5' end by at least 1, 2, 3, 4, 5, 6, 7, 8, 9, 10, 15, 20, 25, 30, 35 or 40 nts. Alternatively, the tracrRNA molecule may be truncated from both the 5' and 3' end, e.g., by at least 1, 2, 3, 4, 5, 6, 7, 8, 9, 10, 15 or 20 nts on the 5' end and at least 1, 2, 3, 4, 5, 6, 7, 8, 9, 10, 15, 20, 25, 30, 35 or 40 nts on the 3' end. Exemplary tracrRNA sequences in addition to SEQ ID NO:8 include the following:
UAGCAAGUUAAAAUAAGGCUAGUCCGUUAU-CAACUUGAAAAAGUGGCA CCGAGUCGGUGC (SEQ ID NO:16) or an active portion thereof; or
AGCAUAGCAAGUUAAAAUAAGGCUAGUC-CGUUAUCAACUUGAAAAAGU GGCACCGAGUCG-GUGC (SEQ ID NO:17) or an active portion thereof.

In some embodiments wherein $(X_{17-20})$GUUUUA-GAGCUAUGCUGUUUUG (SEQ ID NO:6) is used as a crRNA, the following tracrRNA is used:
GGAACCAUUCAAAACAGCAUAG-CAAGUUAAAAUAAGGCUAGUCCGUUA UCAAC-UUGAAAAAGUGGCACCGAGUCGGUGC (SEQ ID NO:15) or an active portion thereof. In some embodiments wherein $(X_{17-20})$GUUUUAGAGCUA (SEQ ID NO:5) is used as a crRNA, the following tracrRNA is used:
UAGCAAGUUAAAAUAAGGCUAGUCCGUUAU-CAACUUGAAAAAGUGGCA CCGAGUCGGUGC (SEQ ID NO:16) or an active portion thereof. In some embodiments wherein $(X_{17-20})$GUUUUAGAGCUAUGCU (SEQ ID NO:7) is used as a crRNA, the following tracrRNA is used:
AGCAUAGCAAGUUAAAAUAAGGCUAGUC-CGUUAUCAACUUGAAAAAGU GGCACCGAGUCG-GUGC (SEQ ID NO:17) or an active portion thereof.

In a system that uses separate crRNA and tracrRNA, one or both can be synthetic and include one or more deoxyribonucleotides.

In some embodiments, the guide RNA includes one or more Adenine (A) or Uracil (U) nucleotides on the 3' end. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription.

Strategy #2: Use of Pairs of Cas9 RNA-Guided Nickases (RGNickases) to Induce Paired Nicks on Opposing Strands of DNA Mutations have been described that inactivate one of the two endonuclease activities found in the *S. pyogenes* Cas9 nuclease (Jinek et al., Science 2012; Nishimasu al., Cell 156, 935-949 (2014)). Introduction of one of these mutations converts an RGN into an RGNickase that cuts only one of the two DNA strands in a predictable fashion (Jinek et al., Science 2012). Thus by using pairs of appropriately placed RGNickases (two gRNAs and one Cas9 nickase), one can introduce targeted paired nicks on opposing strands of DNA (FIG. 5). Depending on the positioning of these RGNickases and which strand is cleaved by each of them, one can imagine that these nicks might be positioned on opposing strands in one orientation or another (FIG. 5). Because two nickases result in a doubling in the target length this can lead to greater specificity.

In some embodiments, the present system utilizes the Cas9 protein from *S. pyogenes*, either as encoded in bacteria or codon-optimized for expression in mammalian cells, containing mutations the nuclease portion of the protein partially catalytically inactive. The wild type sequence of the *S. pyogenes* Cas9 that can be used in the methods and compositions described herein is set forth below.

Thus described herein are methods that include expressing in a cell, or contacting a cell with, two guide RNAs and one Cas9-nickase (e.g., a Cas9 with a mutation at any of D10, E762, H983, D986, H840, or N863, that renders only one of the nuclease portions of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g E762Q, H983N/H983Y, D986N, N863D/N863S/N863H D10A/D10N, H840A/H840N/H840Y), wherein each of the two guide RNAs include sequences that are complementary to either strand of the target sequence, such that using both guide RNAs results in targeting both strands, and the Cas9-nickase cuts each strand singly on opposing strands of DNA. The RGNickase, like RGNs consisting of wildtype Cas9 is expected to cut the DNA target site approximately 3 bp upstream of the PAM, with the D10A Cas9 cleaving the complementary DNA strand and the H840A Cas9 cleaving the non-complementary strand. The two gRNA target sites may be overlapping or some distance away from each other, e.g., up to about 200 nts apart, e.g., less than 100, 50, 25, 10, 5, 4, or 2 nts apart.

Strategy #3: RNA-Binding Protein-FokI/HFD Fusions

Another method to improve the specificity of Cas9 is to use dCas9 together with a modified gRNA bearing extra RNA sequence on either the 5' or 3' end of the gRNA (or on the ends of the crRNA and/or tracrRNA if using a dual gRNA system) that is bound by an RNA-binding protein that is in turn fused to a heterologous functional domain (HFD), e.g., the FokI nuclease domain. In this configuration (FIG. 6), two dCas9 molecules would be targeted to adjacent DNA sequences by appropriate gRNAs and the "extra" RNA sequence on the two gRNA would interact with an appropriate RNA-binding protein-HFD (e.g., FokI nuclease domain) fusion. In the appropriate configuration, the HFD/FokI nuclease domains would dimerize, thereby resulting in introduction of a targeted double-stranded break in the DNA sequence between the two dCas9 binding sites. In addition to the example described herein of FokI-Csy4, VP64-Csy4, TET1-Csy4, and so on could be used. As with the strategy described above, this would result in the need to use two modified gRNAs to form the complex having dCas9 and the required RNA-binding protein-FokI domain fusion molecules, thereby requiring greater specificity than that of a single gRNA-Cas9 complex.

RNA-binding protein/RNA target sequences that could be used would include but are not limited to the lambda N, MS2 or Csy4 proteins. The wild type and high-affinity sequences for MS2 are AAACAUGAGGAUUACCCAUGUCG (SEQ ID NO:19) and AAACAUGAGGAUCACCCAUGUCG (SEQ ID NO:20), respectively (see Keryer-Bibens et al., supra, FIG. 2); the nutL and nutR BoxB sequences to which lambda N binds are GCCCUGAAGAAGGGC (SEQ ID NO:21) and GCCCUGAAAAAGGGC (SEQ ID NO:22), respectively. The sequences to which Csy4 binds are GUUCACUGCCGUAUAGGCAG (SEQ ID NO:23) or GUUCACUGCCGUAUAGGCAGCUAAGAAA (SEQ ID NO:24). The binding sites can be attached to 3' end of a gRNA sequence and gRNAs harboring this additional Csy4 binding site can still direct Cas9 to cleave specific sequences in human cells and thus remain functional in the cell (Example 2 and FIG. 7).

Thus described herein are three-part fusion guide nucleic acids comprising: (1) a first sequence of 17-20 nts that is complementary to the complementary strand of 17-20 consecutive nucleotides of a target sequence with an adjacent PAM sequence; (2) a second sequence comprising all or part of a Cas9 guide RNA, e.g., all or part of GUUUUAGAGC-UAGAAAUAGCAAGUUAAAAUAAGGCUAGUC-CGUUAUCA ACUUGAAAAAGUGGCACCGAGTCG-GUGCUUUU (SEQ ID NO:15) or an active portion thereof, UAGCAAGUUAAAAUAAGGCUAGUCCGUUAU-CAACUUGAAAAAGUGGCA CCGAGUCGGUGC (SEQ ID NO:16) or an active portion thereof; or AGCAUAG-CAAGUUAAAAUAAGGCUAGUCCGUUAUCAAC-UUGAAAAAGU GGCACCGAGUCGGUGC (SEQ ID NO:17) or an active portion thereof; and (3) a third sequence that forms a stem-loop structure recognized by an RNA binding protein, e.g., MS2, Csy4, or lambda N. These sequences can be arranged in any order so long as all of the parts retain their function, e.g., (1)-(2)-(3), or (3)-(1)-(2), or (3)-(2)-(1), or (1)-(3)-(2), or (2)-(1)-(3), or (2)-(3)-(1).

In some embodiments wherein $(X_{17-20})$GUUUUA-GAGCUAUGCUGUUUUG (SEQ ID NO:6) is used as a crRNA, the following tracrRNA is used: GGAACCAUUCAAAACAGCAUAG-CAAGUUAAAAUAAGGCUAGUCCGUUA UCAAC-UUGAAAAAGUGGCACCGAGUCGGUGC (SEQ ID NO:15) or an active portion thereof. In some embodiments wherein $(X_{17-20})$GUUUUAGAGCUA (SEQ ID NO:5) is used as a crRNA, the following tracrRNA is used: UAGCAAGUUAAAAUAAGGCUAGUCCGUUAU-CAACUUGAAAAAGUGGCA CCGAGUCGGUGC (SEQ ID NO:16) or an active portion thereof. In some embodiments wherein $(X_{17-20})$GUUUUAGAGCUAUGCU (SEQ ID NO:7) is used as a crRNA, the following tracrRNA is used: AGCAUAGCAAGUUAAAAUAAGGCUAGUC-CGUUAUCAACUUGAAAAAGU GGCACCGAGUCG-GUGC (SEQ ID NO:17) or an active portion thereof.

In some embodiments, there are additional nucleotides, e.g., up to 20 additional nucleotides, that act as a flexible linker between Csy4 and the gRNA; these nucleotides should not add any secondary or tertiary structure to the gRNA. For example the sequence 'GTTC' has been shown to be unstructured and could be construed as 'linker' sequence.

In some embodiments, the wild-type Csy4 binding sequence is used, which is: GUUCACUGCCGUAUAG-GCAGCUAAGAAA (SEQ ID NO:24). In some embodiments, a truncated Csy4 binding sequence is used, which upon processing by Csy4 produces gRNAs of higher activity. This sequence is GUUCACUGCCGUAUAGGCAG (SEQ ID NO:23).

Also provided are fusion proteins comprising an RNA binding protein, e.g., MS2, Csy4, or lambda N, linked to a catalytic domain of a HFD, e.g., a FokI nuclease as described above, optionally with an intervening linker of 2-30, e.g., 5-20 nts, as well as nucleic acids encoding the same.

MS2/Lambda N/Csy4

Exemplary sequences for the MS2, lambda N, and Csy4 proteins are given below; the MS2 functions as a dimer, therefore the MS2 protein can include a fused single chain dimer sequence.

1. Exemplary Sequences for Fusions of Single MS2 Coat Protein (wt, N55K or deltaFG) to the N-Terminus or C-Terminus of FokI.

MS2 coat protein amino acid sequence:

(SEQ ID NO: 25)
MASNFTQFVLVDNGGTGDVTVAPSNFANGVAEWISSNSRSQAYKVTCSVR

QSSAQNRKYTIKVEVPKVATQTVGGVELPVAAWRSYLNMELTIPIFATNS

DCELIVKAMQGLLKDGNPIPSAIAANSGIY

MS2 N55K:

(SEQ ID NO: 26)
MASNFTQFVLVDNGGTGDVTVAPSNFANGVAEWISSNSRSQAYKVTCSVR

QSSAQKRKYTIKVEVPKVATQTVGGVELPVAAWRSYLNMELTIPIFATNS

DCELIVKAMQGLLKDGNPIPSAIAANSGIY

MS2deltaFG:

(SEQ ID NO: 27)
MASNFTQFVLVDNGGTGDVTVAPSNFANGIAEWISSNSRSQAYKVTCSVR

QSSAQNRKYTIKVEVPKGAWRSYLNMELTIPIFATNSDCELIVKAMQGLL

KDGNPIPSAIAANSGIY

2. Exemplary Sequences for Fusions of Fused Dimeric MS2 Coat Protein (wt, N55K or deltaFG) to the N-Terminus or C-Terminus of FokI.

Dimeric MS2 coat protein:

(SEQ ID NO: 28)
MASNFTQFVLVDNGGTGDVTVAPSNFANGVAEWISSNSRSQAYKVTCSVR

QSSAQNRKYTIKVEVPKVATQTVGGVELPVAAWRSYLNMELTIPIFATNS

DCELIVKAMQGLLKDGNPIPSAIAANSGLYGAMASNFTQFVLVDNGGTGD

VTVAPSNFANGVAEWISSNSRSQAYKVTCSVRQSSAQNRKYTIKVEVPKV

ATQTVGGVELPVAAWRSYLNMELTIPIFATNSDCELIVKAMQGLLKDGNP

IPSAIAANSLIN

Dimeric MS2 N55K:

(SEQ ID NO: 29)
MASNFTQFVLVDNGGTGDVTVAPSNFANGVAEWISSNSRSQAYKVTCSVR

QSSAQKRKYTIKVEVPKVATQTVGGVELPVAAWRSYLNMELTIPIFATNS

DCELIVKAMQGLLKDGNPIPSAIAANSGLYGAMASNFTQFVLVDNGGTGD

VTVAPSNFANGVAEWISSNSRSQAYKVTCSVRQSSAQKRKYTIKVEVPKV

ATQTVGGVELPVAAWRSYLNMELTIPIFATNSDCELIVKAMQGLLKDGNP

IPSAIAANSLIN

Dimeric MS2deltaFG:

(SEQ ID NO: 30)
MASNFTQFVLVDNGGTGDVTVAPSNFANGVAEWISSNSRSQAYKVTCSVR

QSSAQKRKYTIKVEVPKGAWRSYLNMELTIPIFATNSDCELIVKAMQGLL

KDGNPIPSAIAANSGLYGAMASNFTQFVLVDNGGTGDVTVAPSNFANGVA

EWISSNSRSQAYKVTCSVRQSSAQKRKYTIKVEVPKGAWRSYLNMELTIP

IFATNSDCELIVKAMQGLLKDGNPIPSAIAANSLIN

3. Exemplary Sequences for Fusions of Lambda N to N-Terminus or C-Terminus of FokI.

Lambda N amino acid sequence:

(SEQ ID NO: 31)
MDAQTRRRERRAEKQAQWKAAN or (SEQ ID NO: 32)
MDAQTRRRERRAEKQAQWKAANPLLVGVSAKPVNRPILSLNRKPKSRVES

ALNPIDLTVLAEYHKQIESNLQRIERKNQRTWYSKPGERGITCSGRQKIK

GKSIPLI

4. Exemplary Sequence for Fusions of Csy4 to N-Terminus or C-Terminus of dCas9

Exemplary sequences for Cys4 are given in Haurwitz et al. 329(5997):1355-8 (2010), e.g., the inactivated form; for example see the Csy4 homologues from *Pseudomonas aeruginosa* UCBPP-PA14 (Pal4), *Yersinia pestis* AAM85295 (Yp), *Escherichia coli* UTI89 (Ec89), *Dichelobacter nodosus* VCS1703A (Dn), *Acinetobacter baumannii* AB0057 (Ab), *Moritella* sp. PE36 (MP1, MP01), *Shewanella* sp. W3-18-1 (SW), *Pasteurella multocida* subsp. *multocida* Pm70 (Pm), *Pectobacterium wasabiae* (Pw), and *Dickeya dadantii* Ech703 (Dd) that are set forth in FIG. S6 of Haurwitz et al., Science 329(5997): 1355-1358 (2010). In preferred embodiments, the Csy4 is from *Pseudomonas aeruginosa*.

Figure 1:
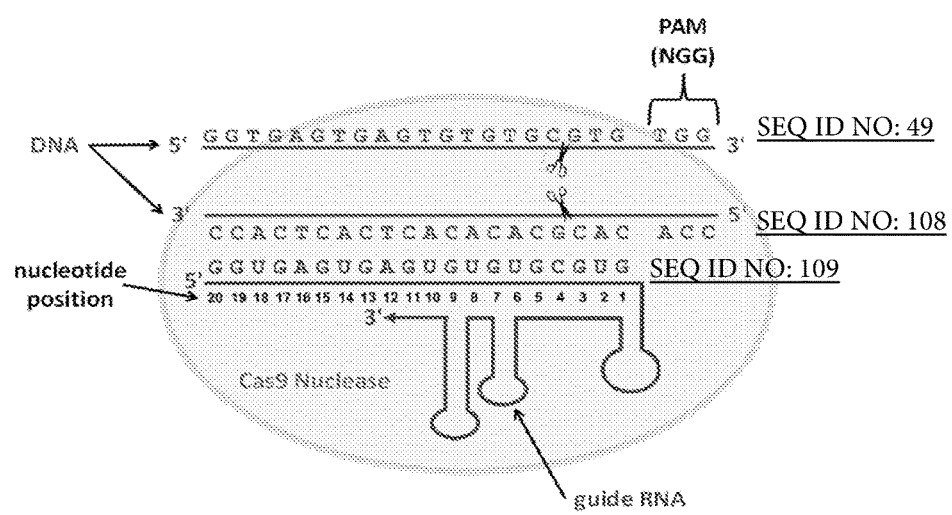
FIG. 1: Schematic illustrating a gRNA/Cas9 nuclease complex bound to its target DNA site. Scissors indicate approximate cleavage points of the Cas9 nuclease on the genomic DNA target site. Note the numbering of nucleotides on the guide RNA proceeds in an inverse fashion from 5' to 3'.

Methods of using the fusions include contacting a cell with or expressing in a cell a pair of three-part fusion guide nucleic acids that include sequences complementary to a single region of a target DNA, a RNA-binding protein linked to a catalytic domain of a FokI nuclease, and a Cas9 protein (e.g., the inactive dCas9 protein from *S. pyogenes*, either as encoded in bacteria or codon-optimized for expression in mammalian cells, containing mutations at D10, E762, H983, D986, H840, or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)) or they could be other residues, e.g., glutamine, asparagine, tyrosine, serine, or aspartate, e.g., E762Q, H983N, H983Y, D986N, N863D, N863S, or N863H (FIG. 1C).). The two gRNA target sites may be overlapping or some distance away from each other, e.g., up to about 200 nts apart, e.g., less than 100, 50, 25, 10, 5, 4, or 2 nts apart.

FokI

FokI is a type IIs restriction endonuclease that includes a DNA recognition domain and a catalytic (endonuclease) domain. The fusion proteins described herein can include all of FokI or just the catalytic endonuclease domain, i.e., amino acids 388-583 or 408-583 of GenBank Acc. No. AAA24927.1, e.g., as described in Li et al., Nucleic Acids Res. 39(1): 359-372 (2011); Cathomen and Joung, Mol. Ther. 16: 1200-1207 (2008), or a mutated form of FokI as described in Miller et al. Nat Biotechnol 25: 778-785 (2007); Szczepek et al., Nat Biotechnol 25: 786-793 (2007); or Bitinaite et al., Proc. Natl. Acad. Sci. USA. 95:10570-10575 (1998).

An exemplary amino acid sequence of FokI is as follows:

(SEQ ID NO: 33)

| | 10 | 20 | 30 | 40 |
|---|---|---|---|---|
| | MFLSMVSKIR | TFGWVQNPGK | FENLKRVVQV | FDRNSKVHNE |
| | 50 | 60 | 70 | 80 |
| | VKNIKIPTLV | KESKIQKELV | AIMNQHDLIY | TYKELVGTGT |
| | 90 | 100 | 110 | 120 |
| | SIRSEAPCDA | IIQATIADQG | NKKGYIDNWS | SDGFLRWAHA |
| | 130 | 140 | 150 | 160 |
| | LGFIEYINKS | DSFVITDVGL | AYSKSADGSA | IEKEILIEAI |

```
        170        180        190        200
SSYPPAIRIL TLLEDGQHLT KFDLGKNLGF SGESGFTSLP 210        220        230        240
EGILLDTLAN AMPKDKGEIR NNWEGSSDKY ARMIGGWLDK 250        260        270        280
LGLVKQGKKE FIIPTLGKPD NKEFISHAFK ITGEGLKVLR 290        300        310        320
RAKGSTKFTR VPKRVYWEML ATNLTDKEYV RTRRALILEI 330        340        350        360
LIKAGSLKIE QIQDNLKKLG FDEVIETIEN DIKGLINTGI 370        380        390        400
FIEIKGRFYQ LKDHILQFVI PNRGVTKQLV KSELEEKKSE 410        420        430        440
LRHKLKYVPH EYIELIEIAR NSTQDRILEM KVMEFFMKVY 450        460        470        480
GYRGKHLGGS RKPDGAIYTV GSPIDYGVIV DTKAYSGGYN 490        500        510        520
LPIGQADEMQ RYVEENQTRN KHINPNEWWK VYPSSVTEFK 530        540        550        560
FLFVSGHFKG NYKAQLTRLN HITNCNGAVL SVEELLIGGE 570        580
MIKAGTLTLE EVRRKFNNGE INF
```

An exemplary nucleic acid sequence encoding FokI is as follows:

```
                                        (SEQ ID NO: 34)
ATGTTTTTGAGTATGGTTTCTAAAATAAGAACTTTCGGTTGGGTTCAAAA

TCCAGGTAAATTTGAGAATTTAAAACGAGTAGTTCAAGTATTTGATAGAA

ATTCTAAAGTACATAATGAAGTGAAAAATATAAAGATACCAACCCTAGTC

AAAGAAAGTAAGATCCAAAAAGAACTAGTTGCTATTATGAATCAACATGA

TTTGATTTATACATATAAAGAGTTAGTAGGAACAGGAACTTCAATACGTT

CAGAAGCACCATGCGATGCAATTATTCAAGCAACAATAGCAGATCAAGGA

AATAAAAAAGGCTATATCGATAATTGGTCATCTGACGGTTTTTTGCGTTG

GGCACATGCTTTAGGATTTATTGAATATATAAATAAAAGTGATTCTTTTG

TAATAACTGATGTTGGACTTGCTTACTCTAAATCAGCTGACGGCAGCGCC

ATTGAAAAAGAGATTTTGATTGAAGCGATATCATCTTATCCTCCAGCGAT

TCGTATTTTAACTTTGCTAGAAGATGGACAACATTTGACAAAGTTTGATC

TTGGCAAGAATTTAGGTTTTAGTGGAGAAAGTGGATTTACTTCTCTACCG

GAAGGAATTCTTTTAGATACTCTAGCTAATGCTATGCCTAAAGATAAAGG

CGAAATTCGTAATAATTGGGAAGGATCTTCAGATAAGTACGCAAGAATGA

TAGGTGGTTGGCTGGATAAACTAGGATTAGTAAAGCAAGGAAAAAAAGAA

TTTATCATTCCTACTTTGGGTAAGCCGGACAATAAAGAGTTTATATCCCA

CGCTTTTAAAATTACTGGAGAAGGTTTGAAAGTACTGCGTCGAGCAAAAG

GCTCTACAAAATTTACACGTGTACCTAAAAGAGTATATTGGGAAATGCTT

GCTACAAACCTAACCGATAAAGAGTATGTAAGAACAAGAAGAGCTTTGAT

TTTAGAAATATTAATCAAAGCTGGATCATTAAAAATAGAACAAATACAAG

ACAACTTGAAGAAATTAGGATTTGATGAAGTTATAGAAACTATTGAAAAT

GATATCAAAGGCTTAATTAACACAGGTATATTTATAGAAATCAAAGGGCG

ATTTTATCAATTGAAAGACCATATTCTTCAATTTGTAATACCTAATCGTG

GTGTGACTAAGCAACTAGTCAAAAGTGAACTGGAGGAGAAGAAATCTGAA

CTTCGTCATAAATTGAAATATGTGCCTCATGAATATATTGAATTAATTGA

AATTGCCAGAAATTCCACTCAGGATAGAATTCTTGAAATGAAGGTAATGG

AATTTTTTATGAAAGTTTATGGATATAGAGGTAAACATTTGGGTGGATCA

AGGAAACCGGACGGAGCAATTTATACTGTCGGATCTCCTATTGATTACGG

TGTGATCGTGGATACTAAAGCTTATAGCGGAGGTTATAATCTGCCAATTG

GCCAAGCAGATGAAATGCAACGATATGTCGAAGAAAATCAAACACGAAAC

AAACATATCAACCCTAATGAATGGTGGAAAGTCTATCCATCTTCTGTAAC

GGAATTTAAGTTTTTATTTGTGAGTGGTCACTTTAAAGGAAACTACAAAG

CTCAGCTTACACGATTAAATCATATCACTAATTGTAATGGAGCTGTTCTT

AGTGTAGAAGAGCTTTTAATTGGTGGAGAAATGATTAAAGCCGGCACATT

AACCTTAGAGGAAGTGAGACGGAAATTTAATAACGGCGAGATAAACTTTT

AA
```

In some embodiments, the FokI nuclease used herein is at least about 50% identical SEQ ID NO:33, e.g., to amino acids 388-583 or 408-583 of SEQ ID NO:33. These variant nucleases must retain the ability to cleave DNA. In some embodiments, the nucleotide sequences are about 50%, 55%, 60%, 65%, 70%, 75%, 80%, 85%, 90%, 95%, 99% or 100% identical to amino acids 388-583 or 408-583 of SEQ ID NO:4. In some embodiments, any differences from amino acids 388-583 or 408-583 of SEQ ID NO:4 are in non-conserved regions.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence is aligned). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Heterologous Functional Domains

The transcriptional activation domains can be fused on the N or C terminus of the Cas9. In addition, although the present description exemplifies transcriptional activation domains, other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih..gov/pub/aravind/DONS/supplementary_material_DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 fused to MS2 coat protein, endoribonuclease Csy4, or lambda N can be used to recruit a long non-coding RNA (lncRNA) such as XIST or HOTAIR; see, e.g., Keryer-Bibens et al., Biol. Cell 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 binding site using the methods and compositions described herein. In some embodiments, the Csy4 is catalytically inactive.

In some embodiments, the fusion proteins include a linker between the dCas9 and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:14) or GGGGS (SEQ ID NO:15), e.g., two, three, four, or more repeats of the GGGS (SEQ ID NO:14) or GGGGS (SEQ ID NO:15) unit. Other linker sequences can also be used.

Cas9

Cas9 molecules of a variety of species can be used in the methods and compositions described herein. While the *S. pyogenes* and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them. Such species include those set forth in the following table, which was created based on supplementary FIG. 1 of Chylinski et al., 2013.

| Alternative Cas9 proteins | |
|---|---|
| GenBank Acc No. | Bacterium |
| 303229466 | *Veillonella atypica* ACS-134-V-Col7a |
| 34762592 | *Fusobacterium nucleatum* subsp. *vincentii* |
| 374307738 | *Filifactor alocis* ATCC 35896 |
| 320528778 | *Solobacterium moorei* F0204 |
| 291520705 | *Coprococcus catus* GD-7 |
| 42525843 | *Treponema denticola* ATCC 35405 |
| 304438954 | *Peptoniphilus duerdenii* ATCC BAA-1640 |
| 224543312 | *Catenibacterium mitsuokai* DSM 15897 |
| 24379809 | *Streptococcus mutans* UA159 |
| 15675041 | *Streptococcus pyogenes* SF370 |
| 16801805 | *Listeria innocua* Clip11262 |
| 116628213 | *Streptococcus thermophilus* LMD-9 |
| 323463801 | *Staphylococcus pseudintermedius* ED99 |
| 352684361 | *Acidaminococcus intestini* RyC-MR95 |
| 302336020 | *Olsenella uli* DSM 7084 |
| 366983953 | *Oenococcus kitaharae* DSM 17330 |
| 310286728 | *Bifidobacterium bifidum* S17 |
| 258509199 | *Lactobacillus rhamnosus* GG |
| 300361537 | *Lactobacillus gasseri* JV-V03 |
| 169823755 | *Finegoldia magna* ATCC 29328 |
| 47458868 | *Mycoplasma mobile* 163K |
| 284931710 | *Mycoplasma gallisepticum* str. F |
| 363542550 | *Mycoplasma ovipneumoniae* SC01 |
| 384393286 | *Mycoplasma canis* PG 14 |
| 71894592 | *Mycoplasma synoviae* 53 |
| 238924075 | *Eubacterium rectale* ATCC 33656 |
| 116627542 | *Streptococcus thermophilus* LMD-9 |
| 315149830 | *Enterococcus faecalis* TX0012 |
| 315659848 | *Staphylococcus lugdunensis* M23590 |
| 160915782 | *Eubacterium dolichum* DSM 3991 |
| 336393381 | *Lactobacillus coryniformis* subsp. *torquens* |
| 310780384 | *Ilyobacter polytropus* DSM 2926 |
| 325677756 | *Ruminococcus albus* 8 |

Alternative Cas9 proteins

| GenBank Acc No. | Bacterium |
|---|---|
| 187736489 | *Akkermansia muciniphila* ATCC BAA-835 |
| 117929158 | *Acidothermus cellulolyticus* 11B |
| 189440764 | *Bifidobacterium longum* DJO10A |
| 283456135 | *Bifidobacterium dentium* Bd1 |
| 38232678 | *Corynebacterium diphtheriae* NCTC 13129 |
| 187250660 | *Elusimicrobium minutum* Pei191 |
| 319957206 | *Nitratifractor salsuginis* DSM 16511 |
| 325972003 | *Sphaerochaeta globus* str. Buddy |
| 261414553 | *Fibrobacter succinogenes* subsp. *succinogenes* |
| 60683389 | *Bacteroides fragilis* NCTC 9343 |
| 256819408 | *Capnocytophaga ochracea* DSM 7271 |
| 90425961 | *Rhodopseudomonas palustris* BisB18 |
| 373501184 | *Prevotella micans* F0438 |
| 294674019 | *Prevotella ruminicola* 23 |
| 365959402 | *Flavobacterium columnare* ATCC 49512 |
| 312879015 | *Aminomonas paucivorans* DSM 12260 |
| 83591793 | *Rhodospirillum rubrum* ATCC 11170 |
| 294086111 | *Candidatus Puniceispirillum marinum* IMCC1322 |
| 121608211 | *Verminephrobacter eiseniae* EF01-2 |
| 344171927 | *Ralstonia syzygii* R24 |
| 159042956 | *Dinoroseobacter shibae* DFL 12 |
| 288957741 | *Azospirillum* sp- B510 |
| 92109262 | *Nitrobacter hamburgensis* X14 |
| 148255343 | *Bradyrhizobium* sp- BTAi1 |
| 34557790 | *Wolinella succinogenes* DSM 1740 |
| 218563121 | *Campylobacter jejuni* subsp. *jejuni* |
| 291276265 | *Helicobacter mustelae* 12198 |
| 229113166 | *Bacillus cereus* Rock1-15 |
| 222109285 | *Acidovorax ebreus* TPSY |
| 189485225 | uncultured Termite group 1 |
| 182624245 | *Clostridium perfringens* D str. |
| 220930482 | *Clostridium cellulolyticum* H10 |
| 154250555 | *Parvibaculum lavamentivorans* DS-1 |
| 257413184 | *Roseburia intestinalis* L1-82 |
| 218767588 | *Neisseria meningitidis* Z2491 |
| 15602992 | *Pasteurella multocida* subsp. *multocida* |
| 319941583 | *Sutterella wadsworthensis* 3 1 |
| 254447899 | gamma proteobacterium HTCC5015 |
| 54296138 | *Legionella pneumophila* str. Paris |
| 331001027 | *Parasutterella excrementihominis* YIT 11859 |
| 34557932 | *Wolinella succinogenes* DSM 1740 |
| 118497352 | *Francisella novicida* U112 |

The constructs and methods described herein can include the use of any of those Cas9 proteins, and their corresponding guide RNAs or other guide RNAs that are compatible. The Cas9 from *Streptococcus thermophilus* LMD-9 CRISPR1 system has also been shown to function in human cells in Cong et al (Science 339, 819 (2013)). Cas9 orthologs from *N. meningitides* are described in Hou et al., Proc Natl Acad Sci USA. 2013 Sep. 24; 110(39):15644-9 and Esvelt et al., Nat Methods. 2013 November; 10(11):1116-21. Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells. In some embodiments, a catalytically inactive Cas9 (dCas9) containing mutations at (i) D10, E762, H983, or D986 and (i) H840 or N863, e.g., D10A/D10N and H840A/H840N/H840Y, to render the nuclease portion of the protein completely catalytically inactive; substitutions at these positions could be alanine (as they are in Nishimasu., Cell 156, 935-949 (2014)) or they could be other residues, e.g., glutamine, asparagine, tyrosine, serine, or aspartate, e.g., E762Q, H983N, H983Y, D986N, N863D, N863S, or N863H (FIG. 1C). To render the Cas9 partially inactive, e.g., to create a nickase that cuts only one strand, a mutation at any of D10, E762, H983, D986, H840, or N863 can be introduced. The wild type sequence of *S. pyogenes* Cas9 nuclease that can be used in the methods and compositions described herein is as follows.

```
                                         (SEQ ID NO: 18)
         10         20         30         40
MDKKYSIGLD IGTNSVGWAV ITDEYKVPSK KFKVLGNTDR 50         60         70         80
HSIKKNLIGA LLFDSGETAE ATRLKRTARR RYTRRKNRIC 90        100        110        120
YLQEIFSNEM AKVDDSFFHR LEESFLVEED KKHERHPIFG 130        140        150        160
NIVDEVAYHE KYPTIYHLRK KLVDSTDKAD LRLIYLALAH 170        180        190        200
MIKFRGHFLI EGDLNPDNSD VDKLFIQLVQ TYNQLFEENP 210        220        230        240
INASGVDAKA ILSARLSKSR RLENLIAQLP GEKKNGLFGN 250        260        270        280
LIALSLGLTP NFKSNFDLAE DAKLQLSKDT YDDDLDNLLA 290        300        310        320
QIGDQYADLF LAAKNLSDAI LLSDILRVNT EITKAPLSAS 330        340        350        360
MIKRYDEHHQ DLTLLKALVR QQLPEKYKEI FFDQSKNGYA 370        380        390        400
GYIDGGASQE EFYKFIKPIL EKMDGTEELL VKLNREDLLR 410        420        430        440
KQRTFDNGSI PHQIHLGELH AILRRQEDFY PFLKDNREKI 450        460        470        480
EKILTFRIPY YVGPLARGNS RFAWMTRKSE ETITPWNFEE 490        500        510        520
VVDKGASAQS FIERMTNFDK NLPNEKVLPK HSLLYEYFTV 530        540        550        560
YNELTKVKYV TEGMRKPAFL SGEQKKAIVD LLFKTNRKVT 570        580        590        600
VKQLKEDYFK KIECFDSVEI SGVEDRFNAS LGTYHDLLKI 610        620        630        640
IKDKDFLDNE ENEDILEDIV LTLTLFEDRE MIEERLKTYA 650        660        670        680
HLFDDKVMKQ LKRRRYTGWG RLSRKLINGI RDKQSGKTIL 690        700        710        720
DFLKSDGFAN RNFMQLIHDD SLTFKEDIQK AQVSGQGDSL 730        740        750        760
HEHIANLAGS PAIKKGILQT VKVVDELVKV MGRHKPENIV 770        780        790        800
IEMARENQTT QKGQKNSRER MKRIEEGIKE LGSQILKEHP 810        820        830        840
VENTQLQNEK LYLYYLQNGR DMYVDQELDI NRLSDYDVDH 850        860        870        880
IVPQSFLKDD SIDNKVLTRS DKNRGKSDNV PSEEVVKKMK 890        900        910        920
NYWRQLLNAK LITQRKFDNL TKAERGGLSE LDKAGFIKRQ 930        940        950        960
LVETRQITKH VAQILDSRMN TKYDENDKLI REVKVITLKS
```

```
         970        980        990       1000
KLVSDFRKDF QFYKVREINN YHHAHDAYLN AVVGTALIKK 1010       1020       1030       1040
YPKLESEFVY GDYKVYDVRK MIAKSEQEIG KATAKYFFYS 1050       1060       1070       1080
NIMNFFKTEI TLANGEIRKR PLIETNGETG EIVWDKGRDF 1090       1100       1110       1120
ATVRKVLSMP QVNIVKKTEV QTGGFSKESI LPKRNSDKLI 1130       1140       1150       1160
ARKKDWDPKK YGGFDSPTVA YSVLVVAKVE KGKSKKLKSV 1170       1180       1190       1200
KELLGITIME RSSFEKNPID FLEAKGYKEV KKDLIIKLPK 1210       1220       1230       1240
YSLFELENGR KRMLASAGEL QKGNELALPS KYVNFLYLAS 1250       1260       1270       1280
HYEKLKGSPE DNEQKQLFVE QHKHYLDEII EQISEFSKRV 1290       1300       1310       1320
ILADANLDKV LSAYNKHRDK PIREQAENII HLFTLTNLGA 1330       1340       1350       1360
PAAFKYFDTT IDRKRYTSTK EVLDATLIHQ SITGLYETRI

DLSQLGGD
```

In some embodiments, the Cas9 nuclease used herein is at least about 50% identical to the sequence of *S. pyogenes* Cas9, i.e., at least 50% identical to SEQ ID NO:18. In some embodiments, the nucleotide sequences are about 50%, 55%, 60%, 65%, 70%, 75%, 80%, 85%, 90%, 95%, 99% or 100% identical to SEQ ID NO:18. In some embodiments, any differences from SEQ ID NO:18 are in non-conserved regions, as identified by sequence alignment of sequences set forth in Chylinski et al., RNA Biology 10:5, 1-12; 2013 (e.g., in supplementary FIG. 1 and supplementary table 1 thereof); Esvelt et al., Nat Methods. 2013 November; 10(11):1116-21 and Fonfara et al., Nucl. Acids Res. (2014) 42 (4): 2577-2590. [Epub ahead of print 2013 Nov. 22] doi:10.1093/nar/gkt1074.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 50% (in some embodiments, about 50%, 55%, 60%, 65%, 70%, 75%, 85%, 90%, 95%, or 100% of the length of the reference sequence is aligned). The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For purposes of the present application, the percent identity between two amino acid sequences is determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Expression Systems

In order to use the fusion proteins and guide RNAs described, it may be desirable to express the engineered proteins from a nucleic acid that encodes them. This can be performed in a variety of ways. For example, the nucleic acid encoding the fusion protein or guide RNA can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or guide RNA for production of the fusion protein or guide RNA. The nucleic acid encoding the fusion protein or guide RNA can also be cloned into an expression vector, for administration to a plant cell, animal cell, preferably a mammalian cell or a human cell, fungal cell, bacterial cell, or protozoan cell.

To obtain expression, a sequence encoding a fusion protein or guide RNA is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a fusion protein nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to trans activation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein (MBP). Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the guide RNAs can include RNA Pol III promoters to drive expression of the guide RNAs, e.g., the H1, U6 or 7SK promoters. These human promoters allow for expression of gRNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the fusion protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the DBD domain itself, or another functional domain within the final chimeric protein, has intrinsic nuclear translocation function.

The present invention includes the vectors and cells comprising the vectors.

EXAMPLES

The invention is further described in the following examples, which do not limit the scope of the invention described in the claims.

Example 1. Assessing Specificity of RNA-Guided Endonucleases

CRISPR RNA-guided nucleases (RGNs) have rapidly emerged as a platform for genome editing. This example describes the use of a human cell-based reporter assay to characterize off-target cleavage of CasAS9-based RGNs.

Materials and Methods

The following materials and methods were used in Example 1.

Construction of Guide RNAs

DNA oligonucleotides harboring variable 20 nt sequences for Cas9 targeting were annealed to generate short double-strand DNA fragments with 4 bp overhangs compatible with ligation into BsmBI-digested plasmid pMLM3636. Cloning of these annealed oligonucleotides generates plasmids encoding a chimeric+103 single-chain guide RNA with 20 variable 5' nucleotides under expression of a U6 promoter (Hwang et al., Nat Biotechnol 31, 227-229 (2013); Mali et al., Science 339, 823-826 (2013).). pMLM3636 and the expression plasmid pJDS246 (encoding a codon optimized version of Cas9) used in this study are both available through the non-profit plasmid distribution service Addgene (addgene.org/crispr-cas).

EGFP Activity Assays

U2OS.EGFP cells harboring a single integrated copy of an EGFP-PEST fusion gene were cultured as previously described (Reyon et al., Nat Biotech 30, 460-465 (2012)). For transfections, 200,000 cells were Nucleofected with the indicated amounts of gRNA expression plasmid and pJDS246 together with 30 ng of a Td-tomato-encoding plasmid using the SE Cell Line 4D-Nucleofector™ X Kit (Lonza) according to the manufacturer's protocol. Cells were analyzed 2 days post-transfection using a BD LSRII flow cytometer. Transfections for optimizing gRNA/Cas9 plasmid concentration were performed in triplicate and all other transfections were performed in duplicate.

PCR Amplification and Sequence Verification of Endogenous Human Genomic Sites

PCR reactions were performed using Phusion Hot Start II high-fidelity DNA polymerase (NEB) with PCR primers and conditions listed in Table B. Most loci amplified successfully using touchdown PCR (98° C., 10 s; 72-62° C., −1° C./cycle, 15 s; 72° C., 30 s]10 cycles, [98° C., 10 s; 62° C., 15 s; 72° C., 30 s]25 cycles). PCR for the remaining targets were performed with 35 cycles at a constant annealing temperature of 68° C. or 72° C. and 3% DMSO or 1M betaine, if necessary. PCR products were analyzed on a QIAXCEL capillary electrophoresis system to verify both size and purity. Validated products were treated with ExoSap-IT (Affymetrix) and sequenced by the Sanger method (MGH DNA Sequencing Core) to verify each target site.

Determination of RGN-Induced On- and Off-Target Mutation Frequencies in Human Cells For U2OS.EGFP and K562 cells, 2×10$^5$ cells were transfected with 250 ng of gRNA expression plasmid or an empty U6 promoter plasmid (for negative controls), 750 ng of Cas9 expression plasmid, and 30 ng of td-Tomato expression plasmid using the 4D Nucleofector System according to the manufacturer's instructions (Lonza). For HEK293 cells, 1.65×10$^5$ cells were transfected with 125 ng of gRNA expression plasmid or an empty U6 promoter plasmid (for the negative control), 375 ng of Cas9 expression plasmid, and 30 ng of a td-Tomato expression plasmid using Lipofectamine LTX reagent according to the manufacturer's instructions (Life Technologies). Genomic DNA was harvested from transfected U2OS.EGFP, HEK293, or K562 cells using the QIAamp DNA Blood Mini Kit (QIAGEN), according to the manufacturer's instructions. To generate enough genomic DNA to amplify the off-target candidate sites, DNA from three Nucleofections (for U2OS.EGFP cells), two Nucleofections (for K562 cells), or two Lipofectamine LTX transfections was pooled together before performing T7EI. This was done twice for each condition tested, thereby generating duplicate pools of genomic DNA representing a total of four or six individual transfections. PCR was then performed using these genomic DNAs as templates as described above and purified using Ampure XP beads (Agencourt) according to the manufacturer's instructions. T7EI assays were performed as previously described (Reyon et al., 2012, supra).

DNA Sequencing of NHEJ-Mediated Indel Mutations

Purified PCR products used for the T7EI assay were cloned into Zero Blunt TOPO vector (Life Technologies) and plasmid DNAs were isolated using an alkaline lysis miniprep method by the MGH DNA Automation Core. Plasmids were sequenced using an M13 forward primer (5'-GTAAAACGACGGCCAG-3' (SEQ ID NO:35)) by the Sanger method (MGH DNA Sequencing Core).

Example 1a. Single Nucleotide Mismatches

To begin to define the specificity determinants of RGNs in human cells, a large-scale test was performed to assess the effects of systematically mismatching various positions within multiple gRNA/target DNA interfaces. To do this, a quantitative human cell-based enhanced green fluorescent protein (EGFP) disruption assay previously described (see Methods above and Reyon et al., 2012, supra) that enables rapid quantitation of targeted nuclease activities (FIG. 2B) was used. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end joining (NHEJ) repair of nuclease-induced double-stranded breaks (DSBs) (FIG. 2B). For the studies described here, three ~100 nt single gRNAs (gRNAs) targeted to different sequences within EGFP were used, as follows:

```
                                           SEQ ID NO: 1
    EGFP Site 1 GGGCACGGGCAGCTTGCCGGTGG SEQ ID NO: 2
    EGFP Site 2 GATGCCGTTCTTCTGCTTGTCGG SEQ ID NO: 3
    EGFP Site 3 GGTGGTGCAGATGAACTTCAGGG
```

Each of these gRNAs can efficiently direct Cas9-mediated disruption of EGFP expression (see Example 1e and 2a, and FIGS. 3E (top) and 3F (top)).

In initial experiments, the effects of single nucleotide mismatches at 19 of 20 nucleotides in the complementary targeting region of three EGFP-targeted gRNAs were tested. To do this, variant gRNAs were generated for each of the three target sites harboring Watson-Crick transversion mismatches at positions 1 through 19 (numbered 1 to 20 in the 3' to 5' direction; see FIG. 1) and the abilities of these various gRNAs to direct Cas9-mediated EGFP disruption in human cells tested (variant gRNAs bearing a substitution at position 20 were not generated because this nucleotide is part of the U6 promoter sequence and therefore must remain a guanine to avoid affecting expression.)

For EGFP target site #2, single mismatches in positions 1-10 of the gRNA have dramatic effects on associated Cas9 activity (FIG. 2C, middle panel), consistent with previous studies that suggest mismatches at the 5' end of gRNAs are better tolerated than those at the 3' end (Jiang et al., Nat Biotechnol 31, 233-239 (2013); Cong et al., Science 339, 819-823 (2013); Jinek et al., Science 337, 816-821 (2012)). However, with EGFP target sites #1 and #3, single mismatches at all but a few positions in the gRNA appear to be well tolerated, even within the 3' end of the sequence. Furthermore, the specific positions that were sensitive to mismatch differed for these two targets (FIG. 2C, compare top and bottom panels)—for example, target site #1 was particularly sensitive to a mismatch at position 2 whereas target site #3 was most sensitive to mismatches at positions 1 and 8.

Example 1b. Multiple Mismatches

To test the effects of more than one mismatch at the gRNA/DNA interface, a series of variant gRNAs bearing double Watson-Crick transversion mismatches in adjacent and separated positions were created and the abilities of these gRNAs to direct Cas9 nuclease activity were tested in human cells using the EGFP disruption assay. All three target sites generally showed greater sensitivity to double alterations in which one or both mismatches occur within the 3' half of the gRNA targeting region. However, the magnitude of these effects exhibited site-specific variation, with target site #2 showing the greatest sensitivity to these double mismatches and target site #1 generally showing the least. To test the number of adjacent mismatches that can be tolerated, variant gRNAs were constructed bearing increasing numbers of mismatched positions ranging from positions 19 to 15 in the 5' end of the gRNA targeting region (where single and double mismatches appeared to be better tolerated).

Testing of these increasingly mismatched gRNAs revealed that for all three target sites, the introduction of three or more adjacent mismatches results in significant loss of RGN activity. A sudden drop off in activity occurred for three different EGFP-targeted gRNAs as one makes progressive mismatches starting from position 19 in the 5' end and adding more mismatches moving toward the 3' end. Specifically, gRNAs containing mismatches at positions 19 and 19+18 show essentially full activity whereas those with mismatches at positions 19+18+17, 19+18+17+16, and 19+18+17+16+15 show essentially no difference relative to a negative control (FIG. 2F). (Note that we did not mismatch position 20 in these variant gRNAs because this position needs to remain as a G because it is part of the U6 promoter that drives expression of the gRNA.)

Additional proof of that shortening gRNA complementarity might lead to RGNs with greater specificities was obtained in the following experiment: for four different EGFP-targeted gRNAs (FIG. 2H), introduction of a double mismatch at positions 18 and 19 did not significantly impact activity. However, introduction of another double mismatch at positions 10 and 11 then into these gRNAs results in near complete loss of activity. Interestingly introduction of only the 10/11 double mismatches does not generally have as great an impact on activity.

Taken together, these results in human cells confirm that the activities of RGNs can be more sensitive to mismatches in the 3' half of the gRNA targeting sequence. However, the data also clearly reveal that the specificity of RGNs is complex and target site-dependent, with single and double mismatches often well tolerated even when one or more mismatches occur in the 3' half of the gRNA targeting region. Furthermore, these data also suggest that not all mismatches in the 5' half of the gRNA/DNA interface are necessarily well tolerated.

In addition, these results strongly suggest that gRNAs bearing shorter regions of complementarity (specifically ~17 nts) will be more specific in their activities. We note that 17 nts of specificity combined with the 2 nts of specificity conferred by the PAM sequence results in specification of a 19 bp sequence, one of sufficient length to be unique in large complex genomes such as those found in human cells.

Example 1c. Off-Target Mutations

To determine whether off-target mutations for RGNs targeted to endogenous human genes could be identified, six gRNAs that target three different sites in the VEGFA gene, one in the EMX1 gene, one in the RNF2 gene, and one in the FANCF gene were used. These six gRNAs efficiently directed Cas9-mediated indels at their respective endogenous loci in human U2OS.EGFP cells as detected by T7 Endonuclease I (T7EI) assay. For each of these six RGNs, we then examined dozens of potential off-target sites (ranging in number from 46 to as many as 64) for evidence of nuclease-induced NHEJ-mediated indel mutations in U2OS.EGFP cells. The loci assessed included all genomic sites that differ by one or two nucleotides as well as subsets of genomic sites that differ by three to six nucleotides and with a bias toward those that had one or more of these mismatches in the 5' half of the gRNA targeting sequence. Using the T7EI assay, four off-target sites (out of 53 candidate sites examined) for VEGFA site 1, twelve (out of 46 examined) for VEGFA site 2, seven (out of 64 examined) for VEGFA site 3 and one (out of 46 examined) for the EMX1 site were readily identified. No off-target mutations were detected among the 43 and 50 potential sites examined for the RNF2 or FANCF genes, respectively. The rates of mutation at verified off-target sites were very high, ranging from 5.6% to 125% (mean of 40%) of the rate observed at the intended target site. These bona fide off-targets included sequences with mismatches in the 3' end of the target site and with as many as a total of five mismatches, with most off-target sites occurring within protein coding genes. DNA sequencing of a subset of off-target sites provided additional molecular confirmation that indel mutations occur at the expected RGN cleavage site.

Example 1d. Off-Target Mutations in Other Cell Types

Having established that RGNs can induce off-target mutations with high frequencies in U2OS.EGFP cells, we next sought to determine whether these nucleases would also have these effects in other types of human cells. We had chosen U2OS.EGFP cells for our initial experiments because we previously used these cells to evaluate the activities of TALENs[15] but human HEK293 and K562 cells have been more widely used to test the activities of targeted nucleases. Therefore, we also assessed the activities of the four RGNs targeted to VEGFA sites 1, 2, and 3 and the EMX1 site in HEK293 and K562 cells. We found that each of these four RGNs efficiently induced NHEJ-mediated indel mutations at their intended on-target site in these two additional human cell lines (as assessed by T7EI assay), albeit with somewhat lower mutation frequencies than those observed in U2OS.EGFP cells. Assessment of the 24 off-target sites for these four RGNs originally identified in U2OS.EGFP cells revealed that many were again mutated in HEK293 and K562 cells with frequencies similar to those at their corresponding on-target site. DNA sequencing of a subset of these off-target sites from HEK293 cells provided additional molecular evidence that alterations are occurring at the expected genomic loci. We do not know for certain why in HEK293 cells four and in K562 cells eleven of the off-target sites identified in U2OS.EGFP cells did not show detectable mutations. However, we note that many of these off-target sites also showed relatively lower mutation frequencies in U2OS.EGFP cells. Therefore, we speculate that mutation rates of these sites in HEK293 and K562 cells may be falling below the reliable detection limit of our T7EI assay (~2-5%) because RGNs generally appear to have lower activities in HEK293 and K562 cells compared with U2OS.EGFP cells in our experiments. Taken together, our results in HEK293 and K562 cells provide evidence that the high-frequency off-target mutations we observe with RGNs will be a general phenomenon seen in multiple human cell types.

Example 1e. Titration of gRNA- and Cas9-Expressing Plasmid Amounts Used for the EGFP Disruption Assay Single guide RNAs (gRNAs) were generated for three different sequences (EGFP SITES 1-3, shown above) located upstream of EGFP nucleotide 502, a position at which the introduction of frameshift mutations via non-homologous end-joining can robustly disrupt expression of EGFP (Maeder, M. L. et al., Mol Cell 31, 294-301 (2008); Reyon, D. et al., Nat Biotech 30, 460-465 (2012)).

For each of the three target sites, a range of gRNA-expressing plasmid amounts (12.5 to 250 ng) was initially transfected together with 750 ng of a plasmid expressing a codon-optimized version of the Cas9 nuclease into our U2OS.EGFP reporter cells bearing a single copy, constitutively expressed EGFP-PEST reporter gene. All three RGNs efficiently disrupted EGFP expression at the highest concentration of gRNA plasmid (250 ng) (FIG. 3E (top)). However, RGNs for target sites #1 and #3 exhibited equivalent levels of disruption when lower amounts of gRNA-expressing plasmid were transfected whereas RGN activity at target site #2 dropped immediately when the amount of gRNA-expressing plasmid transfected was decreased (FIG. 3E (top)).

The amount of Cas9-encoding plasmid (range from 50 ng to 750 ng) transfected into our U2OS.EGFP reporter cells was titrated EGFP disruption assayed. As shown in FIG. 3F (top), target site #1 tolerated a three-fold decrease in the amount of Cas9-encoding plasmid transfected without substantial loss of EGFP disruption activity. However, the activities of RGNs targeting target sites #2 and #3 decreased immediately with a three-fold reduction in the amount of Cas9 plasmid transfected (FIG. 3F (top)). Based on these results, 25 ng/250 ng, 250 ng/750 ng, and 200 ng/750 ng of gRNA-/Cas9-expressing plasmids were used for EGFP target sites #1, #2, and #3, respectively, for the experiments described in Examples 1a-1d.

The reasons why some gRNA/Cas9 combinations work better than others in disrupting EGFP expression is not understood, nor is why some of these combinations are more or less sensitive to the amount of plasmids used for transfection. Although it is possible that the range of off-target sites present in the genome for these three gRNAs might influence each of their activities, no differences were seen in the numbers of genomic sites that differ by one to six bps for each of these particular target sites that would account for the differential behavior of the three gRNAs.

Example 2. Using GuideRNAs Containing Csy4 Binding Sites with Cas9

Figure 6:
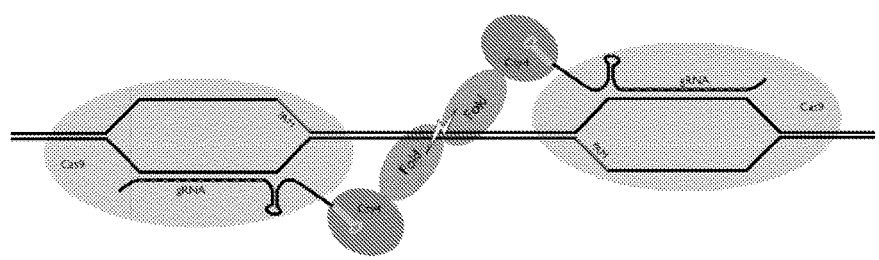

In this example, dCas9 is expressed together with a modified gRNA bearing extra RNA sequence on either or both of the 5' and/or 3' end of the gRNA that is bound by Csy4, an RNA-binding protein, as well as a fusion protein with Csy4 fused to the FokI nuclease domain. As shown in FIG. 6, two dCas9 molecules would be targeted to adjacent DNA sequences by appropriate gRNAs and the Csy4-binding sequence on the two gRNA would interact with the Csy4-FokI nuclease domain fusion proteins. The Fok nuclease domains would dimerize, resulting in introduction of a targeted double-stranded break in the DNA sequence between the two dCas9 binding sites.

Thus, Csy4 RNA binding sites were attached to the 3' and 5' ends of a gRNA sequence and expressed with Cas9 in cells. The Csy4 RNA binding site sequence 'GUUCACUGCCGUAUAGGCAGCUAAGAAA (SEQ ID NO:36)' was fused to the 5' and 3' end of the standard gRNA sequence.

Multiplex gRNA encoding plasmids were constructed by ligating: 1) annealed oligos encoding the first target site, 2) phosphorylated annealed oligos encoding crRNA, tracrRNA, and Csy4-binding site, and 3) annealed oligos encoding the second targetsite, into a U6-Csy4site-gRNA plasmid backbone digested with BsmBI Type IIs restriction enzyme.

(SEQ ID NO: 37)
GUUCACUGCCGUAUAGGCAGNNNNNNNNNNNNNNNNNNNNGUUUUAGAGC

UAGAAAUAGCAAGUUAAAAUAAGGCUAGUCCGUUAUCAACUUGAAAAAGU

GGCACCGAGUCGGUGCGUUCACUGCCGUAUAGGCAGNNNNNNNNNNNNNNN

NNNNNNNGUUUUAGAGCUAGAAAUAGCAAGUUAAAAUAAGGCUAGUCCGUU

AUCAACUUGAAAAAGUGGCACCGAGUCGGUGCGUUCACUGCCGUAUAGGC

AG

This sequence is a multiplex gRNA sequence flanked by Csy4 sites (underlined). When processed by Csy4FokI, Csy4FokI remains bound. Functionally, encoding these in multiplex on one transcript should have the same result as encoding them separately. Although all pairs of Csy4-flanked gRNAs were expressed in a multiplex context in the experiments described herein, the gRNAs can be encoded in multiplex gRNAs separated by Csy4 sites encoded on one transcript as well as individual gRNAs that have an additional Csy4 sequence. In this sequence, the first N20 sequence represents the sequence complementary to one strand of the target genomic sequence, and the second N20 sequence represents the sequence complementary to the other strand of the target genomic sequence.

A plasmid encoding the Csy4 recognition site containing gRNA was co-transfected with plasmid encoding Cas9 and Csy4 proteins separated by a '2A' peptide linkage. The results showed that gRNAs with Csy4 sites fused to the 5' and 3' ends remained capable of directing Cas9-mediated cleavage in human cells using the U2OS-EGFP disruption assay previously described. Thus, Csy4 RNA binding sites can be attached to 3' end of a gRNA sequence and complexes of these Csy4 site-containing gRNAs with Cas9 remain functional in the cell (FIG. 7A).

Additional experiments were performed to demonstrate that co-expression of two gRNAs targeted to adjacent sites on a DNA sequence and harboring a Csy4 binding site on their 3' ends, dCas9 protein, and a Csy4-FokI fusion in human cells can lead to cleavage and subsequent mutagenesis of the DNA between the two gRNA binding sites.

The sequences of the Csy4-FokI fusion proteins were as follows:
Csy4-FokI N-Terminal Fusion (Nucleotide Sequence)

(SEQ ID NO: 38)
ATGGACCACTACCTCGACATTCGCTTGCGACCGGACCCGGAATTTCCCCC

GGCGCAACTCATGAGCGTGCTCTTCGGCAAGCTCCACCAGGCCCTGGTGG

CACAGGGCGGGGACAGGATCGGCGTGAGCTTCCCCGACCTCGACGAAAGC

CGCTCCCGGCTGGGCGAGCGCCTGCGCATTCATGCCTCGGCGGACGACCT

TCGTGCCCTGCTCGCCCGGCCCTGGCTGGAAGGGTTGCGGGACCATCTGC

AATTCGGAGAACCGGCAGTCGTGCCTCACCCCACACCGTACCGTCAGGTC

AGTCGGGTTCAGGCGAAAAGCAATCCGGAACGCCTGCGCGCGGCGGCTCAT

GCGCCGGCACGATCTGAGTGAGGAGGAGGCTCGGAAACGCATTCCCGATA

CGGTCGCGAGAGCCTTGGACCTGCCCTTCGTCACGCTACGCAGCCAGAGC

ACCGGACAGCACTTCCGTCTCTTCATCCGCCACGGGCCGTTGCAGGTGAC

GGCAGAGGAAGGAGGATTCACCTGTTACGGGTTGAGCAAAGGAGGTTTCG

TTCCCTGGTTCGGTGGCGGTGGATCCCAACTAGTCAAAAGTGAACTGGAG

```
GAGAAGAAATCTGAACTTCGTCATAAATTGAAATATGTGCCTCATGAATA

TATTGAATTAATTGAAATTGCCAGAAATTCCACTCAGGATAGAATTCTTG

AAATGAAGGTAATGGAATTTTTTATGAAAGTTTATGGATATAGAGGTAAA

CATTTGGGTGGATCAAGGAAACCGGACGGAGCAATTTATACTGTCGGATC

TCCTATTGATTACGGTGTGATCGTGGATACTAAAGCTTATAGCGGAGGTT

ATAATCTGCCAATTGGCCAAGCAGATGAAATGCAACGATATGTCGAAGAA

AATCAAACACGAAACAAACATATCAACCCTAATGAATGGTGGAAAGTCTA

TCCATCTTCTGTAACGGAATTTAAGTTTTTATTTGTGAGTGGTCACTTTA

AAGGAAACTACAAAGCTCAGCTTACACGATTAAATCATATCACTAATTGT

AATGGAGCTGTTCTTAGTGTAGAAGAGCTTTTAATTGGTGGAGAAATGAT

TAAAGCCGGCACATTAACCTTAGAGGAAGTCAGACGGAAATTTAATAACG

GCGAGATAAACTTTTGA
```

Csy4-FokI N-Terminal Fusion (Amino Acid Sequence, GGGGS Linker Underlined)

```
                                       (SEQ ID NO: 39)
MDHYLDIRLRPDPEFPPAQLMSVLFGKLHQALVAQGGDRIGVSFPDLDES

RSRLGERLRIHASADDLRALLARPWLEGLRDHLQFGEPAVVPHPTPYRQV

SRVQAKSNPERLRRRLMRRHDLSEEEARKRIPDTVARALDLPFVTLRSQS

TGQHFRLFIRHGPLQVTAEEGGFTCYGLSKGGFVPWFGGGGSQLVKSELE

EKKSELRHKLKYVPHEYIELIEIARNSTQDRILEMKVMEFFMKVYGYRGK

HLGGSRKPDGAIYTVGSPIDYGVIVDTKAYSGGYNLPIGQADEMQRYVEE

NQTRNKHINPNEWWKVYPSSVTEFKFLFVSGHFKGNYKAQLTRLNHITNC

NGAVLSVEELLIGGEMIKAGTLTLEEVRRKFNNGEINF*
```

Csy4-FokI C-Terminal Fusion (Nucleotide Sequence)

```
                                       (SEQ ID NO: 40)
ATGCAACTAGTCAAAAGTGAACTGGAGGAGAAGAAATCTGAACTTCGTCA

TAAATTGAAATATGTGCCTCATGAATATATTGAATTAATTGAAATTGCCA

GAAATTCCACTCAGGATAGAATTCTTGAAATGAAGGTAATGGAATTTTTT

ATGAAAGTTTATGGATATAGAGGTAAACATTTGGGTGGATCAAGGAAACC

GGACGGAGCAATTTATACTGTCGGATCTCCTATTGATTACGGTGTGATCG

TGGATACTAAAGCTTATAGCGGAGGTTATAATCTGCCAATTGGCCAAGCA

GATGAAATGCAACGATATGTCGAAGAAATCAAACACGAAACAAACATAT

CAACCCTAATGAATGGTGGAAAGTCTATCCATCTTCTGTAACGGAATTTA

AGTTTTTATTTGTGAGTGGTCACTTTAAAGGAAACTACAAAGCTCAGCTT

ACACGATTAAATCATATCACTAATTGTAATGGAGCTGTTCTTAGTGTAGA

AGAGCTTTTAATTGGTGGAGAAATGATTAAAGCCGGCACATTAACCTTAG

AGGAAGTCAGACGGAAATTTAATAACGGCGAGATAAACTTTGGTGGCGGT

GGATCCGACCACTACCTCGACATTCGCTTGCGACCGGACCCGGAATTTCC

CCCGGCGCAACTCATGAGCGTGCTCTTCGGCAAGCTCCACCAGGCCCTGG

TGGCACAGGGCGGGGACAGGATCGGCGTGAGCTTCCCCGACCTCGACGAA

AGCCGCTCCCGGCTGGGCGAGCGCCTGCGCATTCATGCCTCGGCGGACGA

CCTTCGTGCCCTGCTCGCCCGGCCCTGGCTGGAAGGGTTGCGGGACCATC

TGCAATTCGGAGAACCGGCAGTCGTGCCTCACCCCACACCGTACCGTCAG

GTCAGTCGGGTTCAGGCGAAAAGCAATCCGGAACGCCTGCGGCGGCGGCT

CATGCGCCGGCACGATCTGAGTGAGGAGGAGGCTCGGAAACGCATTCCCG

ATACGGTCGCGAGAGCCTTGGACCTGCCCTTCGTCACGCTACGCAGCCAG

AGCACCGGACAGCACTTCCGTCTCTTCATCCGCCACGGGCCGTTGCAGGT

GACGGCAGAGGAAGGAGGATTCACCTGTTACGGGTTGAGCAAAGGAGGTT

TCGTTCCCTGGTTCTGA
```

Csy4-FokI C-Terminal Fusion (Amino Acid Sequence, GGGGS Linker Underlined)

```
                                       (SEQ ID NO: 41)
MQLVKSELEEKKSELRHKLKYVPHEYIELIEIARNSTQDRILEMKVMEFF

MKVYGYRGKHLGGSRKPDGAIYTVGSPIDYGVIVDTKAYSGGYNLPIGQA

DEMQRYVEENQTRNKHINPNEWWKVYPSSVTEFKFLFVSGHFKGNYKAQL

TRLNHITNCNGAVLSVEELLIGGEMIKAGTLTLEEVRRKFNNGEINFGGG

GSDHYLDIRLRPDPEFPPAQLMSVLFGKLHQALVAQGGDRIGVSFPDLDE

SRSRLGERLRIHASADDLRALLARPWLEGLRDHLQFGEPAVVPHPTPYRQ

VSRVQAKSNPERLRRRLMRRHDLSEEEARKRIPDTVARALDLPFVTLRSQ

STGQHFRLFIRHGPLQVTAEEGGFTCYGLSKGGFVPWF*
```

Because the orientation and geometry of the gRNA/dCas9/Csy4-FokI complexes required to induce a targeted DSB is not known, we performed a series of experiments designed to ascertain these parameters. For these experiments, we utilized a human cell-based EGFP disruption assay in which introduction of a targeted DSB into the coding sequence of a single integrated EGFP gene leads to the introduction of indel mutations and disruption of functional EGFP expression. Thus, the percentage of EGFP-negative cells, which can be quantified by flow cytometry, serves as a surrogate measure of targeted nuclease activity. To optimize parameters, we identified a large series of paired gRNA target sites that varied in the spacer length between the two sites (edge-to-edge distance between the N20NGG target sites). In addition, the orientation of the gRNA target sites were such that they either had their PAM sequences oriented "outward" from the spacer sequence in between or "inward" towards the spacer sequence in between. We expressed pairs of gRNAs targeted to these sites in our human EGFP reporter cell line together with dCas9 protein and either (a) a fusion of FokI nuclease domain fused to the amino-terminal end of Csy4 (FokI-Csy4 fusion protein) or (b) a fusion of FokI nuclease domain fused to the carboxy-terminal end of Csy4 (Csy4-FokI fusion protein) and then assessed by flow cytometry the efficiencies with which these combinations could induce EGFP-negative cells.

These experiments demonstrate that the FokI-Csy4 fusion proteins were most robustly active in concert with dCas9 and pairs of gRNA for sites in which the PAM sequences were oriented "outward" with spacer distances of 15-16 bp (FIG. 7C and data not shown).

Interestingly, there are also more moderate potential peaks of activity at spacer distances of 22 and 25 bps on the "outward" oriented sites. No activity was observed for the Csy4-FokI fusions on any of the "outward" oriented sites nor was any activity observed with either FokI-Csy4 or Csy4-FokI proteins for any pairs of sites in which the PAM sequences were oriented "inward" (data not shown). T7 endonuclease I assays demonstrated that the indel mutations induced by the gRNA/dCas9/FokI-Csy4 complexes were targeted to the expected location within the EGFP coding sequence (FIG. 7D). Thus, this configuration (depicted in FIG. 7B) enables gRNA/dCas9/FokI-Csy4 complexes to induce specific cleavage of DNA sequences that requires two gRNA binding sites, thereby increasing the specificity of the cleavage event.

REFERENCES

Cheng, A. W., Wang, H., Yang, H., Shi, L., Katz, Y., Theunissen, T. W., Rangarajan, S., Shivalila, C. S., Dadon, D. B., and Jaenisch, R. Multiplexed activation of endogenous genes by CRISPR-on, an RNA-guided transcriptional activator system. Cell Res 23, 1163-1171. (2013).

Cho, S. W., Kim, S., Kim, J. M. & Kim, J. S. Targeted genome engineering in human cells with the Cas9 RNA-guided endonuclease. Nat Biotechnol 31, 230-232 (2013).

Cong, L. et al. Multiplex genome engineering using CRISPR/Cas systems. Science 339, 819-823 (2013).

Cradick, T. J., Fine, E. J., Antico, C. J., and Bao, G. CRISPR/Cas9 systems targeting beta-globin and CCR5 genes have substantial off-target activity. Nucleic Acids Res. (2013).

Dicarlo, J. E. et al. Genome engineering in *Saccharomyces cerevisiae* using CRISPR-Cas systems. Nucleic Acids Res (2013).

Ding, Q., Regan, S. N., Xia, Y., Oostrom, L. A., Cowan, C. A., and Musunuru, K. Enhanced efficiency of human pluripotent stem cell genome editing through replacing TALENs with CRISPRs. Cell Stem Cell 12, 393-394. (2013).

Fisher, S., Barry, A., Abreu, J., Minie, B., Nolan, J., Delorey, T. M., Young, G., Fennell, T. J., Allen, A., Ambrogio, L., et al. A scalable, fully automated process for construction of sequence-ready human exome targeted capture libraries. Genome Biol 12, R1. (2011).

Friedland, A. E., Tzur, Y. B., Esvelt, K. M., Colaiacovo, M. P., Church, G. M., and Calarco, J. A. Heritable genome editing in *C. elegans* via a CRISPR-Cas9 system. Nat Methods 10, 741-743. (2013).

Fu, Y., Foden, J. A., Khayter, C., Maeder, M. L., Reyon, D., Joung, J. K., and Sander, J. D. High-frequency off-target mutagenesis induced by CRISPR-Cas nucleases in human cells. Nat Biotechnol 31, 822-826. (2013).

Gabriel, R. et al. An unbiased genome-wide analysis of zinc-finger nuclease specificity. Nat Biotechnol 29, 816-823 (2011).

Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-Mediated Modular RNA-Guided Regulation of Transcription in Eukaryotes. Cell 154, 442-451.

Gratz, S. J. et al. Genome engineering of *Drosophila* with the CRISPR RNA-guided Cas9 nuclease. Genetics (2013).

Hockemeyer, D. et al. Genetic engineering of human pluripotent cells using TALE nucleases. Nat Biotechnol 29, 731-734 (2011).

Horvath, P. & Barrangou, R. CRISPR/Cas, the immune system of bacteria and archaea. Science 327, 167-170 (2010).

Hsu, P. D., Scott, D. A., Weinstein, J. A., Ran, F. A., Konermann, S., Agarwala, V., Li, Y., Fine, E. J., Wu, X., Shalem, O., et al. DNA targeting specificity of RNA-guided Cas9 nucleases. Nat Biotechnol 31, 827-832. (2013).

Hwang, W. Y. et al. Efficient genome editing in zebrafish using a CRISPR-Cas system. Nat Biotechnol 31, 227-229 (2013).

Hwang, W. Y., Fu, Y., Reyon, D., Maeder, M. L., Kaini, P., Sander, J. D., Joung, J. K., Peterson, R. T., and Yeh, J. R. Heritable and Precise Zebrafish Genome Editing Using a CRISPR-Cas System. PLoS One 8, e68708. (2013a).

Jiang, W., Bikard, D., Cox, D., Zhang, F. & Marraffini, L. A. RNA-guided editing of bacterial genomes using CRISPR-Cas systems. Nat Biotechnol 31, 233-239 (2013).

Jinek, M. et al. A programmable dual-RNA-guided DNA endonuclease in adaptive bacterial immunity. Science 337, 816-821 (2012).

Jinek, M. et al. RNA-programmed genome editing in human cells. Elife 2, e00471 (2013).

Li, D., Qiu, Z., Shao, Y., Chen, Y., Guan, Y., Liu, M., Li, Y., Gao, N., Wang, L., Lu, X., et al. Heritable gene targeting in the mouse and rat using a CRISPR-Cas system. Nat Biotechnol 31, 681-683. (2013a).

Li, W., Teng, F., Li, T., and Zhou, Q. Simultaneous generation and germline transmission of multiple gene mutations in rat using CRISPR-Cas systems. Nat Biotechnol 31, 684-686. (2013b).

Maeder, M. L., Linder, S. J., Cascio, V. M., Fu, Y., Ho, Q. H., and Joung, J. K. CRISPR RNA-guided activation of endogenous human genes. Nat Methods 10, 977-979. (2013).

Mali, P., Aach, J., Stranges, P. B., Esvelt, K. M., Moosburner, M., Kosuri, S., Yang, L., and Church, G. M. CAS9 transcriptional activators for target specificity screening and paired nickases for cooperative genome engineering. Nat Biotechnol 31, 833-838. (2013a).

Mali, P., Esvelt, K. M., and Church, G. M. Cas9 as a versatile tool for engineering biology. Nat Methods 10, 957-963. (2013b).

Mali, P. et al. RNA-guided human genome engineering via Cas9. Science 339, 823-826 (2013c).

Pattanayak, V., Lin, S., Guilinger, J. P., Ma, E., Doudna, J. A., and Liu, D. R. High-throughput profiling of off-target DNA cleavage reveals RNA-programmed Cas9 nuclease specificity. Nat Biotechnol 31, 839-843. (2013).

Pattanayak, V., Ramirez, C. L., Joung, J. K. & Liu, D. R. Revealing off-target cleavage specificities of zinc-finger nucleases by in vitro selection. Nat Methods 8, 765-770 (2011).

Perez, E. E. et al. Establishment of HIV-1 resistance in CD4+ T cells by genome editing using zinc-finger nucleases. Nat Biotechnol 26, 808-816 (2008).

Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W., et al. RNA-guided gene activation by CRISPR-Cas9-based transcription factors. Nat Methods 10, 973-976. (2013).

Qi, L. S., Larson, M. H., Gilbert, L. A., Doudna, J. A., Weissman, J. S., Arkin, A. P., and Lim, W. A. Repurposing CRISPR as an RNA-guided platform for sequence-specific control of gene expression. Cell 152, 1173-1183. (2013).

Ran, F. A., Hsu, P. D., Lin, C. Y., Gootenberg, J. S., Konermann, S., Trevino, A. E., Scott, D. A., Inoue, A., Matoba, S., Zhang, Y., et al. Double nicking by RNA-guided CRISPR Cas9 for enhanced genome editing specificity. Cell 154, 1380-1389. (2013).

Reyon, D. et al. FLASH assembly of TALENs for high-throughput genome editing. Nat Biotech 30, 460-465 (2012).

Sander, J. D., Maeder, M. L., Reyon, D., Voytas, D. F., Joung, J. K., and Dobbs, D. ZiFiT (Zinc Finger Targeter): an updated zinc finger engineering tool. Nucleic Acids Res 38, W462-468. (2010).

Sander, J. D., Ramirez, C. L., Linder, S. J., Pattanayak, V., Shoresh, N., Ku, M., Foden, J. A., Reyon, D., Bernstein, B. E., Liu, D. R., et al. In silico abstraction of zinc finger nuclease cleavage profiles reveals an expanded landscape of off-target sites. Nucleic Acids Res. (2013).

Sander, J. D., Zaback, P., Joung, J. K., Voytas, D. F., and Dobbs, D. Zinc Finger Targeter (ZiFiT): an engineered zinc finger/target site design tool. Nucleic Acids Res 35, W599-605. (2007).

Shen, B. et al. Generation of gene-modified mice via Cas9/RNA-mediated gene targeting. Cell Res (2013).

Sugimoto, N. et al. Thermodynamic parameters to predict stability of RNA/DNA hybrid duplexes. Biochemistry 34, 11211-11216 (1995).

Terns, M. P. & Terns, R. M. CRISPR-based adaptive immune systems. Curr Opin Microbiol 14, 321-327 (2011).

Wang, H. et al. One-Step Generation of Mice Carrying Mutations in Multiple Genes by CRISPR/Cas-Mediated Genome Engineering. Cell 153, 910-918 (2013).

Wiedenheft, B., Sternberg, S. H. & Doudna, J. A. RNA-guided genetic silencing systems in bacteria and archaea. Nature 482, 331-338 (2012).

Yang, L., Guell, M., Byrne, S., Yang, J. L., De Los Angeles, A., Mali, P., Aach, J., Kim-Kiselak, C., Briggs, A. W., Rios, X., et al. (2013). Optimization of scarless human stem cell genome editing. Nucleic Acids Res 41, 9049-9061.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing a single or double-stranded break in a target region of a double-stranded DNA molecule in a cell, the method comprising expressing in or introducing into the cell:
   a *Streptococcus pyogenes* Cas9 nuclease or nickase; and
   a guide RNA that consists of a sequence selected from the group consisting of:

$$(X_{17-20}) \text{GUUUUAGAGCUAUGCUGUUUUG}(X_N); \quad \text{(SEQ ID NO: 4)}$$

$$(X_{17-20}) \text{GUUUUAGAGCUA}; \quad \text{(SEQ ID NO: 5)}$$

$$(X_{17-20}) \text{GUUUUAGAGCUAUGCUGUUUUG}; \quad \text{(SEQ ID NO: 6)}$$

$$(X_{17-20}) \text{GUUUUAGAGCUAUGCU}; \quad \text{(SEQ ID NO: 7)}$$

$$(X_{17-20}) \text{GUUUUAGAGCUAGAAAUAGCAAGUUAAAAUAAGGCUAGUCCG}(X_N); \quad \text{(SEQ ID NO: 8)}$$

$$(X_{17-20}) \text{GUUUUAGAGCUAUGCUGAAAAGCAUAGCAAGUUAAAAUAAGG CUAGUCCGUUAUC}(X_N); \quad \text{(SEQ ID NO: 9)}$$

$$(X_{17-20}) \text{GUUUUAGAGCUAUGCUGUUUUGGAAACAAAACAGCAUAGCAA GUUAAAAUAAGGCUAGUCCGUUAUC}(X_N); \quad \text{(SEQ ID NO: 10)}$$

$$(X_{17-20}) \text{GUUUUAGAGCUAGAAAUAGCAAGUUAAAAUAAGGCUAGUCCG UUAUCAACUUGAAAAAGUGGCACCGAGUCGGUGC}(X_N), \quad \text{(SEQ ID NO: 11)}$$

$$(X_{17-20}) \text{GUUUAAGAGCUAGAAAUAGCAAGUUUAAAUAAGGCUAGUCCG UUAUCAACUUGAAAAAGUGGCACCGAGUCGGUGC}; \quad \text{(SEQ ID NO: 12)}$$

$$(X_{17-20}) \text{GUUUUAGAGCUAUGCUGGAAACAGCAUAGCAAGUUUAAAUAA GGCUAGUCCGUUAUCAACUUGAAAAAGUGGCACCGAGUCGGUGC}; \quad \text{(SEQ ID NO: 13)}$$

or $$(X_{17-20}) \text{GUUUAAGAGCUAUGCUGGAAACAGCAUAGCAAGUUUAAAUAA GGCUAGUCCGUUAUCAACUUGAAAAAGUGGCACCGAGUCGGUGC}; \quad \text{(SEQ ID NO: 14)}$$

wherein $X_{17-20}$ is a sequence complementary to 17-20 consecutive nucleotides of the complementary strand of a target sequence, preferably a target sequence immediately 5' of a protospacer adjacent motif (PAM); N is 0; and:
the guide RNA includes one or more deoxyribonucleotides.

2. The method of claim 1, wherein the one or more deoxyribonucleotides comprise thymine in place of uracil.

3. The method of claim 1, wherein the one or more deoxyribonucleotides are within the sequence complementary to 17-20 consecutive nucleotides of the complementary strand of the target sequence.

* * * * *

UNITED STATES PATENT AND TRADEMARK OFFICE
CERTIFICATE OF CORRECTION

PATENT NO.         : 9,885,033 B2                                               Page 1 of 1
APPLICATION NO.    : 14/776620
DATED              : February 6, 2018
INVENTOR(S)        : J. Keith Joung et al.

It is certified that error appears in the above-identified patent and that said Letters Patent is hereby corrected as shown below:

In the Claims

In Column 114, Line 29 (approx.), in Claim 1, delete "$(X_N)$ ," and insert -- $(X_N)$; --

Signed and Sealed this
First Day of May, 2018

Andrei Iancu
*Director of the United States Patent and Trademark Office*

UNITED STATES PATENT AND TRADEMARK OFFICE
CERTIFICATE OF CORRECTION

PATENT NO. : 9,885,033 B2
APPLICATION NO. : 14/776620
DATED : February 6, 2018
INVENTOR(S) : J. Keith Joung et al.

It is certified that error appears in the above-identified patent and that said Letters Patent is hereby corrected as shown below:

In the Specification

Column 1, Line 16, replace "FEDERALLY SPONSORED RESEARCH OR DEVELOPMENT
This invention was made with Government support under Grant Nos. DP1 GM105378 awarded by the National Institutes of Health. The Government has certain rights in the invention."

With -- STATEMENT OF FEDERALLY SPONSORED RESEARCH
This invention was made with government support under Grant Nos. GM088040, AR063070, GM105378, HG005550, and GM105189 awarded by the National Institutes of Health, and W911NF-11-2-0056 awarded by the Army Research Laboratory - Army Research Office. The government has certain rights in the invention. --

Signed and Sealed this
Sixteenth Day of May, 2023

Katherine Kelly Vidal
*Director of the United States Patent and Trademark Office*